(12) United States Patent
Rodiera Olivé et al.

(10) Patent No.: US 10,537,267 B2
(45) Date of Patent: Jan. 21, 2020

(54) MONITORING A NEUROMUSCULAR BLOCKADE STATUS

(71) Applicants: José Javier Rodiera Olivé, Barcelona (ES); RGB Medical Devices S.A., Madrid (ES); Fundació Eurecat, Cerdanyola Del Vallés (ES)

(72) Inventors: José Javier Rodiera Olivé, Barcelona (ES); Antonio González Martínez, Madrid (ES); Francisco Javier Corral Herranz, Madrid (ES); Ricardo Ruiz Nolasco, Madrid (ES)

(73) Assignees: RGB Medical Devices S.A., Madrid (ES); Fundació Eurecat, Cerdanyola Del Vallés (ES); José Javier Rodiera Olivé, Barcelona (ES)

( * ) Notice: Subject to any disclaimer, the term of this patent is extended or adjusted under 35 U.S.C. 154(b) by 882 days.

(21) Appl. No.: 15/191,028

(22) Filed: Jun. 23, 2016

(65) Prior Publication Data

US 2016/0296141 A1    Oct. 13, 2016

Related U.S. Application Data

(63) Continuation of application No. 15/190,630, filed on Jun. 23, 2016, now Pat. No. 10,045,714, which is a
(Continued)

(30) Foreign Application Priority Data

Dec. 24, 2013  (ES) ............................... 201331489 U
Feb. 13, 2014  (ES) ............................... 201430202 U

(51) Int. Cl.
*A61B 5/00*    (2006.01)
*A61B 5/11*    (2006.01)
(Continued)

(52) U.S. Cl.
CPC ........ *A61B 5/1106* (2013.01); *A61B 5/02233* (2013.01); *A61B 5/0488* (2013.01);
(Continued)

(58) Field of Classification Search
CPC . A61B 5/021; A61B 5/02108; A61B 5/02116; A61B 5/02125; A61B 5/022;
(Continued)

(56) References Cited

U.S. PATENT DOCUMENTS 4,453,547 A * 6/1984 Castel ..................... A61N 1/08
                                                           128/908
5,957,860 A    9/1999 Rodiera Olive
(Continued)

FOREIGN PATENT DOCUMENTS

DE    102011101583 A1    11/2012
EP         0787506 A1     8/1997
WO      2012125425 A2     9/2012

*Primary Examiner* — Max F Hindenburg
(74) *Attorney, Agent, or Firm* — Edell, Shapiro & Finnan, LLC

(57) ABSTRACT

The present disclosure relates to various methods for determining a neuromuscular blockade status and systems suitable for performing such methods. The present disclosure further relates to electro-stimulation electrodes for stimulating a muscle of a patient, optionally in the context of at least some of the mentioned methods. The present disclosure still further relates to hybrid air-signal connectors for use in an electro-stimulation cuff which can be used in the context of at least some of the cited methods. The present disclosure also relates to electro-stimulation circuits comprising an electrode portion and a track portion suitable for pressure cuffs for electro-stimulation, and to pressure cuffs configured to be arranged around a limb of a patient and comprising an active electro-stimulation electrode and a passive electro-stimulation electrode. These electro-stimulation cir-
(Continued)

cuits and pressure cuffs may also be used in the context of at least some of the mentioned methods.

20 Claims, 29 Drawing Sheets

Related U.S. Application Data continuation of application No. PCT/EP2014/079041, filed on Dec. 22, 2014.

(51) Int. Cl.
*A61N 1/04* (2006.01)
*A61N 1/05* (2006.01)
*A61N 1/36* (2006.01)
*A61B 5/022* (2006.01)
*A61B 5/0488* (2006.01)
*A61B 5/05* (2006.01)

(52) U.S. Cl.
CPC .............. *A61B 5/05* (2013.01); *A61B 5/1107* (2013.01); *A61B 5/4519* (2013.01); *A61B 5/4836* (2013.01); *A61B 5/4848* (2013.01); *A61B 5/6824* (2013.01); *A61B 5/6828* (2013.01); *A61B 5/6831* (2013.01); *A61B 5/7203* (2013.01); *A61B 5/7275* (2013.01); *A61N 1/0452* (2013.01); *A61N 1/0492* (2013.01); *A61N 1/0496* (2013.01); *A61N 1/0556* (2013.01); *A61N 1/0558* (2013.01); *A61N 1/36003* (2013.01); *A61B 2505/05* (2013.01); *A61B 2562/0219* (2013.01); *A61B 2562/0247* (2013.01); *A61N 1/0484* (2013.01)

(58) Field of Classification Search
CPC ... A61B 5/0233; A61B 5/1106; A61B 5/1107; A61B 5/0488; A61B 5/05
See application file for complete search history.

(56) References Cited

U.S. PATENT DOCUMENTS

| | | | |
|---|---|---|---|
| 6,445,955 B1 | 9/2002 | Michelson et al. | |
| 6,532,388 B1 | 3/2003 | Hill et al. | |
| 9,743,846 B2* | 8/2017 | Ukawa | A61B 5/02133 |
| 2010/0081963 A1 | 4/2010 | Gilhuly | |
| 2012/0053655 A1 | 1/2012 | Bain et al. | |
| 2012/0065525 A1* | 3/2012 | Douniama | A61B 5/02116 |
| | | | 600/485 |
| 2012/0259236 A1* | 10/2012 | Parfenov | A61B 5/02116 |
| | | | 600/494 |
| 2013/0066412 A1 | 3/2013 | Van Der Beek et al. | |
| 2013/0079618 A1 | 3/2013 | Sandmore et al. | |
| 2013/0123601 A1 | 5/2013 | Lindberg et al. | |
| 2014/0128747 A1* | 5/2014 | Maltz | A61B 5/02007 |
| | | | 600/481 |
| 2014/0277327 A1 | 9/2014 | Netherton | |

* cited by examiner

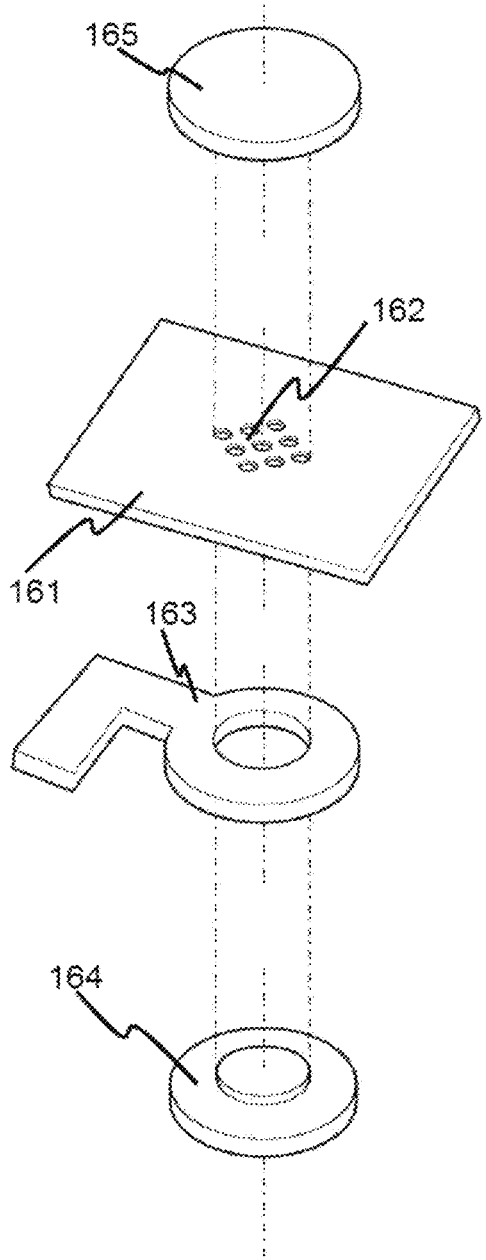
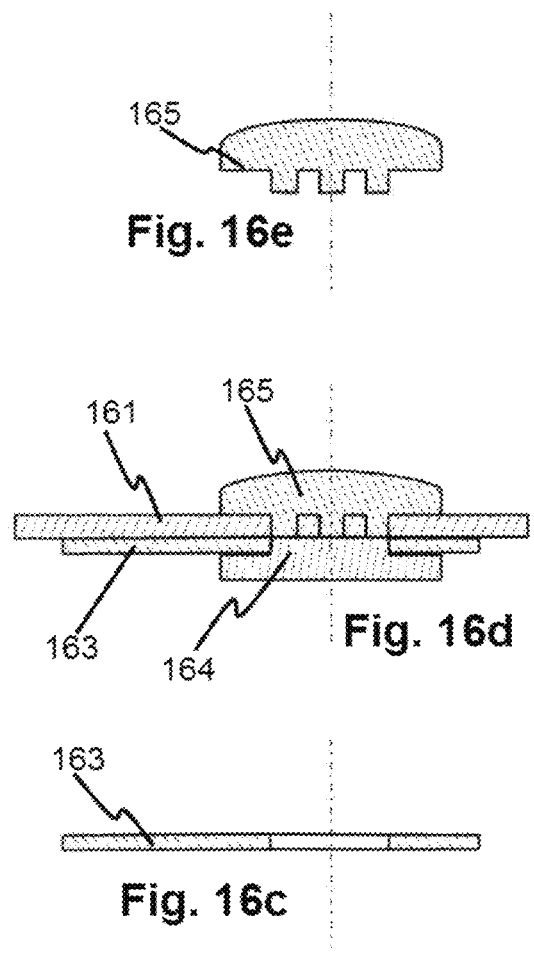
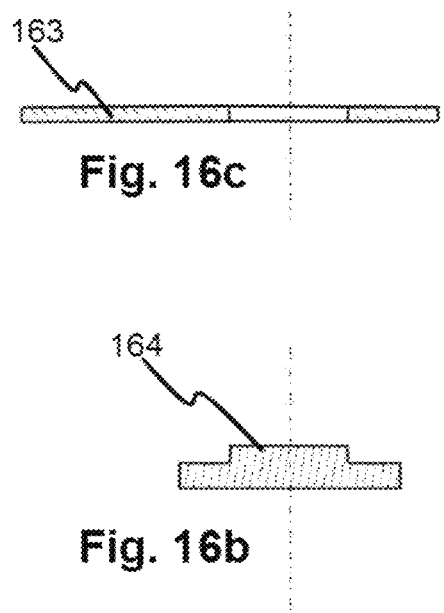

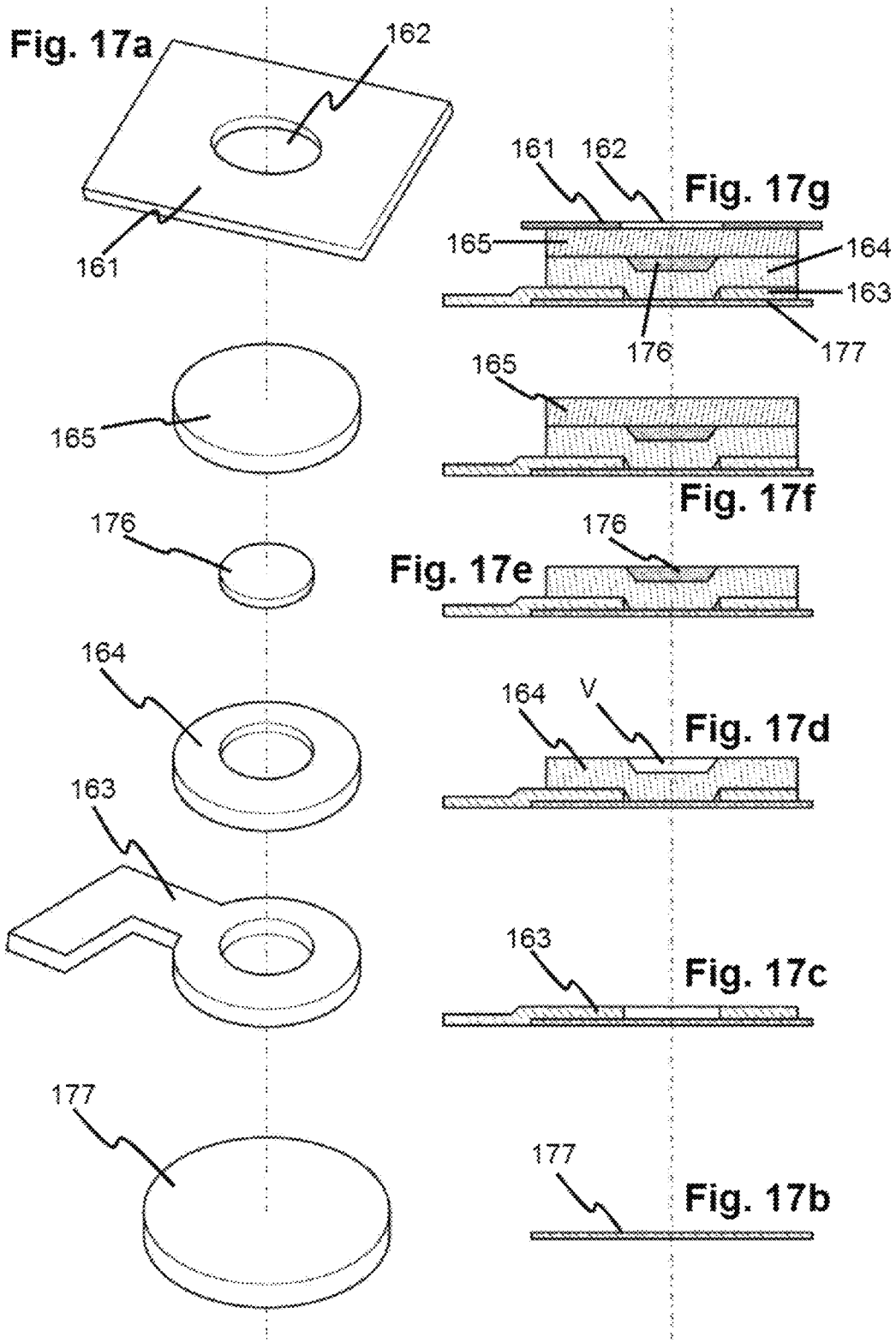

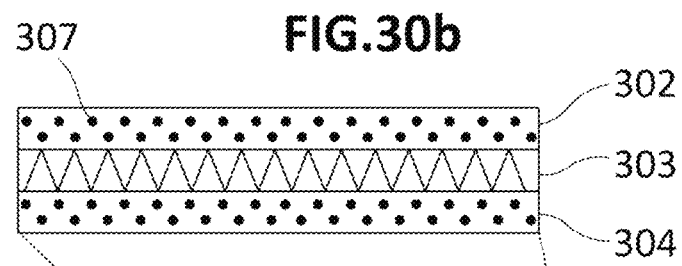
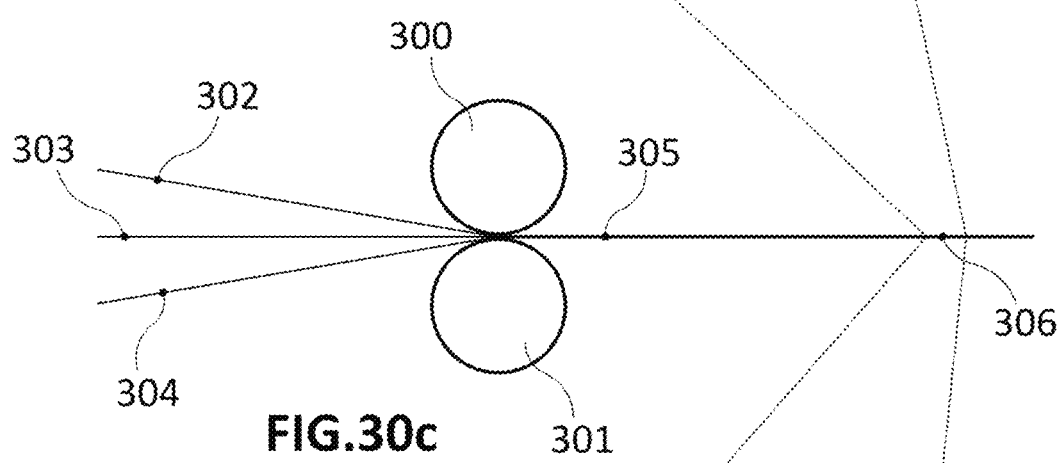
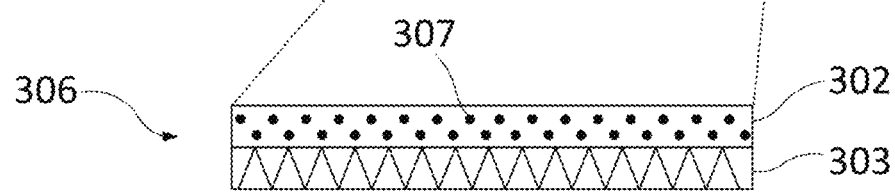

MONITORING A NEUROMUSCULAR BLOCKADE STATUS

CROSS-REFERENCE TO RELATED APPLICATIONS

This application relates to and claims the benefit and priority to U.S. application Ser. No. 15/190,630 filed Jun. 23, 2016, which claims the benefit and priority to International Application PCT/EP2014/079041 filed Dec. 22, 2014, which claims the benefit and priority to Spanish Patent Application Nos. U201331489 filed Dec. 24, 2013 and U201430202 filed Feb. 13, 2014.

TECHNICAL FIELD

The present disclosure relates to various methods for determining a neuromuscular blockade status and systems suitable for performing such methods.

The present disclosure further relates to electro-stimulation electrodes for stimulating a muscle of a patient, optionally in the context of at least some of the above methods.

The present disclosure still further relates to hybrid air-signal connectors for use in an electro-stimulation cuff which can be used in the context of at least some of the above methods.

The present disclosure also relates to electro-stimulation circuits comprising an electrode portion and a track portion suitable for pressure cuffs for electro-stimulation, and to pressure cuffs configured to be arranged around a limb of a patient and comprising an active electro-stimulation electrode and a passive electro-stimulation electrode.

Throughout the present disclosure, reference is made to "neuromuscular blockade". In the technical field, neuromuscular blockade may also be called "neuromuscular block" or "neuromuscular blockage". The term "neuromuscular blockade" as used herein therefore covers these terms as well.

BACKGROUND

Neuromuscular transmission may be defined as the transfer of a motor impulse between a nerve and a muscle in the neuromuscular junction. This transmission may be blocked through the use of muscle relaxants. Muscle relaxation may be used during surgery under general anaesthesia to allow e.g. endotracheal intubation and, in general, to provide the surgeon with the optimum working conditions depending on the type of intervention.

When muscle relaxants during surgery are used, it is very important to monitor the patient's neuromuscular blockade status. For such a monitoring, a peripheral motor nerve may be electrically stimulated and muscle response(s) to said stimulation may be processed to infer the neuromuscular blockade status. In clinical practice, various stimulation patterns may be used for different purposes and in different phases of the operation.

Systems and methods are known based on the above principles. These systems may comprise electrodes for electro stimulating the patient and sensors for detecting a response to the electro-stimulation.

The electrodes may be connected to a provider of electro-stimulation signals for receiving suitable signals from the provider. The electrodes may be attached to the skin of the patient at a body part suitable for stimulating a particular motor nerve, such as e.g. ulnar nerve.

The sensors may comprise e.g. an accelerometer attached to e.g. a fingertip of the patient for sensing the movement of the finger as a reaction to the electro-stimulation. The sensors may be connected to a sensing unit in such a way that signals from the sensor(s) are received by the sensing unit and processed to generate data representing a response to the electro-stimulation.

The electrodes and sensors may therefore be arranged separately on different parts of the body. This dispersion of the electrodes and sensors may make the set-up of the system time-consuming and the subsequent use of the system cumbersome, which may generate discomfort to the surgical team during surgery. It can even lead to surgeons and/or anaesthesiologists disregarding these systems during surgery.

The provider of electro-stimulation signals and the sensing unit may be integrated in a single monitor. The electrodes may be connected to the monitor through cables, and the sensors may be connected to the monitor through further cables. Therefore, various cables may be present between the patient and the monitor when the electrodes and sensors are attached to the patient.

Having such a plurality of cables between the monitor and the patient may be annoying for the surgical staff and may be a source of problems during surgery. For example, somebody may accidentally stumble into/over a cable and/or a tangle of cables may occur. This may cause detachment of an electrode/sensor from the patient and/or disconnection of the cable from the monitor.

U.S. Pat. No. 5,957,860A discloses an apparatus comprising means for stimulating a nerve (e.g. electrodes) and means for detecting a response to the stimulation. The apparatus is characterized in that said means are provided in a single body, which is a pressure cuff of the type generally used for measuring arterial pressure, provided with or connected to means for pressure detection. With this apparatus, the previously discussed problem about dispersion of electrodes and sensors is avoided, since they are provided in a single body.

U.S. Pat. No. 5,957,860A further discloses that the pressure cuff and integrated electrodes may be connected to a monitor through a tube configured to conduct both air and electricity. The monitor may send suitable electro-stimulation signals to the electrodes for muscle stimulation through said single tube. The monitor may also receive pressure variations in the cuff (representing a response to the muscle stimulation) also through said single tube. Hence, the previously discussed problem related to the presence of a plurality of cables between the patient and the monitor is avoided with this configuration.

The monitor may be adapted to receive instructions or parameters provided by an anaesthesiologist (or similar profile) for the monitor to transmit suitable stimulation signals to the electrodes according to said instructions or parameters. For instance, data on stimulation pattern(s) to be used at each time, periodicity of the signals, intensity of the signals, etc. may be provided by the anaesthesiologist to the monitor through suitable data entry means (e.g. a keyboard).

The monitor may also be adapted to receive signals from the sensors (accelerometer, cuff, etc.) and to process them in such a way that a representation of them may be provided to a display. This representation of the sensor signals may be displayed in the form of numerical values (e.g. percentages), graphics, etc. in such a way that the anaesthesiologist may derive a muscle response to the performed electro-stimulation.

It is known that the anaesthesiologist can test (or monitor) a neuromuscular blockade status for a patient by paying attention to the display and manually acting on the monitor depending on the muscle responses derived from the displayed data. Manually acting on the monitor may comprise providing new instructions/parameters to the monitor in order to cause the transmission of new stimulations signals with e.g. different intensity, or frequency or stimulation patterns depending on the new circumstances.

Several iterations of deriving muscle responses (from displayed data) and optionally acting on the monitor may be performed by the anaesthesiologist for finally achieving a target neuromuscular blockade status for the patient. This may be labour-intensive, time-consuming and cumbersome for the anaesthesiologist and may generate inefficiencies and/or deficiencies in the process of relaxation (i.e. the initial induction, subsequent maintenance, and eventual reversal of a drug-induced neuromuscular blockade status) of the patient.

Since the above method of monitoring (or testing) a neuromuscular blockade status highly depends on the attention paid by the anaesthesiologist, a delay between achievement of a neuromuscular status and corresponding actions on the monitor may occur. Delayed actuations may generate inefficiencies in terms of e.g. extending the occupation of an operating room, using greater amounts of muscle relaxant than really needed, etc.

Furthermore, in an Operating Room, momentary situations of high stress may exist so that an anaesthesiologist may miss the result of a precise electro-stimulation or may lose track of how many stimulations have been performed and previous results.

Said dependence on the anaesthesiologist's attention may also cause the anaesthesiologist to act erroneously on the monitor as a consequence of e.g. a wrong derivation of a muscle response from the displayed data. Wrong actuations by the anaesthesiologist may e.g. generate damage or risk of damage to the patient, which have to be attenuated during surgery. In this case, more surgical resources may be finally used than initially required.

In apparatuses based on obtaining or deriving muscle responses depending on how pressure varies in a pressure cuff (such as e.g. the one disclosed in U.S. Pat. No. 5,957, 860A), patient's heartbeats may create interferences that may distort the muscle response. Hence, subsequent actions and/or assessments based on said distorted responses may generate errors in e.g. monitoring (or testing) a neuromuscular blockade status for a patient.

Electro-stimulation electrodes are known for their application on the skin of a patient. These electrodes, which may be suitable for applications as the ones described before, may comprise a support layer and an electrically conductive material (or medium). The support layer may be made of an electrically insulating material and may be configured in such a way that, in use, a surface of the support layer contacts the skin of the patient.

The support layer may comprise at least one region having one or more holes. The electrically conductive medium may be adhered to a surface of the support layer which may be the opposite to the surface of contact with the skin of the patient. The electrically conductive medium generally extends over the holes and a conductive layer is interposed in between for conveying current to the skin.

A risk of this structure may be that the conductive layer may be torn or damaged at the level of the region of contact with the patient's skin and, therefore, the electrically conductive medium may come into direct contact with the skin. In these circumstances, a concentrated and relatively high current may be transmitted to the patient's skin.

Such a concentration of electrical energy may cause e.g. a burn on the skin of the patient, who may be under general anaesthesia if the patient is being subjected to a surgical operation. In this situation, the patient may thus not be able to alert the medical team about the damage he/she is suffering.

Connectors for electro-stimulation cuffs, or compressive armbands, are known configured to connect a tube for the conveyance of pressurized air to the cuff. These connectors may comprise a body comprising a base and a tubular portion arranged on one face of the base for the coupling of the tube.

These connectors may further comprise two connection electrodes having external terminals for connection with external cables, and internal terminals for connection to conductive tracks internal to the cuff. Such a special type of connectors which feature the ability of simultaneously conveying both pressurized air and electrical signals are referred herein as Hybrid Connectors.

Hybrid Connectors for electro-stimulation cuffs should ideally fulfil at least some of the following requirements:

a) transmission of electrical stimuli emitted from a monitor and conveyed through conductive wires electrically connecting the monitor to the pressure cuff, for finally discharging the electrical stimuli onto the patient's skin through corresponding electrodes.

b) entry of pressurized air into the bag of the compressive armband during the inflation phase thereof, and subsequent free evacuation of the air to e.g. the monitor and, from there, to the atmosphere.

c) pneumatic air tightness of the connection between the inflatable bag and the hybrid connector, without requiring the application of glues, adhesives, or any other type of sealant of chemical nature. A risk associated with such sealants may be that they can deteriorate over time and, therefore, air leakages may occur. Moreover, UNE-EN ISO 10.993 standards about "Bio-Compatibility of Medical Devices" may not be suitably fulfilled with the use of such sealants.

d) protection against intrusions (of liquids and/or dust) in the junction between the tube and the hybrid connector. Such intrusions can short-circuit the conveyance of electrical stimuli which may put at risk the physical integrity of the patient and/or surgery staff.

e) mechanical resistance of the junction between the tube and the hybrid connector without requiring the application of glues, adhesives, or any other type of sealant of chemical nature. This requirement is aimed at preventing that an excessive pulling of the tube (e.g. accidentally performed by its unnoticed dragging because of the busy circulation of the operation room's staff around the surgical table) could pull out the tube from its receptacle in the hybrid connector.

f) skin friendly nature since the hybrid connector may rest during surgery on a delicate skin covering the internal crook of the patient's arm. With this requirement, e.g. skin lacerations or irritations thereto may therefore be prevented.

U.S. Pat. No. 5,957,860A discloses a pressure cuff with two integrated electrodes for electro-stimulating a peripheral motor nerve of a patient. The electro-stimulation of the nerve may cause an evoked muscle response which may be evaluated in terms of a steep change in the air pressure inside an inflatable bag of the cuff. The magnitude of this air pressure change may determine, by using an appropriate computing algorithm, an indicator about the neuromuscular blockade status of the patient.

The electrodes include an active electrode (cathode or negative lead, through which current is supplied) and a passive electrode (anode or positive lead, through which current is collected). In between the electrodes, the current passes through a patient's limb, in particular a patient's arm.

FIG. 27a schematically shows a prior art pressure cuff 270 which comprises a first electro-stimulation electrode 273 and a second electro-stimulation electrode 274. The pressure cuff is shown further comprising an inflatable bag 275, and a flexible tube 276 for conducting air and electrical current between the cuff and a monitor or similar device configured to operate the cuff.

FIG. 27a also illustrates a theoretical line 271 representing a path of a nerve to be electro-stimulated through the electrodes 273, 274. The pressure cuff 270 is configured in such a way that, in use, the electrodes 273, 274 are arranged on a region of the limb which is at least partially on or "over" the nerve (theoretically represented by the line 271).

FIG. 27b offers an enlarged view of a region 272 indicated in FIG. 27a and from a point of view 277 also indicated in FIG. 27a.

As shown in FIG. 27c, the pressure cuff 270 is configured to be preferentially arranged around a patient's right limb (either arm or leg) with the first and second electrodes 273, 274 and the inflatable bag 275 being suitable arranged according to the following requirements:

The first electrode 273 functions as the anode (or positive lead) and is arranged in a proximal position on an ulnar nerve 278, and the second electrode 274 functions as the cathode (or negative lead) and is arranged in a distal position on the ulnar nerve 278. The particular requirements further comprise the inflatable bag 275 arranged on or over a brachial artery 279.

Pflüger's Law defines the conditions under which an active electrode 274 and a passive electrode 273 arranged on a path of a motor nerve 278 ensure that an evoked muscle response induced by a current transmitted by the active electrode 274 to the nerve 278 is reliable.

As shown in Table 1, this Law concludes that only when the active electrode 274 is in a distal position and the passive electrode 273 is in a proximal position, the evoked muscle response will reliably occur irrespective of the magnitude of the intensity of the current transmitted by the active electrode 274.

Herein, distal position refers to a distal position in the corresponding patient's limb with respect to the patient's trunk, and proximal position refers to a proximal position in the corresponding patient's limb with respect to the patient's trunk.

According to Pflüger's Law, an electro-stimulation performed by two electrodes 273, 274 placed on a motor nerve 278 can cause an evoked muscular response (described as "twitch" in Table 1) depending on two parameters. A first parameter refers to the intensity of the current generated to electro-stimulate the motor nerve 278, and a second parameter refers to the relative position of the electrodes 273, 274 on the path of the nerve 278. This second parameter is technically called "polarity".

Table 1 provides detailed data about this phenomenon. The term ON refers to the moment at which the electrical stimulus is actually applied to the nerve (closed circuit condition) and the term OFF refers to the moment at which the electrical stimulus is withdrawn (open circuit condition).

TABLE 1

| ELECTRIC CURRENT | POLARITY | | | |
| --- | --- | --- | --- | --- |
| | ACTIVE ON PROXIMAL | | ACTIVE ON DISTAL | |
| | ON | OFF | ON | OFF |
| WEAK | Twitch | No twitch | Twitch | No twitch |
| MEDIUM | Twitch | Twitch | Twitch | Twitch |
| STRONG | No twitch | Twitch | Twitch | No twitch |

In Table 1, three different intensities for the electrical current applied for electro-stimulation are considered: WEAK, MEDIUM and STRONG. The content of Table 1 permits deriving that a reliable muscle response can be obtained, irrespective of whether the intensity of the stimulating current is WEAK, MEDIUM or STRONG, only when the active electrode 274 is arranged in a distal position with respect to the passive electrode 273, as shown in FIG. 27c.

However, when the same pressure cuff is changed to a patient's left arm, the practitioner is now forced to rotate the pressure cuff 180° in order to—as shown in FIG. 27d-match the position of both the stimulating electrodes 273, 274 and the inflatable bag 275 with—respectively—the course of the peripheral motor nerve 278 and the brachial artery 279 on the patient's left arm. By doing so, nevertheless, the passive and active electrodes 273, 274 of the pressure cuff 270 will then unavoidably be laid out on the motor nerve 278 according to the "ACTIVE ON PROXIMAL" arrangement (as identified in Table 1).

As shown in Table 1, such an "ACTIVE ON PROXIMAL" arrangement suffers from the important limitation of not being able to warrant an effective evoked muscle response (TWITCH) after applying (ON) a stimulating current of STRONG intensity on the motor nerve.

This electro-physiological phenomenon is technically known as "Anodal Block of Conduction", which refers to the lack of evoked muscular response featured on a patient's muscle, when the motor nerve innervating said muscle is stimulated with a high electrical current intensity using a particular layout of electrodes.

This particular layout comprises the passive electrode (anode, positive lead) of the stimulating circuit placed further distal on the path of the motor nerve than the active electrode (cathode, negative lead). Such a scenario is referred to as "No Twitch" in Table 1, "ACTIVE ON PROXIMAL" Polarity, "ON" column, and "STRONG" Electric Current's row.

Said "Anodal Block of Conduction" has its root in the appearance of a positively charged electrical field under the passive electrode of the stimulating circuit, when said circuit is closed (ON in terms of Table 1). The existence of such a positively charged electric field leads to the so-called hyperpolarization of the nerve's trunk outer membrane. The magnitude of such a hyperpolarization is directly proportional to the strength of the positively charged electrical field, which is, in turn, directly proportional to the intensity of the electrical current applied for stimulating the nerve.

The propagation of a nervous impulse along a nerve's trunk could be assumed as being a propagation of a negatively charged electrical wave along the nerve. Therefore, a positively charged electrical field anywhere on the nerve's trunk between the active electrode and the innervated muscle may act as an electrical barrier for the propagation of the cited negatively charged electrical wave. Hence, the positively charged electrical field may block, below the passive electrode or anode (this explains the term "Anodal Block"), the eventual arrival of the electrical nerve impulse to the muscle of interest.

The unnoticed appearance of the "Anodal Block of Conduction" phenomenon may constitute a potential source of medical errors during the assessment of the neuromuscular blockade condition of a patient, primarily when stimulating a patient's peripheral motor nerve according to an "ACTIVE ON PROXIMAL" electrodes' set-up with a STRONG electrical current stimulation intensity. If no muscle response is obtained, the anesthetist may incorrectly diagnose that the patient is in a deep blockade condition whereas the patient might actually be in a non-blocked condition.

Such an observed lack of motor response may actually be caused by the undesired blockade of the nervous signal's propagation at the strongly hyperpolarized nerve's section under the passive electrode, which may be placed further distal on the path of the motor nerve which has been stimulated upstream.

At the current day, the only way to prevent the occurrence of the "Anodal Block of Conduction" phenomenon is to actively invert, through corresponding software, the Polarity of the electrodes when the pressure cuff is arranged around a left limb. However, as such a reversal operation has to be manually carried out by the practitioner on e.g. a console, monitor or similar, this solution is not failure proof.

Pressure cuffs incorporating electro-stimulation circuits are known from U.S. Pat. No. 5,957,860A. Such electro-stimulation circuits may comprise electrodes and related connections which are made with conventional electric components such as e.g. metallic plates for the electrodes and metallic wires for the connection of the electrodes to a corresponding electricity source.

This kind of electro-stimulation circuits incorporated in a pressure cuff may be relatively stiff, voluminous, and non-ergonomic, so that they may be annoying to the patient to whom the circuit is applied for electro-stimulation. Moreover, the fabrication of said circuits may be complicated and time-consuming because a relative large number of manual actions may be required.

The attachment of these electro-stimulation circuits to the pressure cuff may comprise adhesives or similar substances which may cause alterations, such as e.g. irritation, of the skin of the patient to which the circuit is applied for electro-stimulation.

The present disclosure aims at improving upon the prior art methods of monitoring a neuromuscular blockade status and systems suitable for such methods.

SUMMARY OF THE DISCLOSURE

In a first aspect, a method is provided for automated determination of a neuromuscular blockade status in a patient to whom a muscle relaxant has been delivered. The method is based on a plurality of predefined neuromuscular blockade status, each of them having predefined one or more stimulation cycles with a cycle periodicity and one or more criterions for changing from the neuromuscular blockade status to another neuromuscular blockade status. The one or more criterions comprise a first criterion or first set of criterions for changing the neuromuscular blockade status to a first other neuromuscular blockade status.

The method comprises automatically performing one or more stimulation cycles predefined for the neuromuscular blockade status, and automatically determining one or more muscle responses to at least some of the performed stimulation cycles. The method further comprises automatically comparing the muscle responses with the predefined criterions for changing the neuromuscular blockade status, and, if the muscle responses fulfil the predefined first criterion or first set of criterions, then automatically performing one or more stimulation cycles predefined for the first other neuromuscular blockade status.

The proposed method may be implemented in the form of e.g. a computer program which may executable by a suitable system. The aforementioned drawbacks of the prior art methods may be thus overcome with such an approach. Derivation of muscle responses and consequent (re)configuration of subsequent stimulation signals may be automatically performed by the method/system without requiring an anaesthesiologist (or similar profile) to pay attention continuously or periodically.

The proposed method may be continuously repeated in such a way that transitions between different predefined neuromuscular statuses may automatically occur until a target predefined neuromuscular status is achieved. Given a current status for the patient, a stimulation cycle predefined for said current status may be repeated under a periodicity predefined for said stimulation cycle. Each performed stimulation cycle may produce a muscle response to said stimulation.

One or more of the last muscle responses may be compared to one criterion or a set of criterions predefined for the current status. If one of the criterions or the set of criterions is fulfilled, the neuromuscular blockade status can be changed from the current status to a new status predefined for the fulfilled criterion. Hence, the current status becomes a previous status whereas the new status becomes the current status. Then, new iterations of the method may be performed for the "new" current status. And so on until a target neuromuscular status (e.g. unblocked status) is achieved.

The method may further comprise, however, displaying representations of the determined muscle responses, such that the anaesthesiologist may take them into account if desired. The method may also be adapted to receive manual instructions from the anaesthesiologist aimed at replacing (possibly temporary) at least some of the "automatic" predefined stimulation cycles, periodicities, criterions, etc.

In some implementations, the one or more criterions for changing from the neuromuscular blockade status to another neuromuscular blockade status may further comprise a second criterion or second set of criterions for one or more of the neuromuscular blockade status. The second criterion or second set of criterions may be predefined for changing the neuromuscular blockade status to a second other neuromuscular blockade status. Then, if the muscle responses fulfil said predefined second criterion or second set of criterions, one or more stimulation cycles predefined for the second other neuromuscular blockade status may be automatically performed.

Each of the predefined neuromuscular statuses may have associated one or more stimulation cycles, each of them being predefined according to a stimulation pattern, such as e.g. a Single Twitch (ST) pattern, or Train of Four (TOF) pattern, or Post-tetanic count (PTC) pattern, etc. More detailed explanations about these patterns may be provided in other parts of the description.

Each predefined neuromuscular blockade status may have predefined one or more stimulation cycles each having predefined a corresponding criterion or set of criterions for changing to another neuromuscular blockade status. In an example, an induction status (which means that blockade is being induced in the patient) may have predefined a single TOF stimulation cycle and a single (first) criterion or (first) set of criterions depending on one or more responses to said TOF stimulation(s).

In another example, a deep status (which means that the patient is considered deeply blocked) may have predefined a first stimulation cycle according to a TOF pattern, and a second stimulation cycle according to a PTC pattern which is more sensitive than the TOF pattern. In other words, the PTC pattern may permit detecting neuromuscular transmissions that the TOF pattern cannot detect.

Taking the above into account, a first criterion or first set of criterions may be predefined for the TOF stimulation cycle for changing to less deep statuses (e.g. moderate status), and a second criterion or second set of criterions may be predefined for the PTC stimulation cycle for changing to more deep statuses (e.g. intense status). After performing one or more TOF stimulation cycles, if no neuromuscular transmission is detected (or inferred), then the PTC stimulation cycle and the second criterion or second set of criterions may be applied to infer weaker neuromuscular transmissions and accordingly changing to a new status as predefined in said second criterion or second set of criterions.

According to examples, the one or more muscle responses may be determined through a pressure cuff applied to a limb of the patient, such that any muscle response has a form of a pressure wave representative of how pressure varies over time in the cuff as a result of said limb's muscle reaction to corresponding performed stimulation cycle(s).

In alternative examples, the one or more muscle responses may be determined through other types of sensors. For example, an accelerometer (arranged on e.g. a fingertip of the patient) can be used in the context of accelerometry methods, and/or force sensors may be used in the context of mechanomyography methods.

In a second aspect, a method is provided for determining a muscle response to an electro-stimulation of the muscle in a patient, by analysing the pressure wave in the cuff and filtering the interferences from pressure pulses generated by the heartbeats of the patient. In particular, the method comprises determining the end of a heartbeat of the patient, and performing the electro-stimulation of the muscle by causing generation of a first electro-stimulation pulse and, subsequently, one or more further electro-stimulation pulses. The first electro-stimulation pulse is generated substantially at the end of the heartbeat.

The method further comprises determining the muscle response in the form of a pressure wave representing how pressure varies over time in a pressure cuff as a muscle reaction to the electro-stimulation. The pressure wave comprises first and further pressure pulses induced by the first and further electro-stimulation pulses respectively. The method also comprises determining a first characteristic indicative of the shape of the upward slope of the first pressure pulse.

The first characteristic of the upward slope of a pressure pulse may be e.g. the result of dividing the amplitude of the pressure pulse by the maximum derivative of the upward slope.

The method furthermore comprises, for at least some of the further pressure pulses, determining the first characteristic of the further pressure pulse, determining a deviation between the first characteristic of the further pressure pulse and the first characteristic of the first pressure pulse, and verifying if the deviation exceeds a deviation threshold.

The end of the patient's heartbeat may be determined by using any known system/method aimed at inferring a curve representing the heartbeat. This curve may have an upward slope, a peak, and a downward slope. The end of the heartbeat may be determined when the downward slope of the heartbeat curve substantially ends.

Diverse experiments have revealed that all the pressure pulses (in the muscle response) with amplitude greater than zero have, in the absence of interferences due to patient's heartbeat, an upward slope with a similar shape. Generating the first electro-stimulation pulse at the end of a heartbeat may permit assuming that the first pressure pulse (induced by said first electro-stimulation pulse) is free of interferences due to patient's heartbeat.

Hence, a deviation between the first characteristic of a further pressure pulse and the first characteristic of the first pressure pulse (free of heartbeat interferences) may indicate that the further pressure pulse has been distorted by a heartbeat of the patient. If the deviation is below a deviation threshold, which may indicate that the distortion is substantially small, a correction based on the first characteristic of the first pressure pulse may be applied to the further pressure pulse in order to at least partially eliminate (or attenuate) said distortion.

In case of a negative result of verifying if the deviation exceeds a deviation threshold, an adjustment of the further pressure pulse is performed. This adjustment is carried out by assuming that the time until peak (or rising time) of the further pressure pulse is measured correctly and that the shape of its upward slope can be described by the first characteristic of the first pressure pulse.

In some implementations, in case of a positive result of verifying if the deviation exceeds a deviation threshold, an adjustment of the further pressure pulse may be performed either based on a first assumption or on a second assumption. The first assumption may presume that the time until peak (or rising time) of the further pressure pulse is measured correctly and that the shape of its upward slope can be described by the first characteristic of the first pressure pulse.

The second assumption may presume that the time until peak (or rising time) of the further pressure pulse is measured correctly and that the shape of its upward slope can be described by substantially subtracting a heartbeat pulse of reference from the measured further pressure pulse.

If the deviation between the first characteristic of the further pressure pulse and the first characteristic of the first pressure pulse is above the deviation threshold, which may indicate that the distortion is substantially significant, either a first correction or a second correction may be applied to the further pressure pulse in order to at least partially eliminate (or attenuate) said distortion.

The first correction may be based on the first characteristic of the first pressure pulse, and the second correction may be based on substantially subtracting a heartbeat pulse of reference from the measured further pressure pulse. Either the first or the second correction may be selected depending on the magnitude of the correction. For example, the correction with smaller magnitude may be selected in order to avoid applying an excessive correction to the further pressure pulse.

The proposed methods may therefore permit determining a "filtered" muscle response without or with smaller distortion(s) due to patient's heartbeat. These methods may be used in methods based on using an electro-stimulation cuff as the ones described in other parts of the description. These methods may produce more reliable results when using said methods.

In yet a further aspect, an electro-stimulation electrode is provided which is configured to be applied dryly (i.e. suitable for its dry application) on the skin, preferably intact skin, of a patient. The concept of dry application may refer to the application of the electro-stimulation electrode without the need of applying any electrically conductive gel under it.

The electro-stimulation electrode comprises a support layer, an electrically conductive medium, and a first conductive layer. The support layer is made of an electrically insulating material and has at least one region with one or more holes. The support layer is arranged in such a way that, in use, a first surface (or outer surface) of the support layer contacts the patient's skin. This outer surface of the support layer is therefore aimed at coming into contact with the patient's skin.

The electrically conductive medium is adhered to a second (or inner) surface of the support layer, opposite to the first surface, and arranged completely or partially surrounding the region with holes in such a way that the electrically conductive medium does not cover said region with holes. In other words, the electrically conductive medium is arranged around the region with holes, such that the electrically conductive medium completely or partially surrounds said region (with holes) in such a way that the electrically conductive medium does not overlap with said region (with holes).

The first conductive layer contacts the electrically conductive medium in such a way that the first conductive layer covers (or overlaps with) the region with holes.

The suggested electro-stimulation electrode substantially eliminates the risk of causing burns on the patient's skin. This effect is achieved because the electrical current is transmitted to the patient's skin through the one or more holes (of the support layer) from surrounding positions, since the electrically conductive medium (completely or partially) surrounds said region with holes. Therefore, the electrical current conveyed by the electrically conductive medium cannot reach the skin of the patient directly from the electrically conductive medium itself.

In yet another aspect, a hybrid air-signal connector is provided for connecting an air-signal tube to an electro-stimulation cuff. The hybrid air-signal connector is therefore aimed at connecting the electro-stimulation cuff with a tube of introduction of pressurized air and electrical pulse. The electro-stimulation cuff may have inner conductive tracks and a connection bore, and the air-signal tube may have an air conduit and electrically conductive cables.

The hybrid air-signal connector comprises a main body and two connection electrodes. The main body has a base with a first tubular portion arranged on a first face of the base in such a way that, in use, the first tubular portion is fitted into the air conduit of the air-signal tube such that air can flow between the air conduit and the inside of the cuff through the first tubular portion. In other words, the main body comprises a base from whose centre a tubular portion extends on one side, so-called outer side, the tubular portion being for coupling of the tube.

The two connection electrodes may be either L-shaped or substantially flat.

The connection electrodes have external terminals (for connection with external cables) and internal terminals (for connection with conductive tracks internal to the cuff).

In the case of the L-shaped electrodes, the external terminals extend from the base parallel (and optionally contiguously) to the first tubular portion in such a way that, in use, each external terminal contacts one of the electrically conductive cables of the air-signal tube.

In the case of the substantially flat electrodes, the external terminals are embedded in the base with an end portion arranged on the first face of the base in such a way that, in use, this end portion contacts an electrically conductive cable of the air-signal tube.

The internal terminals (of either L-shaped or substantially flat electrodes) are embedded in the base with an end portion arranged on the first face of the base in such a way that, in use, the end portion contacts one of the inner conductive tracks of the cuff when the hybrid air-signal connector is introduced into the connection bore of the cuff. In other words, the internal terminals are embedded in the base with their ends exposed on the outer side of the base, so that said ends come into contact with the tracks when the hybrid air-signal connector is introduced into a connection bore of the cuff.

The proposed hybrid air-signal connectors permit a relatively effective connection of an air-signal tube to an electro-stimulation cuff. A relatively effective connection of the wires comprised in the air-signal tube to the inner conductive tracks of the cuff can be effectively implemented through said hybrid air-signal connector as a result of the particular configuration and arrangement of its connection electrodes.

The hybrid air-signal connector may also permit an effective air flow between the tube and the cuff when the first tubular region of the connector is fitted into the air conduit of the tube. Suitable pneumatic air tightness, protection against intrusions of liquids and/or dust, mechanical resistance against sudden pulling efforts and a skin friendly nature may also be provided by the said hybrid air-signal connector if e.g. a proper material is chosen for its manufacturing.

In a yet further aspect, a pressure cuff is provided configured to be arranged around a limb of a patient and comprising an active electro-stimulation electrode and a passive electro-stimulation electrode.

The active electro-stimulation electrode (cathode or negative lead) is configured to transmit an electrical current and is arranged in the pressure cuff in such a way that, in use, a contact surface of the active electro-stimulation electrode is arranged on a first region of the limb, which is at least partially on a peripheral motor nerve of the limb such that the nerve receives at least part of the transmitted electrical current.

The passive electro-stimulation electrode (anode or positive lead) is configured to collect an electrical current and is arranged in the pressure cuff in such a way that, in use, a contact surface of the passive electro-stimulation electrode is arranged on a second region of the limb, such that the transmitted electrical current is collected by the passive electro-stimulation electrode.

The second region of the limb is not on the peripheral motor nerve, and/or the contact surface of the passive electro-stimulation electrode is substantially larger in size than the contact surface of the active electro-stimulation electrode.

The proposed pressure cuff may be used for assessing the drug-induced neuromuscular blockade condition of an anesthetized patient, by measuring the strength of an evoked muscular response obtained from the cuff as a result of electro stimulating the peripheral motor nerve.

This strength of the evoked muscular response may be determined by measuring, with the use of an appropriate computing algorithm, the magnitude of the air pressure peak that occur inside an inflatable bag of the cuff on each muscular motor response.

As described in other parts of the description, a phenomenon known as "Anodal Block of Conduction" may block the propagation of a nerve impulse induced by the electro-stimulation, which may cause the absence of evoked muscular response. The unnoticed appearance of the "Anodal Block of Conduction" phenomenon may constitute a potential source of medical errors during the assessment of the neuromuscular blockade condition of a patient.

With the proposed pressure cuff, the potential risk of incorrectly assessing the neuromuscular blockade condition of a patient because of the unnoticed event of the "Anodal Block of Conduction" phenomenon is substantially reduced or even eliminated.

If the proposed pressure cuff is arranged on either the right or left arm of the patient with the passive electrode in a proximal position with respect to the active electrode, a reliable evoked muscle response will always occur according to Pflüger's Law. This principle is irrespective of whether the passive electrode is arranged on the motor nerve's course or not, and of whether the passive electrode is larger in size than the active electrode or not.

With the proposed pressure cuff, regardless of whether it is arranged on either the right or left arm of the patient, and even with the passive electrode in a distal position with respect to the active electrode, a reliably evoked muscle response will also occur:

If the passive electrode (even if in the distal position) is not arranged on the motor nerve's course, the risk of blockade of the normal propagation of nerve impulses along said nerve's trunk due to the unnoticed appearance of the "Anodal Block of Conduction" phenomenon may be non-existent. This is because the passive electrode (in the distal position) is placed outside the area of influence of the motor nerve, so that no hyperpolarization of the outer membrane of the nerve may be induced by the passive electrode. Such an avoidance of the risk of unnoticed blockade of the propagation of nerve impulses is irrespective of the size of the contact surface of the passive electrode (in the distal position) with the patient's skin.

If the passive electrode (in the distal position) is arranged on the motor nerve's course and its contact surface with the patient's skin has a size larger than the contact surface of the active electrode, the risk of blocking the normal propagation of nerve impulses along the nerve's trunk due to the unnoticed appearance of the "Anodal Block of Conduction" phenomenon, may also be relatively low or even non-existent. This is because the larger size of the passive electrode acts as a diffuser which effectively reduces the density of electrical current existing at any point of the said contact surface of the passive electrode with the patient's skin. As a consequence, this low density of electrical current also creates a relatively weak positively charged electrical field under said contact surface which in turn, induces a relatively low hyperpolarization level on the outer membrane of the motor nerve's trunk. Hence the risk of appearance of the "Anodal Block of Conduction" phenomenon is significantly reduced or even eliminated.

In some examples, the second region of the limb may be at least partially on the peripheral motor nerve of the limb, and the contact surface of the passive electro-stimulation electrode may be substantially larger in size than the contact surface of the active electro-stimulation electrode. In some particular examples, the contact surface of the passive electro-stimulation electrode may substantially completely surround the contact surface of the active electro-stimulation electrode in a, for example, substantially coaxial manner.

An advantageous aspect of having the active electrode completely surrounded by the larger passive electrode may be that the electrical protection of the patient's heart may be improved. This is based on that the larger contact surface of the passive electrode constitutes an effective and preferential exit for the electro-stimulation current, so that said current does not flow towards the patient's heart. This conclusion may be further based on that such a preferential exit for the electro-stimulation current covers the entire 360 degrees around the active electrode.

In some examples wherein the passive electrode is larger than the active electrode, the contact surface of the passive electro-stimulation electrode may partially surround the contact surface of the active electro-stimulation electrode. For example, the passive electro-stimulation electrode may be substantially C-shaped. In other examples, the passive electro-stimulation electrode may be formed as two annular segments, each having a first end and a second end, the first ends facing each other with a first gap in between and the second ends facing each other with a second gap in between.

An aspect of these last configurations (C-shaped and those based on annular segments) may be that they also benefit from the diffusing effect of the electrical current density explained before. Hence, the risk of appearance of the "Anodal Block of Conduction" phenomenon is significantly reduced or even eliminated. Moreover, the passive electrode may also constitute an effective and preferential exit for the electro-stimulation current, covering the almost entire 360 degrees around the active electrode, which may improve the electrical protection of the patient's heart.

Any of the previous configurations of active and passive electrodes described in the context of pressure cuffs may be implemented based on the features and principles described in other parts of the description with respect to electro-stimulation circuits formed as a single multilayer film.

In a yet another aspect, electro-stimulation circuits are provided comprising an electrode portion and a track portion. The electrode portion is configured to either transmit or collect an electrical current to/from a region of a patient's skin for electro-stimulating a peripheral motor nerve of the patient. The track portion is configured to conduct the electrical current to/from the electrode portion. The electrode and track portions are integrally formed as a single multilayer film having a plurality of layers.

The plurality of layers comprises a first layer and a second layer attached to each other. The first layer may be made of thermoplastic polymer, such as e.g. Thermoplastic polyurethane (TPU) and/or Polyvinyl chloride (PVC), doped with electrically conductive particles, such as e.g. graphite particles. The second layer may be made of electrically conductive material, such as e.g. an electrically conductive fabric which may comprise carbon fibre and/or a metallic mesh.

The proposed electro-stimulation circuits may be fabricated in ways which can be easily scaled up. They may be manufactured in single-step manufacturing processes such as thermal continuous lamination. Besides, these electro-stimulation circuits may subsequently be easily adhered to a pressure cuff cover without the need of using adhesives or similar substances, thanks to the welding properties of the thermoplastic polymer of the first layer.

The first layer may permit skin friendly transmissions of electricity between the electrode portion and a target region of the patient's skin for stimulating a nerve. The second layer may provide efficient electrical conductivity properties to the track portion for conducting electricity to/from the electrode portion of the circuit.

In some examples, the plurality of layers may further comprise a third layer of thermoplastic polymer attached to the second layer in such a way that the second layer is sandwiched between the first layer and the third layer. This third layer may be made of thermoplastic polymer doped with electrically conductive particles.

According to examples, the layers of the plurality of layers may be attached together with a heated lamination process. This process may be a single step process, which may therefore make the fabrication of the electro-stimulation circuits less complicated and less time-consuming in comparison with other manufacturing processes such as e.g. layer-by-layer deposition of thin films (used e.g. in Printed Electronics and/or Phase-Vapour Deposition technologies).

In addition, since the abovementioned lamination process is a continuous manufacturing process, it also provides benefits in terms of cost savings derived from the economies of scale. More detailed argumentation is provided in other parts of the description.

In examples, a pressure cuff may be provided which may be configured to be arranged around a limb of a patient and may comprise at least one of the previous electro-stimulation circuits. The electro-stimulation circuit may be attached to the pressure cuff in such a way that, in use, a contact surface of the electrode portion of the electro-stimulation circuit is arranged on a region of the limb such that an electrical current can be either transmitted or collected by the electrode portion to/from said region of the limb for electro-stimulating a peripheral motor nerve.

The attachment of the electro-stimulation circuit to the pressure cuff may comprise an attachment of a layer of the electro-stimulation circuit made of thermoplastic polymer to a region of the pressure cuff also made of thermoplastic polymer. For example, the pressure cuff may comprise a fabric cover having a layer made of thermoplastic polymer to which the layer of thermoplastic polymer of the electro-stimulation circuit may be attached. This fabric cover may comprise a further layer made of nylon, paper or nonwoven fabric attached to the layer of thermoplastic polymer through e.g. a heated lamination process.

Such a layer of nylon, paper or nonwoven fabric may be an outer layer of the fabric cover and the layer of thermoplastic polymer may be an inner layer of the fabric cover, such that a relatively compact and resistant pressure cuff may be obtained. The outer layer of nylon, paper or nonwoven fabric may generally attribute enough strength to the cuff, whereas the inner layer of thermoplastic polymer may permit a relatively strong attachment of the electro-stimulation circuit(s) to the cuff. This may also contribute to make the inflatable bag of the pressure cuff leak-proof.

The attachment between the thermoplastic polymer layer of the circuit(s) and the thermoplastic polymer layer of the fabric cover may be implemented with a welding process. This welding process may be e.g. a hot plate welding process or an ultrasound welding process or a radio frequency welding process. An advantageous aspect of using a radio frequency welding process may be that it may effectively avoid the appearance of creases, fissures and/or deformations on the outer surface of the materials to be welded. This advantage is due to that the radio frequency welding process only applies heat at the specific contact interface between the two layers to be welded, while keeping the rest of said layers at room temperature.

Any of the previous electro-stimulation circuits formed as a single multilayer film and related principles may be used for fabricating any of the pressure cuffs with an active electro-stimulation electrode and a passive electro-stimulation electrode described in other parts of the description.

BRIEF DESCRIPTION OF THE DRAWINGS

Non-limiting examples of the present disclosure will be described in the following, with reference to the appended drawings, in which:

FIG. 16a is an exploded perspective view of an electro-stimulation electrode according to a first example;

FIGS. 16b to 16e are cross-sectional views of the electro-stimulation electrode according to the first example;

FIG. 17a is an exploded perspective view of an electro-stimulation electrode according to a second example;

FIGS. 17b to 17g are cross-sectional views showing the steps of assembling the electro-stimulation electrode according to a second example;

FIG. 27b schematically illustrates a region of the pressure cuff of

FIG. 27a taken from a point of view indicated in FIG. 27a;

FIG. 30a schematically illustrates a sectional view of a portion of a laminated base material suitable for constructing electro-stimulation circuits according to an example;

FIG. 30b schematically illustrates a sectional view of a portion of another laminated base material suitable for constructing electro-stimulation circuits according to another example;

FIG. 30c schematically illustrates a process of fabricating a laminated base material similar to the ones shown in FIGS. 30a and 30b;

DETAILED DESCRIPTION

Figure 1:
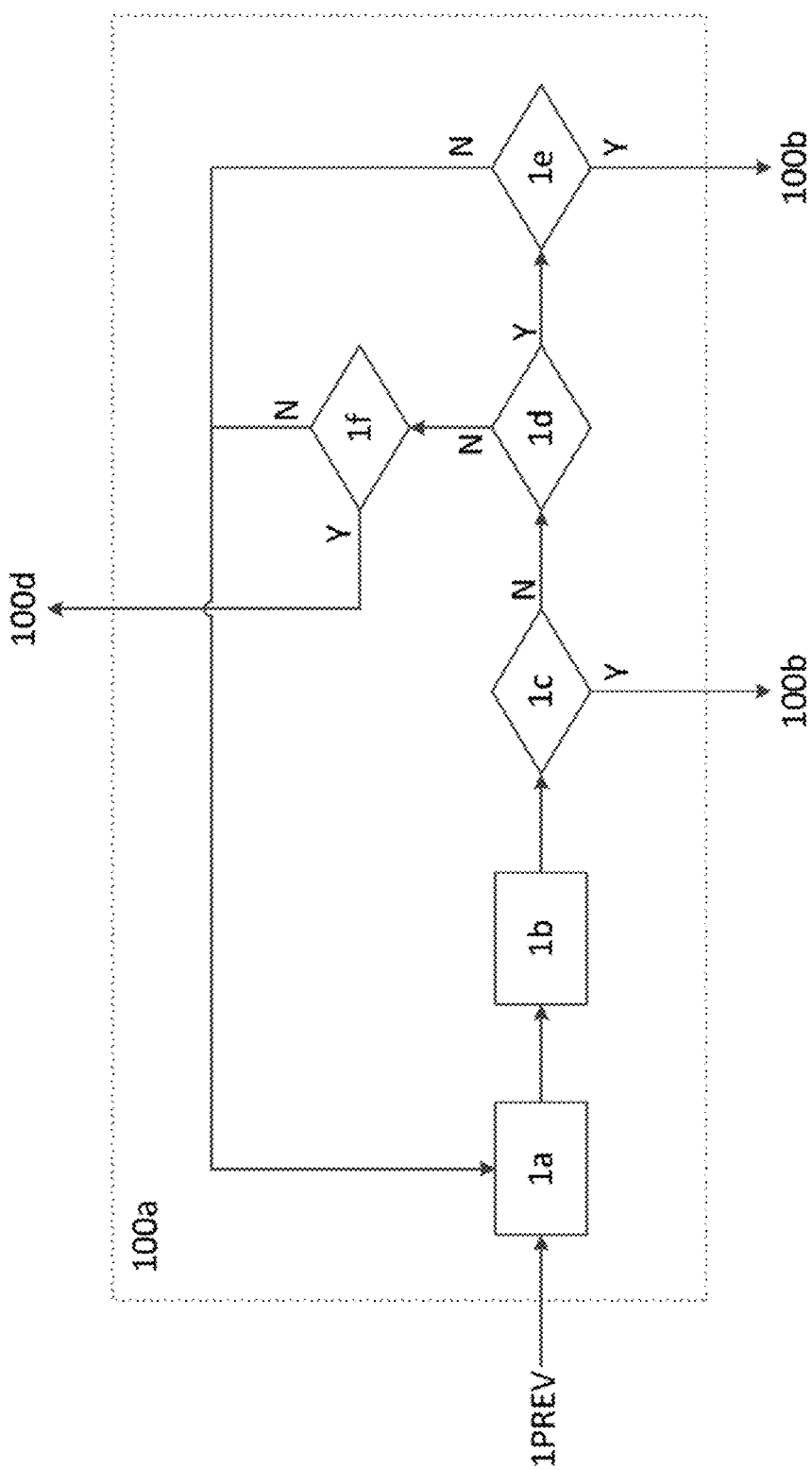
FIG. 1 is a flow chart schematically illustrating automatic changes from induction status to other statuses in a method for automated determination of a neuromuscular blockade status in a patient according to a first example.

FIGS. 1 to 8 are flow charts schematically illustrating automatic transitions between statuses in the context of methods for automated determination of a neuromuscular blockade status for a patient. During surgery, depending on the circumstances, the neuromuscular transmission may be blocked by delivering a muscle relaxant to the patient and said blockade may be reverted by delivering to the patient a drug aimed at that end.

Methods are based on having predefined a plurality of neuromuscular blockade statuses, each having predefined one or more stimulation cycles with a cycle periodicity and one or more criterions for changing the neuromuscular blockade status to another neuromuscular blockade status.

Examples of predefined neuromuscular statuses may be e.g. induction status, moderate status, deep status, intense status, reversion status, and end-of-reversion status. Unblocked status may be a "fictitious" status indicating that some ending condition has arisen, which may cause ending of the method.

Induction status may refer to that a muscle relaxant has been delivered to the patient and affectation of the muscle relaxant is in progress towards a desired neuromuscular blockade.

Moderate status may refer to that a neuromuscular blockade has been achieved which is not very high, so that some response(s) to TOF (train-of-four) stimulation(s) may occur, such as e.g. TOF-count between 1 and 3.

Deep status may refer to that a neuromuscular blockade has been achieved which is higher, so that no response(s) to TOF stimulation(s) can be obtained but some response(s) to PTC (post-tetanic count) stimulation(s) may occur.

Intense status may refer to that a neuromuscular blockade has been achieved which is very intense, so that no response(s) to any type of stimulation(s), either TOF or PTC stimulation(s), can be obtained.

Reversion status may refer to that the neuromuscular blockade is being reverted by e.g. delivering to the patient a drug aimed at that purpose. This drug may be a "standard reversion" drug or a "faster reversion" drug. More details about said types of drugs are provided in other parts of the description.

These statuses are well defined in medical literature.

End-of-reversion status may refer to that reversion of the neuromuscular blockade is close to its end, so that the method may be ended when a predefined ending condition (based on e.g. TOF stimulation(s)) is finally satisfied.

The one or more predefined stimulation cycles may comprise one or more stimulation cycles according to a Single Twitch (ST) pattern based on generating a single ST stimulation pulse. In this case, a muscle response to a performed ST stimulation cycle may comprise a single ST response pulse induced by the ST stimulation pulse.

A ST-ratio parameter may be inferred from a ST muscle response, said ST-ratio corresponding to the percentage of the ST response pulse with respect to a ST response pulse of reference determined before delivering the muscle relaxant to the patient. Since ST patterns are well known in monitoring neuromuscular blockade, no further details will be provided to this respect.

The one or more predefined stimulation cycles may comprise one or more stimulation cycles according to a Train of four (TOF) pattern. A TOF pattern may be based on generating first, second, third and fourth TOF stimulation pulses with a frequency of 2 Hz. A muscle response to a performed TOF stimulation cycle may thus have first, second, third and fourth TOF response pulses induced by the first, second, third and fourth TOF stimulation pulses respectively.

A TOF-count parameter and a TOF-ratio parameter may be inferred from a TOF muscle response. The TOF-count parameter may correspond to the number of TOF response pulses with amplitude greater than zero in the TOF muscle response. The TOF-ratio parameter may correspond to the percentage of the fourth TOF response pulse with respect to the first TOF response pulse.

Since TOF patterns are well known in monitoring neuromuscular blockade, no further details will be provided to this respect.

The one or more predefined stimulation cycles may comprise one or more stimulation cycles according to a Post-tetanic count (PTC) pattern based on a tetanus stimulation during between 2 and 8 seconds (e.g. 5 seconds), followed by a period of single twitch (ST) pulses of between 10 and 20 seconds (e.g. 15 seconds).

A muscle response to a performed PTC stimulation cycle may have PTC response pulses induced by the ST pulses of the PTC stimulation cycle.

A PTC-count parameter may be derived from a PTC muscle response, said PTC-count parameter corresponding to the number of PTC response pulses with amplitude greater than zero in the PTC muscle response. Since PTC patterns are well known in monitoring neuromuscular blockade, no further details will be provided to this respect.

FIG. 1 is a flow chart schematically illustrating automatic changes from a predefined induction status 100a to other statuses 100b, 100d in a method being performed for a patient to whom a muscle relaxant has been delivered. Induction status 100a may be initially attributed to the patient by default (e.g. after delivery of the muscle relaxant) or depending on a previous phase 1PREV.

This previous phase 1PREV may be e.g. an initial or calibration phase, examples of which may be provided in other parts of the description.

The induction status 100a may have predefined a TOF stimulation cycle with a cycle periodicity of e.g. 12 seconds. At block 1a, the method may therefore comprise waiting for 12 seconds and then, once the 12 seconds have elapsed, proceeding to block 1b. At block 1b, performance of the predefined TOF stimulation cycle may be caused along with derivation of corresponding TOF-count and TOF-ratio parameters.

The induction status 100a may also have predefined a first criterion or first set of criterions for changing the neuromuscular status. This first criterion or first set of criterions is described below with reference to blocks 1c-1f of FIG. 1.

At block 1c, a verification of whether TOF-count is less than 4 may be performed. In case of a positive result of said verification, the neuromuscular status may be changed to moderate status 100b. In case of a negative result of said verification, the method may continue to block 1d.

At block 1d, a verification of whether TOF-ratio is less than 30% may be performed. In case of a positive result of said verification, the method may proceed to block 1e. In case of a negative result of said verification, the method may continue to block 1f.

At block 1e, the method may comprise verifying whether TOF-ratio has been less than 30% during 5 minutes. In case of a positive result of said verification, the neuromuscular status may be changed to moderate status 100b. In case of a negative result of said verification, the method may loop back to block 1a for initiating a new iteration of the TOF stimulation cycle (block 1b) and verification of the first criterion or first set of criterions (blocks 1c-1f).

In certain surgical procedures, a relatively low level of neuromuscular blockade (or partial neuromuscular blockade) may be required, such that fourth TOF response pulses may have amplitude greater than zero permanently. In such circumstances, TOF-count would be equal to 4 and TOF-ratio would be greater than 0% always.

The above transition, at block 1e, from induction status 100a to moderate status 100b when TOF-ratio has been less than 30% during 5 minutes is aimed at properly monitoring said partial neuromuscular blockade. More details about partial neuromuscular blockade in the context of methods are provided in other parts of the description.

At block 1f, the method may comprise verifying whether TOF-ratio has been greater than or equal to 30% during 15 minutes. In case of a positive result of said verification, the neuromuscular status may be changed to unblocked status 100d. In case of a negative result of said verification, the method may loop back to block 1a for initiating a new iteration of the TOF stimulation cycle (block 1b) and verification of the first criterion or first set of criterions (blocks 1c-1f).

When unblocked status 100d is attributed to the patient, the method may end its execution as it may be considered that the patient's muscles are not blocked anymore.

Alternatively to the previously described TOF stimulation cycle and first criterion or first set of criterions, the transition from induction status 100a to moderate status 100b may be based on a ST stimulation cycle and a corresponding first criterion (or first set of criterions). The periodicity of said ST stimulation cycle may be of approximately 1 second, and the first criterion (or first set of criterions) may be based on the following rule.

A first counter may be increased by a single unit when ST-ratio is less than or equal to 15%. This first counter may be increased by an additional unit when ST-ratio is less than or equal to 8%. A second counter may be increased by a single unit when ST-ratio is less than or equal to 4%.

The first and second counters may be set to zero when three consecutive ST stimulations with ST-ratio greater than 15% occur. The neuromuscular blockade status may be changed to moderate status 100b when the first counter is greater than or equal to 20 and the second counter is greater than or equal to 3.

Figure 2:
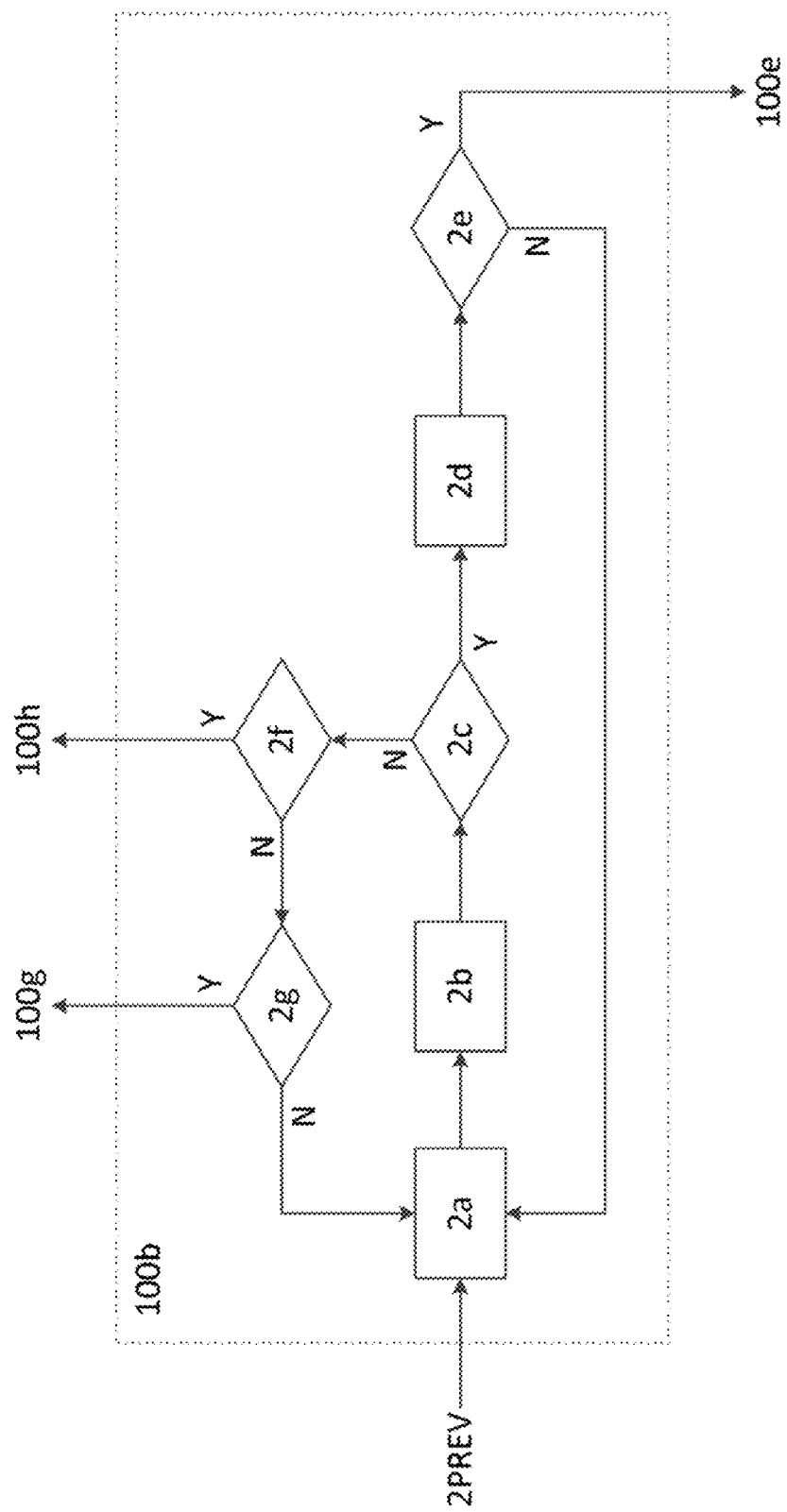
FIG. 2 is a flow chart schematically illustrating automatic changes from moderate status to other statuses in the context of a method according to the same or similar example.

FIG. 2 is a flow chart schematically illustrating automatic changes from moderate status 100b to other statuses in the same or in a similar method. Moderate status 100b may be attributed to the patient depending on a previous phase 2PREV.

This previous phase 2PREV may be the "induction phase" 100a described in relation to FIG. 1, for example. Other possible transitions to moderate status 100b are described in other parts of the description.

The moderate status 100b may have a predefined TOF stimulation cycle with a cycle periodicity of e.g. 1 minute. At block 2a, the method may therefore comprise waiting for 1 minute and then proceeding to block 2b. At block 2b, performance of the predefined TOF stimulation cycle may be caused along with derivation of corresponding TOF-count and TOF-ratio parameters.

The moderate status 100b may also have predefined a first criterion or first set of criterions for changing the neuromuscular status. This first criterion or first set of criterions is described below with reference to blocks 2c-2g of FIG. 2.

At block 2c, a verification of whether the TOF-count is equal to zero and the TOF-ratio is equal to 0% may be performed. In case of a positive result of said verification, the method may proceed to block 2d. In case of a negative result of said verification, the method may continue to block 2f.

At block 2*d*, a counter of consecutive TOF stimulations with a TOF-count equal to zero and a TOF-ratio equal to 0% may be increased and, afterwards, the method may continue to block 2*e*.

At block 2*e*, the method may comprise verifying whether the counter of consecutive TOF stimulations with TOF-count equal to zero and TOF-ratio equal to 0% is equal to 2. In case of a positive result of said verification, the neuromuscular status may be changed to deep status 100*e*. In case of a negative result of said verification, the method may loop back to block 2*a*.

At block 2*f*, a verification of whether TOF-ratio is greater than or equal to 80% may be performed. In case of a positive result of said verification, the neuromuscular status may be changed to end-of-reversion status 100*h*. In case of a negative result of said verification, the method may continue to block 2*g*.

At block 2*g*, a verification of whether TOF-ratio is greater than or equal to 4% may be performed. In case of a positive result of said verification, the neuromuscular status may be changed to reversion status 100*g*. In case of a negative result of said verification, the method may loop back to block 2*a*.

At blocks 2*f* and 2*g*, the determination is made whether the patient's muscles are becoming unblocked or have already become significantly unblocked.

Figure 3:
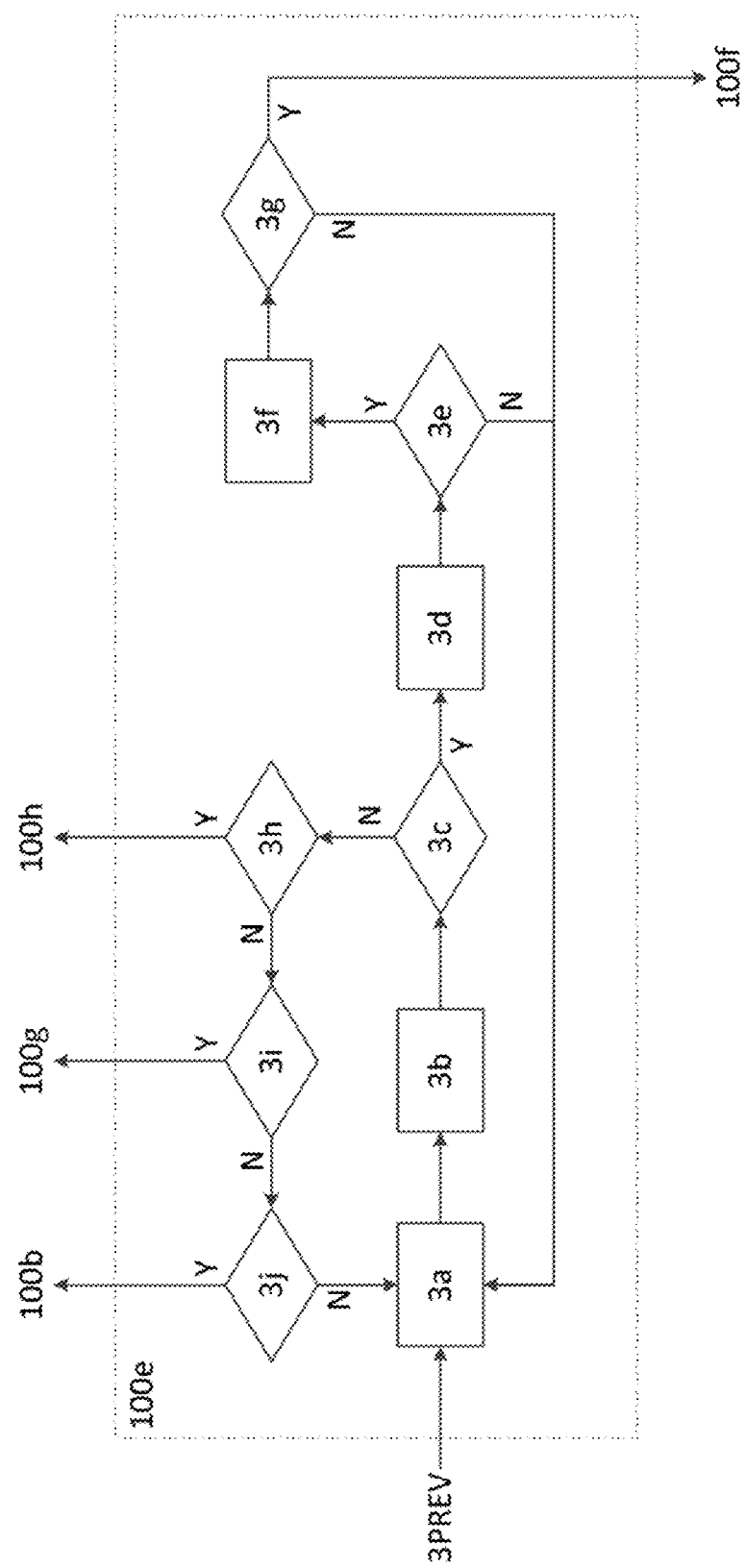
FIG. 3 is a flow chart schematically illustrating automatic changes from deep status to other statuses in the context of a method according to the same or similar example.

FIG. 3 is a flow chart schematically illustrating automatic changes from deep status 100*e* to other statuses in the same or in a similar method. Deep status 100*e* may be attributed to the patient depending on a previous phase 3PREV.

This previous phase 3PREV may be the "moderate phase" 100*b* described in relation to FIG. 2.

The deep status 100*e* may have predefined a TOF stimulation cycle with a cycle periodicity of e.g. approximately 2 minutes. At block 3*a*, the method may therefore comprise waiting for 2 minutes and then proceeding to block 3*b*. At block 3*b*, performance of the predefined TOF stimulation cycle may be caused along with derivation of corresponding TOF-count and TOF-ratio parameters.

The deep status 100*e* may also have a predefined first criterion or first set of criterions for changing the neuromuscular status. This first criterion or first set of criterions is described below with reference to blocks 3*c*-3*e* and 3*h*-3*j* of FIG. 3.

At block 3*c*, a verification of whether a TOF-count is equal to zero and a TOF-ratio is equal to 0% may be performed. In case of a positive result of said verification, the method may proceed to block 3*d*. In case of a negative result of said verification, the method may continue to block 3*h*.

At block 3*h*, a verification of whether TOF-ratio is greater than or equal to 80% may be performed. In case of a positive result of said verification, the neuromuscular status may be changed to end-of-reversion status 100*h*. In case of a negative result of said verification, the method may continue to block 3*i*.

At block 3*i*, a verification of whether TOF-ratio is greater than or equal to 7% may be performed. In case of a positive result of said verification, the neuromuscular status may be changed to reversion status 100*g*. In this sense, the blocks 3*h* and 3*i* are generally comparable to blocks 2*f* and 2*g* for a different neuromuscular blockade status.

In case of a negative result of the verification in block 3*i*, the method may continue to block 3*j*.

At block 3*j*, a verification of whether a TOF-count is greater than zero may be performed. In case of a positive result of said verification, the neuromuscular status may be changed to moderate status 100*b*. In case of a negative result of said verification, the method may loop back to block 3*a*.

At block 3*d*, a counter of consecutive TOF stimulations with TOF-count equal to zero and TOF-ratio equal to 0% may be increased and, afterwards, the method may continue to block 3*e*.

At block 3*e*, the method may comprise verifying whether the counter of consecutive TOF stimulations with TOF-count equal to zero and TOF-ratio equal to 0% is equal to 3. In case of a positive result of said verification, the method may continue to block 3*f*. In case of a negative result of said verification, the method may loop back to block 3*a*.

The deep status 100*e* may further have predefined a PTC stimulation cycle with a cycle periodicity of e.g. approximately 6 minutes. At block 3*f*, the method may comprise waiting for 12 seconds after TOF stimulation and then causing performance of the predefined PTC stimulation cycle along with derivation of corresponding PTC-count parameter.

The deep status 100*e* may also have predefined a second criterion or second set of criterions for changing the neuromuscular status. This second criterion (or second set of criterions) is described below with reference to block 3*g* of FIG. 3.

At block 3*g*, a verification of whether PTC-count is less than or equal to 4 may be performed. In case of a positive result of said verification, the neuromuscular status may be changed to intense status 100*f*. In case of a negative result of said verification, the method may loop back to block 3*a*.

Figure 4:
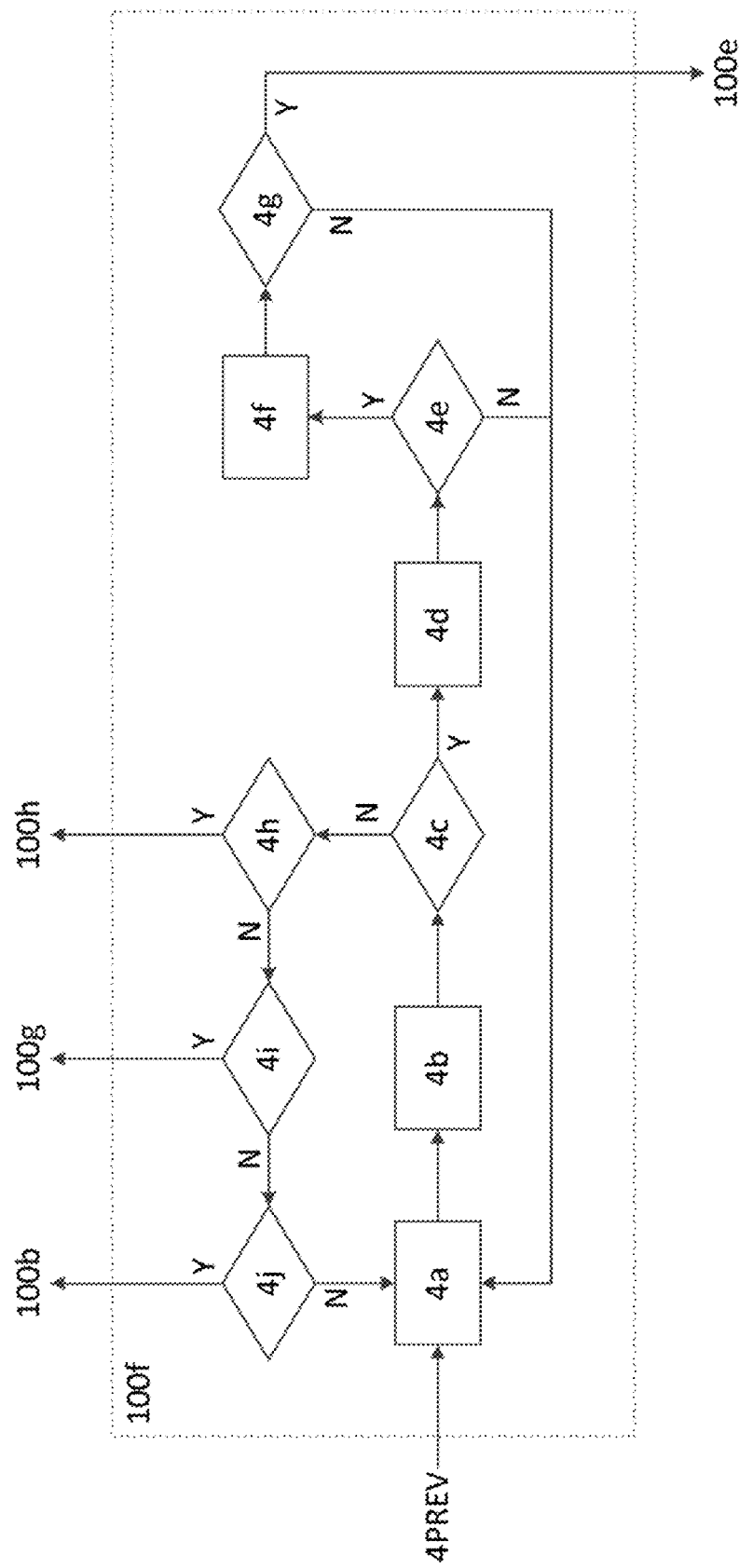
FIG. 4 is a flow chart schematically illustrating automatic changes from intense status to other statuses in the context of a method according to the same or similar example.

FIG. 4 is a flow chart schematically illustrating automatic changes from intense status 100*f* to other statuses in the same or in a similar method. Intense status 100*f* may be attributed to the patient depending on a previous phase 4PREV.

This previous phase 4PREV may be the "deep phase" 100*e* described in relation to FIG. 3, for example.

The intense status 100*f* may have a predefined TOF stimulation cycle with a cycle periodicity of e.g. approximately 2 minutes. At block 4*a*, the method may therefore comprise waiting for 2 minutes and then proceeding to block 4*b*. At block 4*b*, performance of the predefined TOF stimulation cycle may be caused along with derivation of corresponding TOF-count and TOF-ratio parameters.

The intense status 100*f* may also have predefined a first criterion or first set of criterions for changing the neuromuscular status. This first criterion (or first set of criterions) is described below with reference to blocks 4*c*-4*e* and 4*h*-4*j* of FIG. 4.

At block 4*c*, a verification of whether a TOF-count is equal to zero and a TOF-ratio is equal to 0% may be performed. In case of a positive result of said verification, the method may proceed to block 4*d*. In case of a negative result of said verification, the method may continue to block 4*h*.

At block 4*h*, a verification of whether TOF-ratio is greater than or equal to 80% may be performed. In case of a positive result of said verification, the neuromuscular status may be changed to end-of-reversion status 100*h*. In case of a negative result of said verification, the method may continue to block 4*i*. This block is thus comparable to blocks 3*h* and 2*f*.

At block 4*i*, a verification of whether TOF-ratio is greater than or equal to 10% may be performed. In case of a positive result of said verification, the neuromuscular status may be changed to reversion status 100*g*. In case of a negative result of said verification, the method may continue to block 4*j*. This block is thus generally comparable to block 3*i*.

At block 4*j*, a verification of whether TOF-count is greater than zero may be performed. In case of a positive result of said verification, the neuromuscular status may be changed to moderate status 100*b*. In case of a negative result of said verification, the method may loop back to block 4*a*. This block is thus comparable to block 3*j*.

At block 4*d*, a counter of consecutive TOF stimulations with TOF-count equal to zero and TOF-ratio equal to 0% may be increased and, afterwards, the method may continue to block 4*e*.

At block 4*e*, the method may comprise verifying whether the counter of consecutive TOF stimulations with a TOF-count equal to zero and a TOF-ratio equal to 0% is equal to 3. In case of a positive result of said verification, the method may continue to block 4*f*. In case of a negative result of said verification, the method may loop back to block 4*a*.

The intense status 100*f* may further have predefined a PTC stimulation cycle with a cycle periodicity of e.g. approximately 6 minutes. At block 4*f*, the method may comprise waiting for 12 seconds after TOF stimulation and then causing performance of the predefined PTC stimulation cycle along with derivation of corresponding PTC-count parameter.

The intense status 100*f* may also have predefined a second criterion or second set of criterions for changing the neuromuscular status. This second criterion (or second set of criterions) is described below with reference to block 4*g* of FIG. 4.

At block 4*g*, a verification of whether FTC-count is greater than or equal to 8 may be performed. In case of a positive result of said verification, the neuromuscular status may be changed to deep status 100*e*. In case of a negative result of said verification, the method may loop back to block 4*a*.

Figure 5:
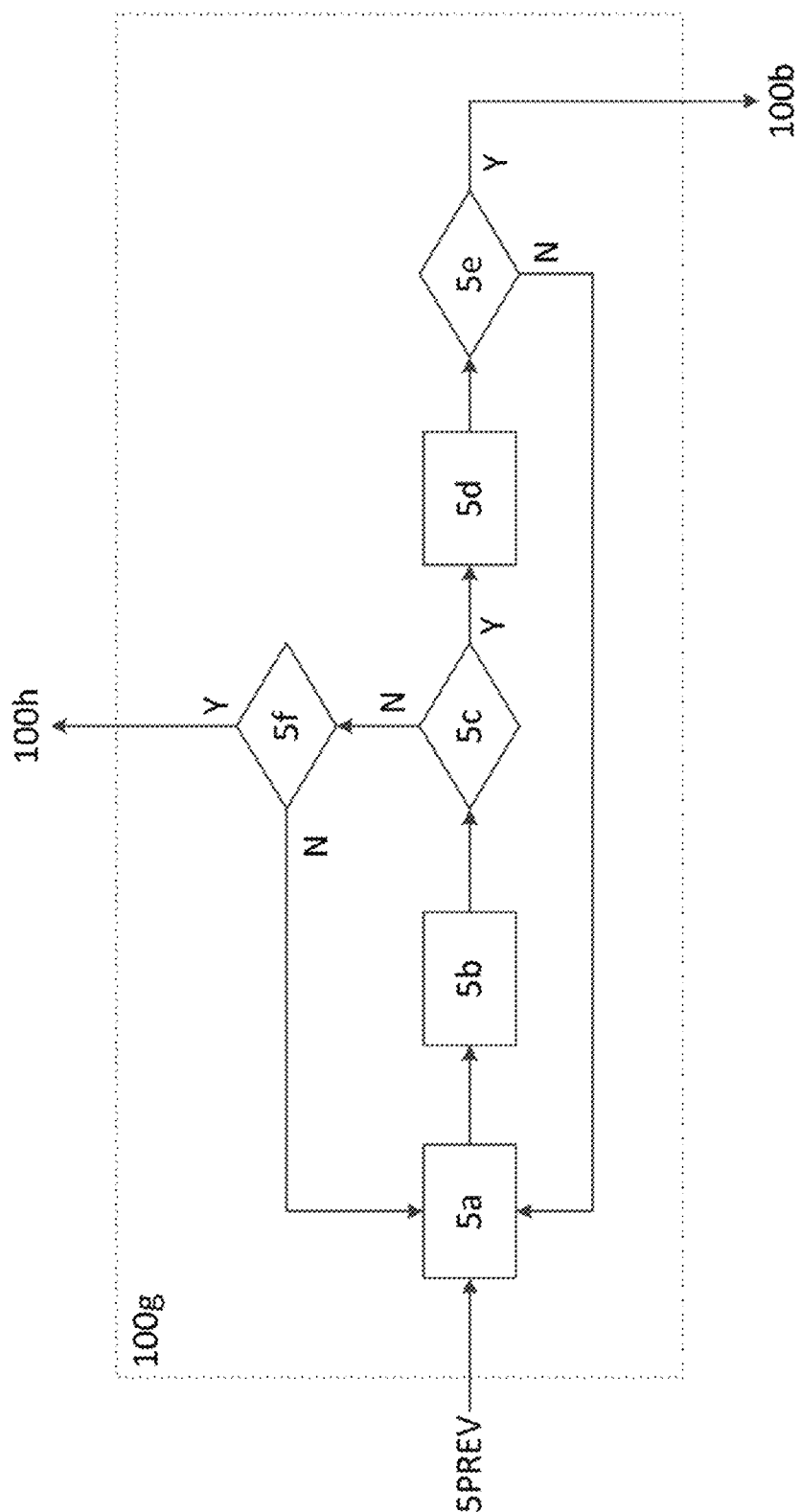
FIG. 5 is a flow chart schematically illustrating automatic changes from reversion status to other statuses in the context of a method according to the same or similar example.

FIG. 5 is a flow chart schematically illustrating automatic changes from reversion status 100*g* to other statuses in the same or in a similar method. Reversion status 100*g* may be attributed to the patient depending on a previous phase 5PREV.

This previous phase 5PREV may be, for example, the "intense phase" 100*f* described in relation to FIG. 4. Other possible transitions to reversion status 100*g* may be described in other parts of the description.

The reversion status 100*g* may have a predefined TOF stimulation cycle with e.g. a cycle periodicity of e.g. 1 minute. At block 5*a*, the method may therefore comprise waiting for 1 minute and then, proceeding to block 5*b*. At block 5*b*, performance of the predefined TOF stimulation cycle may be caused along with derivation of corresponding TOF-count and TOF-ratio parameters.

The reversion status 100*g* may also have predefined first criterion(s) for changing the neuromuscular status. This first criterion(s) is described below with reference to blocks 5*c*-5*f* of FIG. 5.

At block 5*c*, a verification of whether a TOF-count is less than 4 may be performed. In case of a positive result of said verification, the method may proceed to block 5*d*. In case of a negative result of said verification, the method may continue to block 5*f*.

At block 5*d*, a counter of consecutive TOF stimulations with TOF-count less than 4 may be increased and, afterwards, the method may continue to block 5*e*.

At block 5*e*, the method may comprise verifying whether the counter of consecutive TOF stimulations with TOF-count less than 4 is equal to 2. In case of a positive result of said verification, the neuromuscular status may be changed to moderate status 100*b*. In case of a negative result of said verification, the method may loop back to block 5*a*.

At block 5*f*, the method may comprise verifying whether a TOF-ratio is greater than or equal to 80%. In case of a positive result of said verification, the neuromuscular status may be changed to end-of-reversion status 100*h*. Again, it may thus be considered that the patient's muscles are not blocked anymore. In case of a negative result of said verification, the method may loop back to block 5*a*.

Figure 6:
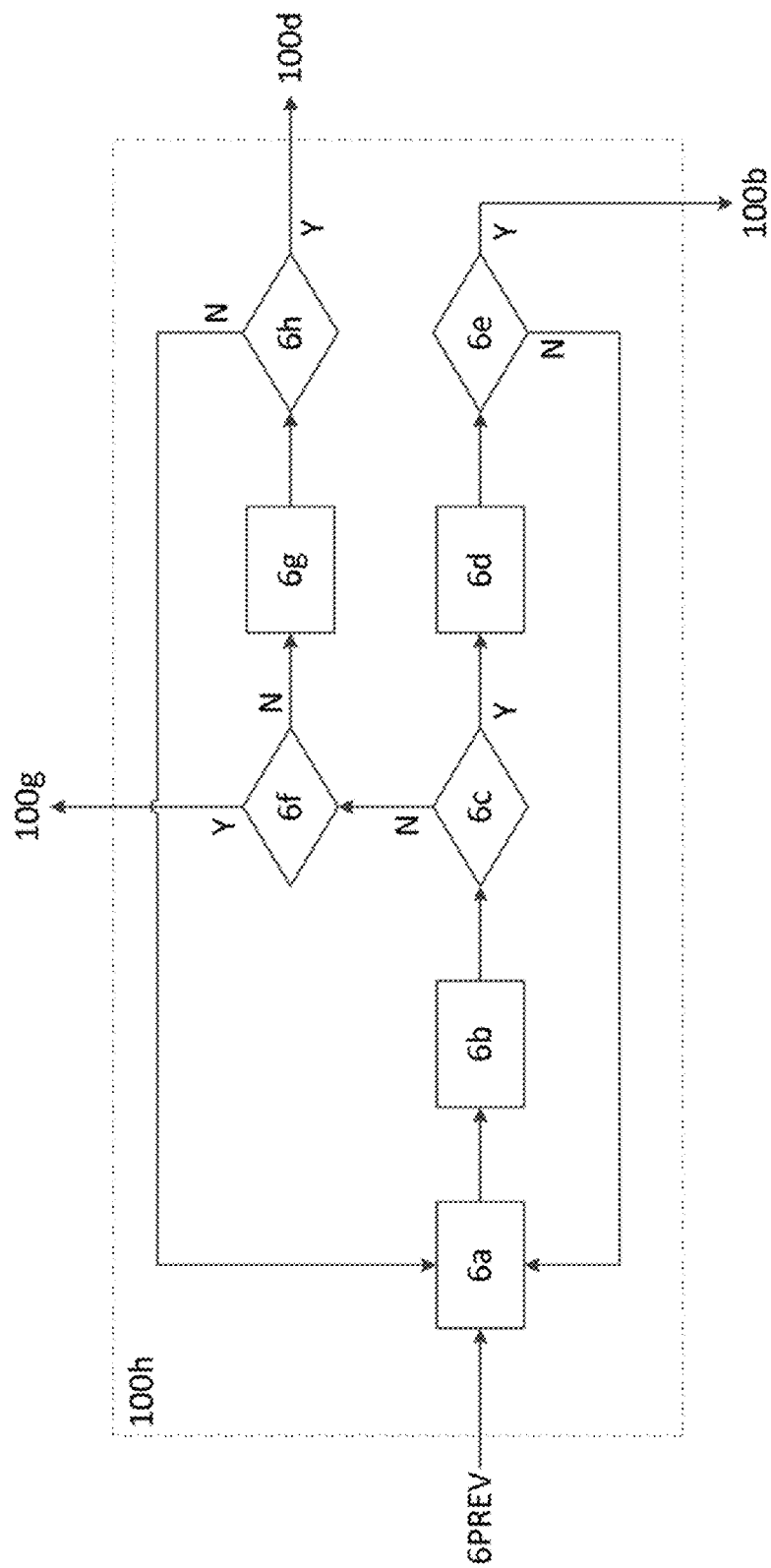
FIG. 6 is a flow chart schematically illustrating automatic changes from end-of-reversion status to other statuses in the context of a method according to the same or similar example.

FIG. 6 is a flow chart schematically illustrating automatic changes from end-of-reversion status 100*h* to other statuses in the same or in a similar method. End-of-reversion status 100*h* may be attributed to the patient depending on a previous phase 6PREV.

This previous phase 6PREV may be, for example, the "reversion phase" 100*g* described in relation to FIG. 5. Other possible transitions to end-of-reversion status 100*g* may be described in other parts of the description.

The end-of-reversion status 100*h* may have a predefined TOF stimulation cycle with a cycle periodicity of e.g. approximately 30 seconds. At block 6*a*, the method may therefore comprise waiting for 30 seconds and proceeding to block 6*b*. At block 6*b*, performance of the predefined TOF stimulation cycle may be caused along with derivation of corresponding TOF-count and TOF-ratio parameters.

The end-of-reversion status 100*h* may also have predefined first criterion(s) for changing the neuromuscular status. These first criterions are described below with reference to blocks 6*c*-6*h* of FIG. 6.

At block 6*c*, a verification of whether a TOF-count is less than 4 may be performed. In case of a positive result of said verification, the method may proceed to block 6*d*. In case of a negative result of said verification, the method may continue to block 6*f*.

At block 6*d*, a counter of consecutive TOF stimulations with TOF-count less than 4 may be increased and, afterwards, the method may continue to block 6*e*.

At block 6*e*, the method may comprise verifying whether the counter of consecutive TOF stimulations with TOF-count less than 4 is equal to 2. In case of a positive result of said verification, the neuromuscular status may be changed to moderate status 100*b*. In case of a negative result of said verification, the method may loop back to block 6*a*.

At block 6*f*, a verification of whether TOF-ratio is less than 60% may be performed. In case of a positive result of said verification, the neuromuscular status may be changed to reversion status 100*g*. In case of a negative result of said verification, the method may continue to block 6*g*.

At block 6*g*, a weighted score may be applied by using a weighted counter that has been set to zero at the beginning of the "end-of-reversion phase" 100*h*, i.e. prior to the first execution of block 6*a*. This weighted counter may be increased by one if TOF-ratio 91% and TOF-ratio 94%, or increased by two if TOF-ratio 95% and TOF-ratio 98%, or increased by three if TOF-ratio 99%. Once the weighted counter has been updated, the method may continue to block 6*h*.

At block 6*h*, a verification of whether the weighted counter is greater than or equal to 5 may be performed. In case of a positive result of said verification, the neuromuscular status may be changed to unblocked status 100*d*. In case of a negative result of said verification, the method may loop back to block 6*a*. When unblocked status 100*d* is attributed to the patient, the method may end its execution.

Figure 7:
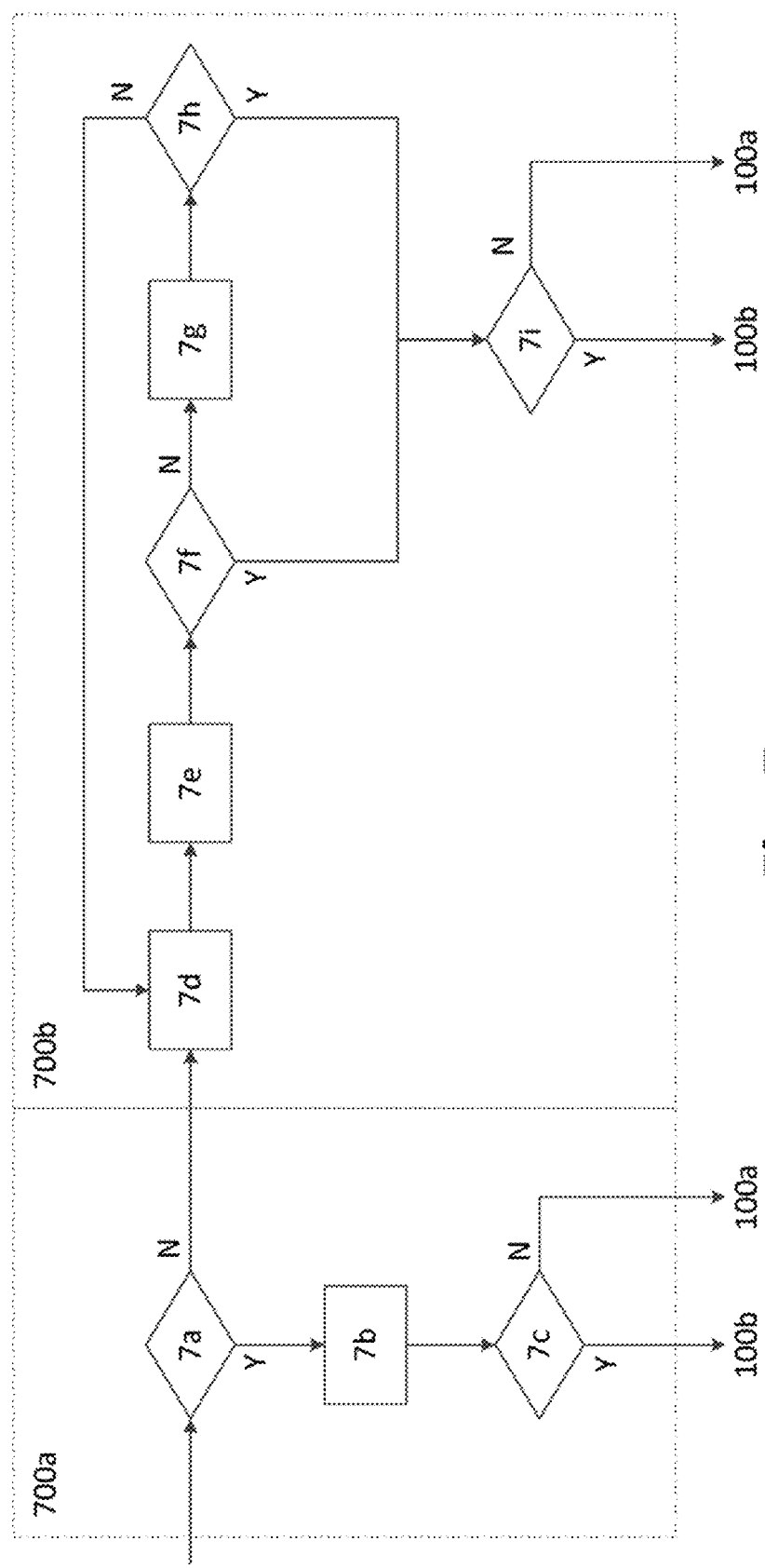
FIG. 7 is a flow chart schematically illustrating initial and calibration phases in the context of a method according to the same or similar example.

FIG. 7 is a flow chart schematically illustrating an initial phase 700*a* and a calibration phase 700*b* which may be employed prior to the methods for determining a neuromuscular blockade status as hereinbefore described.

The initial phase (or sub-method) 700a may start at block 7a, wherein the initial sub-method 700a may comprise verifying whether a muscle response of reference has been determined for the patient. In case of a positive result of said verification, a transition to block 7b may be performed.

In case of a negative result of said verification, the calibration phase (or sub-method) 700b may be started at block 7d.

At block 7b, performance of an initial TOF stimulation cycle may be caused along with determination of corresponding TOF-count parameter.

At block 7c, a verification of whether TOF-count is less than 4 may be carried out. In case of a positive result of said verification, moderate status 100b may be initially attributed to the patient and, therefore, a sub-method identical or similar to the one illustrated by FIG. 2 may be started. In case of a negative result of said verification, induction status 100a may be attributed to the patient and, therefore, a sub-method identical or similar to the one illustrated by FIG. 1 may be started.

The calibration sub-method 700b may have predefined a TOF stimulation cycle with a cycle periodicity of 12 seconds. At block 7d, the calibration sub-method 700b may therefore comprise waiting for 12 seconds and then, once elapsed said 12 seconds, proceeding to block 7e.

At block 7e, performance of the predefined TOF stimulation cycle may be caused along with derivation of corresponding TOF-count parameter.

At block 7f, the calibration sub-method 700b may comprise verifying whether a muscle response of reference has been determined for the patient. In case of a positive result of said verification, the calibration sub-method 700b may continue to block 7i. In case of a negative result of said verification, the calibration sub-method 700b may proceed to block 7g.

At block 7g, a counter of performed TOF stimulations may be increased and, afterwards, the calibration sub-method 700b may continue to block 7h.

At block 7h, a verification of whether the counter of performed TOF stimulations is equal to 4 may be carried out. In case of a positive result of said verification, the calibration sub-method 700b may continue to block 7i. In case of a negative result of said verification, the calibration sub-method 700b may loop back to block 7d.

At block 7i, a verification of whether TOF-count is less than 4 may be performed. In case of a positive result of said verification, moderate status 100b may be attributed to the patient and, therefore, a sub-method identical or similar to the one illustrated by FIG. 2 may be started. In case of a negative result of said verification, induction status 100a may be attributed to the patient and, therefore, a sub-method identical or similar to the one illustrated by FIG. 1 may be started.

The muscle response of reference may be determined either manually (i.e. outside the automatic initial and calibration sub-methods 700a, 700b) or automatically (i.e. by the calibration sub-method 700b).

The muscle response of reference may be determined manually by causing performance of a TOF stimulation cycle and subsequently deriving the muscle response of reference from the performed TOF stimulation.

FIG. 7 schematically shows that if the muscle response of reference has not been determined before, it may be automatically determined by the calibration sub-method 700b based on causing performance of up to 4 TOF stimulations with a periodicity of 12 seconds.

The muscle response of reference may be required to be greater than a minimum amplitude and to have a TOF-count parameter equal to 4. If this were not the case, the patient would be relaxed (i.e. affected by muscle relaxant(s)) and the muscle response of reference would be useless.

Determining the muscle response (either manually or automatically) may further comprise determining an optimum stimulation (TOF) current for the patient.

In clinical/surgical practice, the use of new drugs, such as e.g. Sugammadex, allowing a faster reversion of neuromuscular blockade is growing increasingly. These new drugs typically also facilitate the use of intense blockades if required.

FIGS. 1-7 illustrate sub-methods of methods for determining a neuromuscular blockade status a patient assuming that standard drugs are being used for causing either neuromuscular blockade or reversion of the neuromuscular blockade. The expression "standard drugs" is used herein to indicate drugs that are currently normally used, i.e. drugs which are not of the type described above i.e. for "faster reversion".

Figure 8:
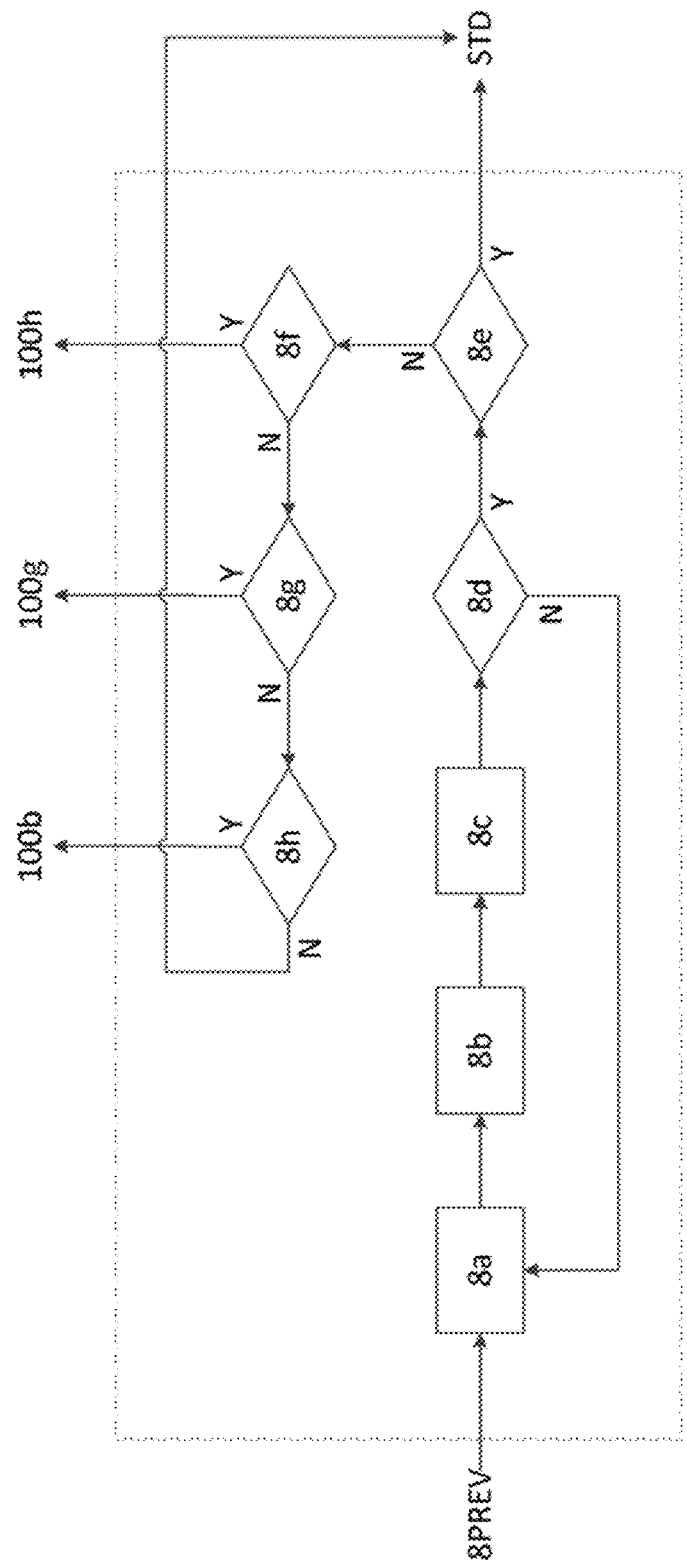
FIG. 8 is a flow chart schematically illustrating a sub-method of a method according to another example assuming that a "faster reversion" drug has been delivered to the patient.

FIG. 8 is a flow chart schematically illustrating a sub-method of a method according to another example assuming that a "faster reversion" drug has been delivered to the patient.

This sub-method may be triggered when previous conditions 8PREV are fulfilled. A previous condition may comprise e.g. activation of an indicator representing that a "faster reversion" drug is being used. This activation may be provided by e.g. an anaesthesiologist (or similar profile) through suitable means for data entry. If this indicator is activated, the method may trigger this "faster reversion" sub-method from e.g. deep status 100e (FIG. 3) or intense status 100f (FIG. 4) depending on respective first and/or second criterion(s) for changing the neuromuscular blockade status.

This "faster reversion" sub-method may have predefined a TOF stimulation cycle with a cycle periodicity of 30 seconds. At block 8a, the sub-method may therefore comprise waiting for 30 seconds and then, once elapsed said 30 seconds, proceeding to block 8b. At block 8b, performance of the predefined TOF stimulation cycle may be caused along with derivation of corresponding TOF-count and TOF-ratio parameters.

At block 8c, a counter of performed TOF stimulations may be increased and, afterwards, the sub-method may continue to block 8d.

At block 8d, the sub-method may comprise verifying whether the counter of performed TOF stimulations is equal to 4. In case of a positive result of said verification, the sub-method may proceed to block 8e. In case of a negative result of said verification, the method may loop back to block 8a.

At block 8e, a verification of whether TOF-count is equal to zero and TOF-ratio is equal to 0% may be performed. In case of a positive result of said verification, the sub-method may return to a standard method STD (assuming that a standard drug is being used). In case of a negative result of said verification, the method may continue to block 8f.

At block 8f, a verification of whether TOF-ratio is greater than or equal to 80% may be performed. In case of a positive result of said verification, the neuromuscular status may be changed to end-of-reversion status 100h. In case of a negative result of said verification, the method may continue to block 8g.

At block 8g, a verification of whether TOF-ratio is greater than or equal to 7% may be performed. In case of a positive result of said verification, the neuromuscular status may be changed to reversion status 100g. In case of a negative result of said verification, the method may continue to block 8h.

At block 8h, a verification of whether TOF-count is greater than zero may be performed. In case of a positive result of said verification, the neuromuscular status may be changed to moderate status 100b. In case of a negative result of said verification, the method may return to the standard method STD.

In relation to monitoring of partial neuromuscular blockade (see FIG. 1 and descriptions about block 1e), some particularities may be present in examples of the method for carrying out said special monitoring of partial neuromuscular blockade.

For example, moderate status 100b may have its first criterion or first set of criterions adapted to store the minimum TOF-ratio measured and to transition to other statuses according to particular rules for monitoring partial neuromuscular blockade.

For example, a particular rule for partial neuromuscular blockade may comprise transitioning to reversion status when TOF-ratio is greater than or equal to 50%, or when TOF-ratio is greater than or equal to the result of adding the (stored) minimum TOF-ratio and 25%.

A further particular rule for partial neuromuscular blockade may comprise transitioning from reversion status to moderate status when four consecutive TOF stimulations produce TOF-ratio less than 30%.

A still further particular rule for partial neuromuscular blockade may comprise transitioning from end-of-reversion status to moderate status when four consecutive TOF stimulations produce TOF-ratio less than 30%.

Figure 9:
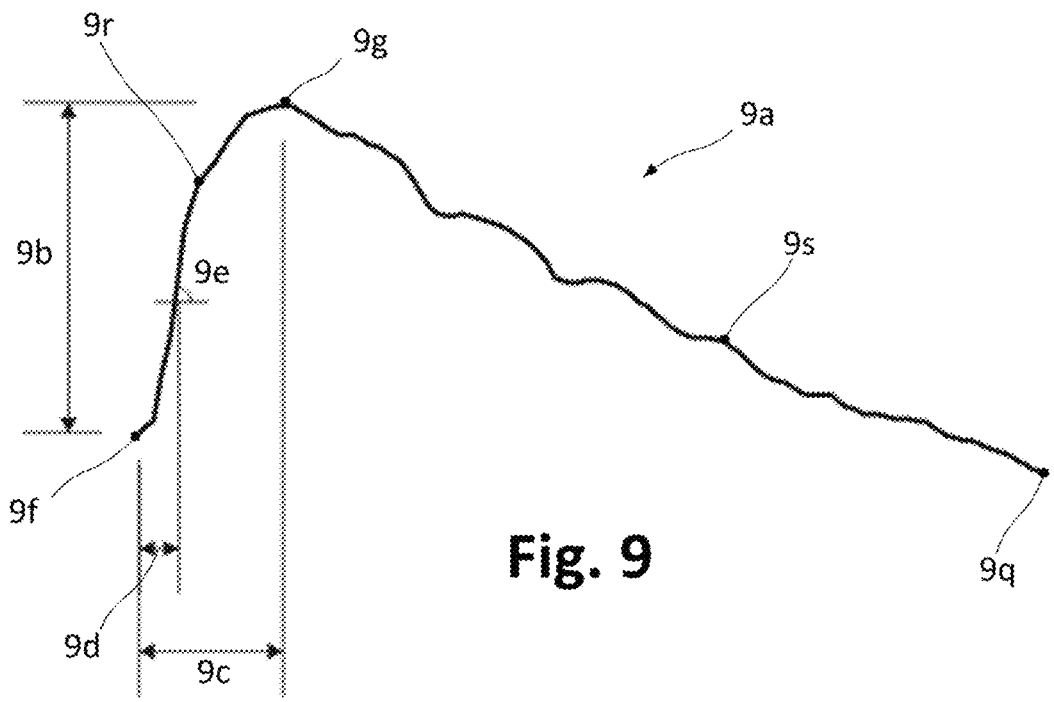
FIG. 9 schematically shows a pressure pulse due to a patient's heartbeat and related parameters, the pressure pulse being obtained through a pressure cuff.

FIG. 9 schematically shows a pressure pulse 9a due to a patient's heartbeat and some parameters related to said pulse 9a. The pressure pulse 9a may have been obtained through a pressure cuff applied around a patient's limb (e.g. arm). In particular, this pressure pulse 9a may represent how pressure varies over time inside the cuff as a result of patient's heartbeat.

The heartbeat pulse 9a may have a start point 9f, an upward slope 9r, a peak 9g, a downward slope 9s, and an end 9q. FIG. 9 illustrates that a heartbeat pulse 9a may have an amplitude 9b, which may be defined as the pressure variation in the heartbeat pulse 9a between the pressure at start point 9f and the peak 9g.

The start 9f of the heartbeat pulse 9a may be defined as the point at which the heartbeat pulse 9a substantially starts to rise from a pressure variation substantially equal to zero. In other words, the start 9f of the heartbeat pulse 9a may be defined as the point at which the upward slope 9r of the heartbeat pulse 9a substantially starts.

The end 9q of the heartbeat pulse 9a may be defined as the point at which the heartbeat pulse 9a substantially ends to drop to a pressure variation substantially equal to zero, i.e. the point at which the downward slope 9s of the heartbeat pulse 9a substantially ends.

FIG. 9 further shows that a heartbeat pulse 9a may also have associated with it a rising time 9c, a maximum derivative 9e, and a time of the maximum derivative 9d. The rising time 9c may be defined as the time elapsed between the start 9f and the peak 9g of the heartbeat pulse 9a.

The maximum derivative 9e may be defined as the maximum inclination of a tangent line to the heartbeat pulse 9a at any point of the upward slope 9r. The time of the maximum derivative 9d may be defined as the time elapsed between the start 9f of the pulse 9a and the point of the maximum derivative 9e.

Figure 10:
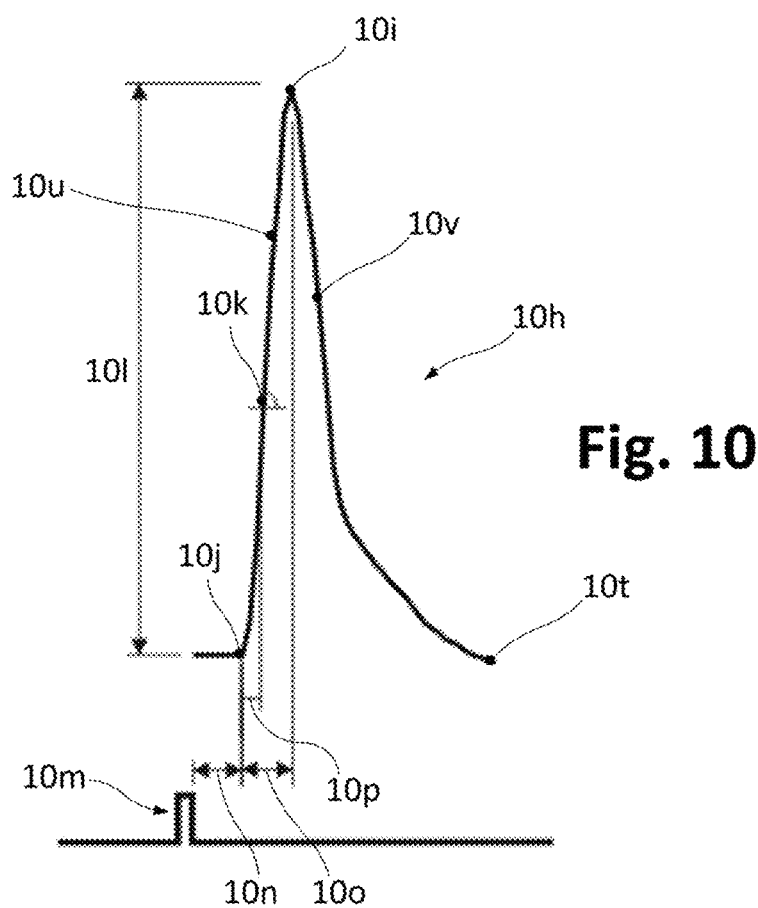
FIG. 10 schematically shows a muscle response pulse due to an electro stimulation pulse and related parameters, the muscle response pulse being obtained through a pressure cuff.

FIG. 10 schematically shows a muscle response pulse 10h induced by an electro stimulation pulse 10m, and some parameters related to said pulse 10h. The muscle response pulse 10h may have been obtained through a pressure cuff applied around a patient's limb (e.g. arm). In particular, this muscle response pulse 10h represents how pressure varies over time inside the cuff as a muscle reaction to the electro stimulation pulse 10m.

Similarly to the heartbeat pulse 9a (of FIG. 9), the muscle response pulse 10h (of FIG. 10) may be defined or described by an amplitude 10l (i.e. difference between pressure at starting point 10j and peak 10i), an upward slope 10u, the peak 10i, a downward slope 10v, an end point 10t, a rising time 10o, a maximum derivative 10k, and time until the maximum derivative 10p.

FIG. 10 shows a further parameter which is specific for this type of pulses 10h and may be called herein "stimulation-response" time 10n. This stimulation-response time 10n may be defined as the time elapsed between the electro stimulation pulse 10m that induces the muscle response pulse 10h and the start 10j of the muscle response pulse 10h itself.

Figure 11:
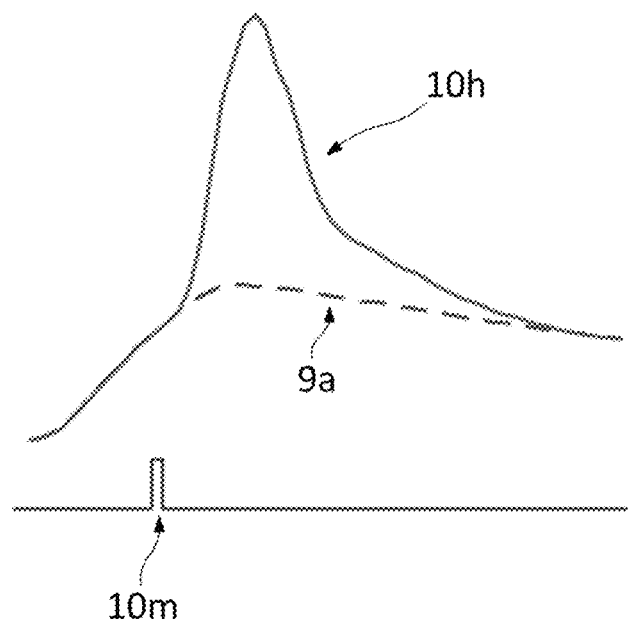
FIGS. 11 and 12 schematically shows respective views of a muscle response pulse due to an electro stimulation pulse and a heartbeat pulse interfering with the muscle response pulse, both pulses being obtained through a pressure cuff.
Figure 12:
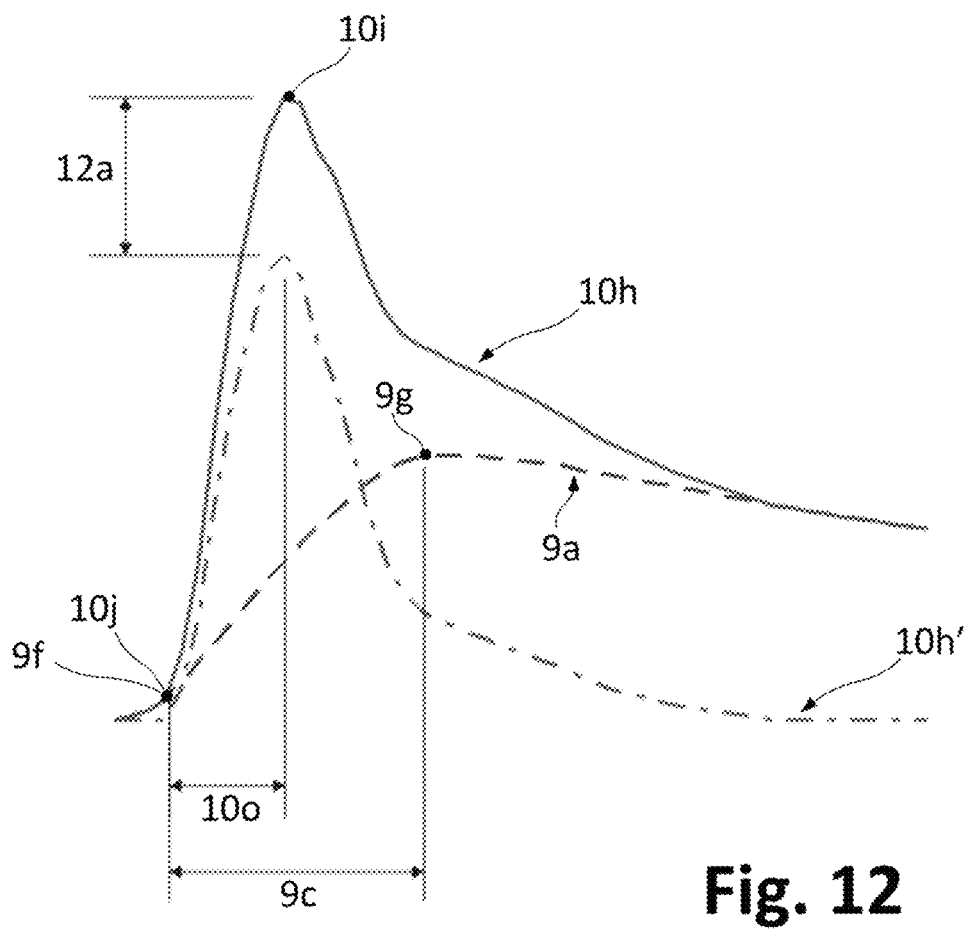

FIGS. 11 and 12 schematically show respective views of a measured muscle response pulse 10h induced by an electro stimulation pulse 10m, and a heartbeat pulse 9a interfering with the muscle response pulse 10h. Both pulses 10h, 9a may have been obtained through a pressure cuff as explained in other parts of the description.

FIG. 12 further shows an adjusted muscle response pulse 10h' which may result from performing a method for determining an "adjusted" or "filtered" muscle response 10h'. The term "filtered" or "adjusted" is used herein to indicate that the measured muscle response 10h is filtered or adjusted (by the method) in such a way that interferences due to heartbeat(s) 9a are at least partially eliminated resulting in the adjusted muscle response pulse 10h'.

FIG. 12 also shows an error 12a in the amplitude of the measured muscle response pulse 10h due to its coupling with the heartbeat pulse 9a. This error 12a may be at least partially eliminated by performing a muscle-response correction method, which may produce the adjusted muscle response 10h' without at least part of said error 12a. Details about examples of correction methods are provided in other parts of the description.

Figure 13:
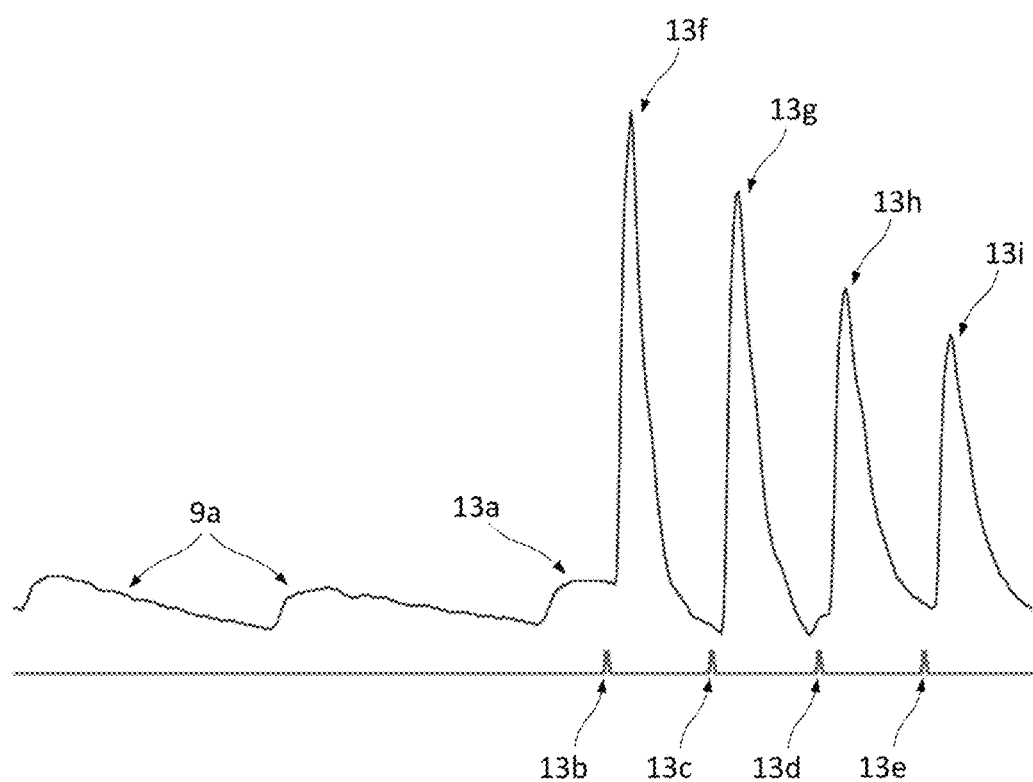
FIG. 13 schematically shows a sequence of heartbeat pulses and a muscle response to a TOF stimulation, both the heartbeat pulses and muscle response pulses being obtained through a pressure cuff.

FIG. 13 schematically shows a sequence of heartbeat pulses 9a, 13a and a muscle response 13f-13i to a TOF stimulation 13b-13e. Both the heartbeat pulses 9a, 13a and the muscle response pulses 13f-13i may have been obtained through a pressure cuff as explained in other parts of the description.

FIG. 13 shows that muscle response pulses 13f-13i are induced by TOF stimulation pulses 13b-13e respectively. This Figure also shows that some heartbeat pulses 9a occurring before the electro-stimulation do not cause any interference in muscle response pulses 13f-13i. However, other heartbeat pulses 13a occurring substantially at the same time as the electro-stimulation may interfere in muscle response pulses 13f-13i.

Figure 14:
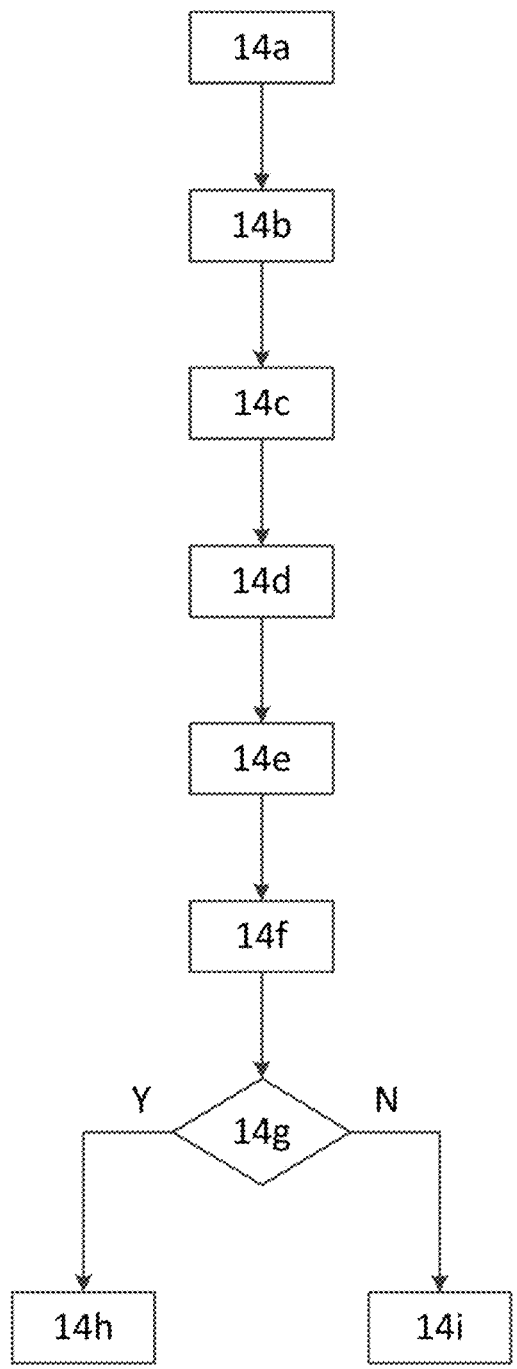
FIG. 14 is a flow chart schematically illustrating a method of determining a muscle response to an electro-stimulation, according to exam pies.

FIG. 14 is a flow chart schematically illustrating a method of determining a muscle response to an electro-stimulation in a patient, according to examples. For the sake of understanding, reference signs of FIGS. 9 to 13 may be used in following descriptions about FIG. 14.

At block 14*a*, the end 9*q* of a heartbeat 9*a* of the patient may be determined.

At block 14*b*, a first electro-stimulation pulse 13*b* may be generated and, subsequently, one or more further electro-stimulation pulses 13*c*-13*e*. The first electro-stimulation pulse 13*b* may be generated substantially at the end 9*q* of the heartbeat 9*a*.

At block 14*c*, the muscle response may be determined in the form of a pressure wave representing how pressure varies over time in a pressure cuff as a muscle reaction to the electro-stimulation. The pressure wave may comprise first and further pressure pulses 13*f*-13*i* caused by the first and further electro-stimulation pulses 13*b*-13*e* respectively.

An aspect of causing generation of the first electro-stimulation pulse 13*b* substantially at the end 9*q* of the heartbeat 9*a* may be that the first pressure pulse 13*f* may be substantially free of interference(s) with patient's heartbeat. This may thus permit taking the first pressure pulse 13*f* (induced by first electro-stimulation pulse 13*b*) as a model (or reference) for adjusting the further pressure pulses 13*g*-13*i* (provoked by further electro-stimulation pulses 13*c*-13*e*).

At block 14*d*, a first characteristic indicative of the shape of the upward slope 10*u* of the first pressure pulse 13*f* may be determined.

At block 14*e*, the first characteristic may be determined for each of the further pressure pulses 13*g*-13*i*.

At block 14*f*, the method may comprise determining, for each of the further pressure pulses 13*g*-13*i*, a deviation between the first characteristic of the further pressure pulse 13*g*-13*i* and the first characteristic of the first pressure pulse 13*f*.

At block 14*g*, a verification of whether the deviation exceeds a deviation threshold may be performed. In case of a positive result of said verification, a transition to block 14*h* may be carried out. In case of a negative result of said verification, a progression to block 14*i* may be performed. The deviation threshold may be in a range of 10%-20%, preferably equal to 15%.

At block 14*h*, each further pressure pulse 13*g*-13*i* may be adjusted based on either a first assumption or a second assumption.

The first assumption may presume that the time 10*o* until peak 10*i* of the further pressure pulse 13*g*-13*i* is measured correctly (i.e. not significantly influenced by a coinciding heart pulse) and that the shape of its upward slope 10*u* can be described by the first characteristic of the first pressure pulse 13*f*.

The second assumption may presume that the time 10*o* until peak 10*i* of the further pressure pulse 13*g*-13*i* is measured correctly and that the shape of its upward slope 10*u* can be described by substantially subtracting a heartbeat pulse of reference 9*a* from the measured further pressure pulse 13*g*-13*i*. In this case, there is an implicit assumption that the pressure pulse caused by heartbeat and the pressure pulse caused by electro-stimulation are substantially simultaneous.

At block 14*i*, each further pressure pulse 13*g*-13*i* may be adjusted based on that the time 10*o* until peak 10*i* of the further pressure pulse 13*g*-13*i* is measured correctly and that the shape of its upward slope 10*u* can be described by the first characteristic of the first pressure pulse 13*f*.

The first characteristic of the pressure pulses 13*f*-13*i* may be determined, at blocks 14*d* and 14*e*, depending on the amplitude 10*l* of the pressure pulse 13*f*-13*i* and the maximum derivative 10*k* of the upward slope 10*u* of the pressure pulse 13*f*-13*i*.

In particular, the first characteristic of the pressure pulse 13*f*-13*i* may be determined, at blocks 14*d* and 14*e*, based on the following formula:

$$C(\text{pulse}) = \frac{A(\text{pulse})}{d_{max}(\text{pulse})}$$

wherein: C(pulse) is the first characteristic of the pressure pulse 13*f*-13*i*, A(pulse) is the amplitude 10*l* of the pressure pulse 13*f*-13*i*, and $d_{max}$(pulse) is the maximum derivative 10*k* of the upward slope 10*u* of the pressure pulse 13*f*-13*i*.

The result of dividing the amplitude 10*l* by the maximum derivative 10*k* of the pulse 13*f*-13*i* conceptually represents the time until peak if the pressure pulse had a slope equal to the maximum derivative. Hence, the calculated first characteristic may be considered as a parameter representative of the shape of the corresponding pulse 13*f*-13*i*. Alternatively, other parameters and/or other mathematical relations between them could be considered for this aim.

Adjusting the further pressure pulse 13*g*-13*i* may comprise, at block 14*i*, adjusting the amplitude 10*l* of the further pressure pulse 13*g*-13*i* based on the following formula:

$$A_{adjusted}(\text{further\_pulse}) = C(\text{first\_pulse}) \times d_{max}(\text{further\_pulse})$$

wherein: $A_{adjusted}$(further_pulse) is the adjusted amplitude of the further pressure pulse 13*g*-13*i*, C(first_pulse) is the first characteristic of the first pressure pulse 13*f*, and $d_{max}$(further_pulse) is the maximum derivative 10*k* of the upward slope 10*u* of the further pressure pulse 13*g*-13*i*.

The result of multiplying the maximum derivative 10*k* of the further pressure pulse 13*g*-13*i* by the result of dividing the amplitude 10*l* by the maximum derivative 10*k* of the first pressure pulse 13*f* conceptually represents that the time until peak of a further pulse has been measured correctly (because the pressure variation of a pulse caused by a heartbeat is much smaller than the pressure variation caused by electro-stimulation), but that the amplitude was influenced by the presence of the heartbeat.

Figure 15:
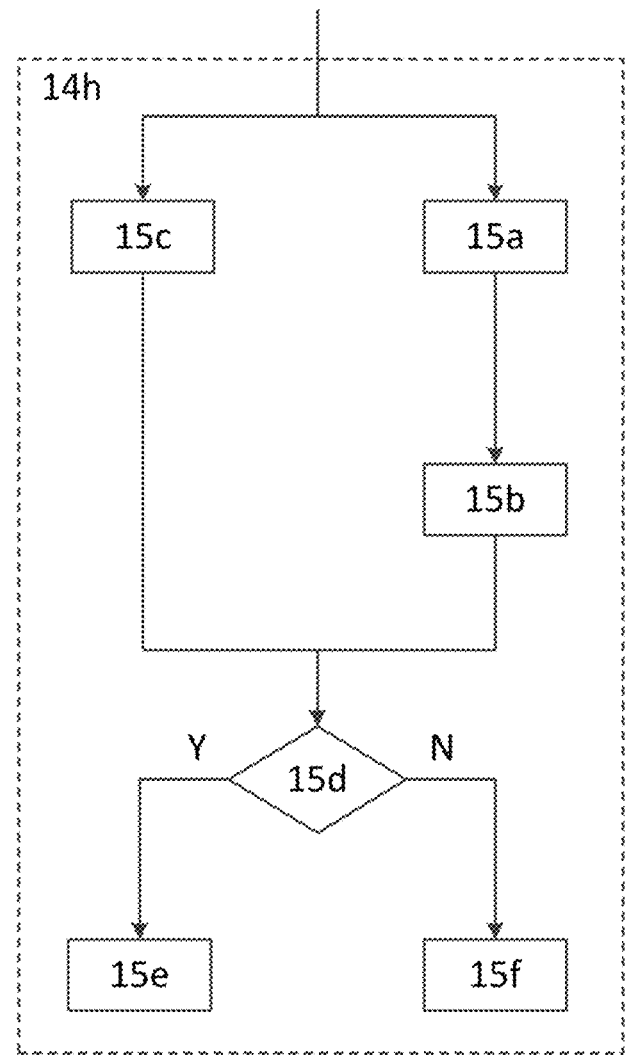
FIG. 15 is a flow chart schematically illustrating an implementation of a block comprised in the flow chart of FIG. 14, according to examples.

FIG. 15 is a flow chart illustrating an implementation of the block 14*h* of FIG. 14, according to some examples.

At block 15*c*, a first adjusted amplitude of the further pressure pulse 13*g*-13*i* may be determined based on the first assumption. This first adjusted amplitude may be calculated depending on the first characteristic of the further pressure pulse 13*g*-13*i* in the same or similar way as done at block 14*i*. Taking this into account, in some examples, the result of blocks 14*i* and 15*a* may be the same.

At block 15*a*, a second characteristic of the shape of the upward slope 9*r* of the heartbeat pulse of reference 9*a* may be determined.

This second characteristic may be calculated depending on the amplitude 9*b* of the heartbeat pulse of reference 9*a* and a time 9*c* until peak 9*g* of the heartbeat pulse of reference 9*a*. For example, this second characteristic may be determined based on the following formula:

$$C(\text{hb\_pulse}) = \frac{A(\text{hb\_pulse})}{t_s(\text{hb\_pulse})}$$

wherein: C(hb_pulse) is the second characteristic of the heartbeat pulse of reference 9*a*, A(hb_pulse) is the amplitude 9b of the heartbeat pulse of reference 9a, and $t_S$(hb_pulse) is the time 9c until peak 9g of the heartbeat pulse of reference 9a.

The above formula for determining the second characteristic conceptually represents an average inclination of the upward slope 9r of the heartbeat pulse of reference 9a. Therefore, this second characteristic may be considered as an indicator representing the shape of the heartbeat pulse of reference 9a, which may be useful for adjusting the further pressure pulses 13g-13i. Alternatively, other parameters and/or other mathematical relations between them could be considered for this aim.

At block 15b, a second adjusted amplitude of the further pressure pulse 13g-13i may be determined based on the second characteristic (calculated at block 15a) of the shape of the upward slope 9r of the heartbeat pulse of reference 9a. This second adjusted amplitude of the further pressure pulse 13g-13i may be determined further depending on the amplitude 10l of the further pressure pulse 13g-13i and the time 10o until peak 10i of the further pressure pulse 13g-13i.

In particular, the second adjusted amplitude of the further pressure pulse 13g-13i may be determined, at block 15b, based on the following formula:

$$A_{adjusted}(\text{further\_pulse}) = A(\text{further\_pulse}) - t_S(\text{further\_pulse}) \times C(\text{hb\_pulse})$$

wherein: $A_{adjusted}$(further_pulse) is the second adjusted amplitude of the further pressure pulse 13g-13i, A(further_pulse) is the amplitude 10l of the further pressure pulse 13g-13i, $t_S$(further_pulse) is the time 10o until peak 10i of the further pressure pulse 13g-13i, and C(hb_pulse) is the second characteristic of the heartbeat pulse of reference 9a.

The above formula for obtaining the second adjusted amplitude is based on the basic assumption that a heartbeat pulse of the patient substantially completely coincides (i.e. interferes) with the further pressure pulse 13g-13i.

For this reason, the second adjusted amplitude can be obtained by subtracting the result of multiplying the rising time 10o of the further pressure pulse 13g-13i by the average inclination of the upward slope 9r of the heartbeat pulse of reference 9a from the measured amplitude 10l of the further pressure pulse 13g-13i. This may conceptually represent that the heartbeat pulse of reference 9a is subtracted from the measured further pressure pulse 13g-13i.

At block 15d, a verification may be performed of whether the first adjusted amplitude is smaller than the second adjusted amplitude. In case of a positive result of said verification, a transition to block 15e may be performed.

In case of a negative result of said verification, a transition to block 15f may be performed.

At block 15e, the first adjusted amplitude may be selected as the result of adjusting the further pressure pulse 13g-13i. At block 15f, the second adjusted amplitude may be selected as the result of adjusting the further pressure pulse 13g-13i. In other words, the smaller of the first and second adjusted amplitudes is selected as the result of adjusting the further pressure pulse 13g-13i.

An aspect of selecting the smaller of the first and second adjusted amplitudes may be that an excessive correction of the further pressure pulse 13g-13i may be avoided. The second adjustment can generally be more aggressive (i.e. of larger magnitude) than the first adjustment, but this selection of the smaller adjustment may be carried out as a precautionary step for avoiding an excessive correction of the further pressure pulse 13g-13i.

The electro-stimulation caused at block 14b may be an electro-stimulation according to a Train of four (TOF) pattern based on generating a first electro-stimulation pulse 13b and three further electro-stimulation pulses 13c-13e. Taking this into account, the muscle response may be determined, at block 14c, having a TOF-ratio parameter corresponding to a relation between the amplitude of one of the three further pressure pulses 13g-13i and the amplitude of the first pressure pulse 13f.

The TOF-ratio parameter may be determined, at block 14c, based on a first verification of that A(first_pulse)≥A(second_pulse)≥A(third_pulse)≥A(fourth_pulse), wherein A(first_pulse), A(second_pulse), A(third_pulse) and A(fourth_pulse) are the adjusted amplitude of the first, second, third and fourth pressure pulses 13f-13i respectively. Physiologically speaking, it is inevitable that the muscle response to the four pulses of the TOF decrease with each pulse.

In case of a positive result of said first verification, which may indicate that the first, second, third and fourth pressure pulses 13f-13i are not so influenced by heartbeats so as to be at odds with the basic physiological truth mentioned before, the TOF-ratio parameter may be calculated (as usual) as the percentage of the fourth pressure pulse 13i with respect to the first pressure pulse 13f.

In case of a negative result of said first verification, the TOF-ratio parameter may be determined based on a second verification of that A(first_pulse)≥A(second_pulse)≥A(third_pulse)<A(fourth_pulse). In case of a positive result of said second verification, which may indicate that only the first, second and third pressure pulses 13f-13h are sufficiently reliable, the TOF-ratio parameter may be determined based on the following formula:

$$TOF_{RATIO} = \left(\frac{A(\text{third\_pulse})}{A(\text{first\_pulse})}\right)^X$$

wherein: $TOF_{RATIO}$ is the TOF-ratio parameter, and X is a value used to compensate that the TOF-ratio parameter is calculated depending on the amplitude of the first and third pulses rather than the fourth pulse.

In case of a negative result of said second verification, the TOF-ratio parameter may be determined based on a third verification of that A(first_pulse)≥A(second_pulse)<A(third_pulse)). In case of a positive result of said third verification, which may indicate that only the first and second pressure pulses 13f, 13g are sufficiently reliable, the TOF-ratio parameter may be determined based on the following formula:

$$TOF_{RATIO} = \left(\frac{A(\text{second\_pulse})}{A(\text{first\_pulse})}\right)^Y$$

wherein Y is a value used to compensate that the TOF-ratio parameter is calculated depending on the amplitude of the first and second pulses rather than the third and fourth pulses.

An aspect of the previous manner of determining the TOF-ratio parameter may be that a relatively reliable value may be obtained for said parameter even in the case of estimating that some of the pressure pulses 13f-13i are very unreliable. It is considered however that, in most cases, the TOF-ratio parameter may be properly calculated from the first and fourth pressure pulses 13f, 13i.

FIGS. 16a-16e illustrates an electro-stimulation electrode according to a first example, and FIGS. 17a-17g illustrates an electro-stimulation electrode according to a second example. The electro-stimulation electrodes are adapted to be applied dryly (or are suitable for dry application i.e. without the need of applying any electrically conductive gel under them) on a portion of skin, preferably a portion of intact skin of a patient.

Both electro-stimulation electrodes comprise a support layer 161, an electrically conductive medium 163, and a first conductive layer 164.

The support layer 161 may be made of an electrically insulating material and its outer surface is aimed at coming into contact with the skin of the patient. In other words, the support layer 161 is arranged in such a way that, in use, its outer surface contacts the patient's skin.

The support layer 161 is provided with at least one region provided with one or more holes 162 in the surface of contact with the patient.

The electrically conductive medium 163 is adhered to the inner surface of the support layer 161. This inner surface of the support layer 161 is the opposite surface to the surface of contact with the skin of the patient.

The electrically conductive medium 163 is arranged around the region 162 provided with one or more holes, such that the electrically conductive medium 163 completely or partially surrounds said region 162 in such a way that the electrically conductive medium 163 does not overlap with or cover said region 162.

The first conductive layer 164 contacts the electrically conductive medium 163 in such a way that the first conductive layer 164 at least partially covers or overlaps with the region with the at least one hole 162.

With respect to the first example, the following particular features are noted.

As can be seen in FIG. 16d, the electrically conductive medium 163 is arranged between the support layer 161 and the first conductive layer 164. A second conductive layer 165 is arranged on the surface of contact with the patient's skin, said second conductive layer 165 being in contact with the first conductive layer 164 through the one or more holes 162.

As can be seen in FIGS. 16d and 16e, the second conductive layer 165 has a convex top surface or a top surface provided with relief (or protruding portions) at the level of the region with holes 162, so that the contact with the skin of the patient is enlarged and ensured.

In this example, an arrangement as the one illustrated in FIG. 16a, i.e. with (micro) holes 162 in the support layer 161, is preferred, so that vertical forces to be supported by the thin conductive layers 164, 165 of the electrode are minimized.

This is because the possible orthogonal forces that may gravitate on the electrode are supported by the remaining non-perforated part of the resistant support layer 161, and not by the thin and delicate conductive layers 164, 165 themselves.

With respect to the second example, the following particular features are noted.

As can be seen in FIG. 17g, the first conductive layer 164 is arranged between the electrically conductive medium 163 and the support layer 161. In this case, a second conductive layer 165 is arranged between the first conductive layer 164 and the support layer 161, said second layer covering the hole 162.

A third layer 176 is arranged between the first conductive layer 164 and the second conductive layer 165, the third layer 176 having an outline substantially complementary to the outline of the hole 162 and being arranged coincident therewith (or fitted therein).

In this second example, there is an inner covering layer 177 whose outline exceeds the outline of the first and second conductive layers 164, 165.

The support layer 161 may be made of Nylon, paper or a nonwoven fabric and the electrode (when in use) comes into contact with the skin of the patient through the small window 162 existing thereon. The layer 163 is the terminal end of a conductive track through which electricity is conveyed to the electrode. Such a conductive track can be manufactured e.g. either by depositing an electrically conductive metallic fabric or by printing an electrically conductive ink on the inner surface of the support layer 161.

The layers 164, 165 and 176 give shape to the body of the Electrode, and can be manufactured by printing an ink of conductive composite (e.g. a liquid silicone-based matrix doped with electrically conductive particles) or intrinsically conductive polymer (ICP).

The printing of the layer 164 should be enough for obtaining a functional electrode. However, printing of the other two layers 165, 176 is generally preferred.

The layer 176 has a main objective of levelling the front surface of the layer 164, since said layer 164 has a slight cavity in its centre, which is due to the step (or protruding region) of the layer 164 which is introduced in the central hole of the layer 163.

The layer 165 has the single objective of acting as a closure (or cover) of the layer 176, thereby avoiding that said layer 176 could detach from the layer 164 and leave the electrode through the hole 162 existing in the fabric that constitutes the layer 161.

As can be seen in FIGS. 16a and 17a, the electrically conductive medium 163 completely surrounds the region of the support layer 161 provided with one or more holes 162.

In both examples, the electrically conductive medium 163 may be e.g. a conductive track, a cable, a conductive metallic fabric or a printed conductive ink.

Figure 18:
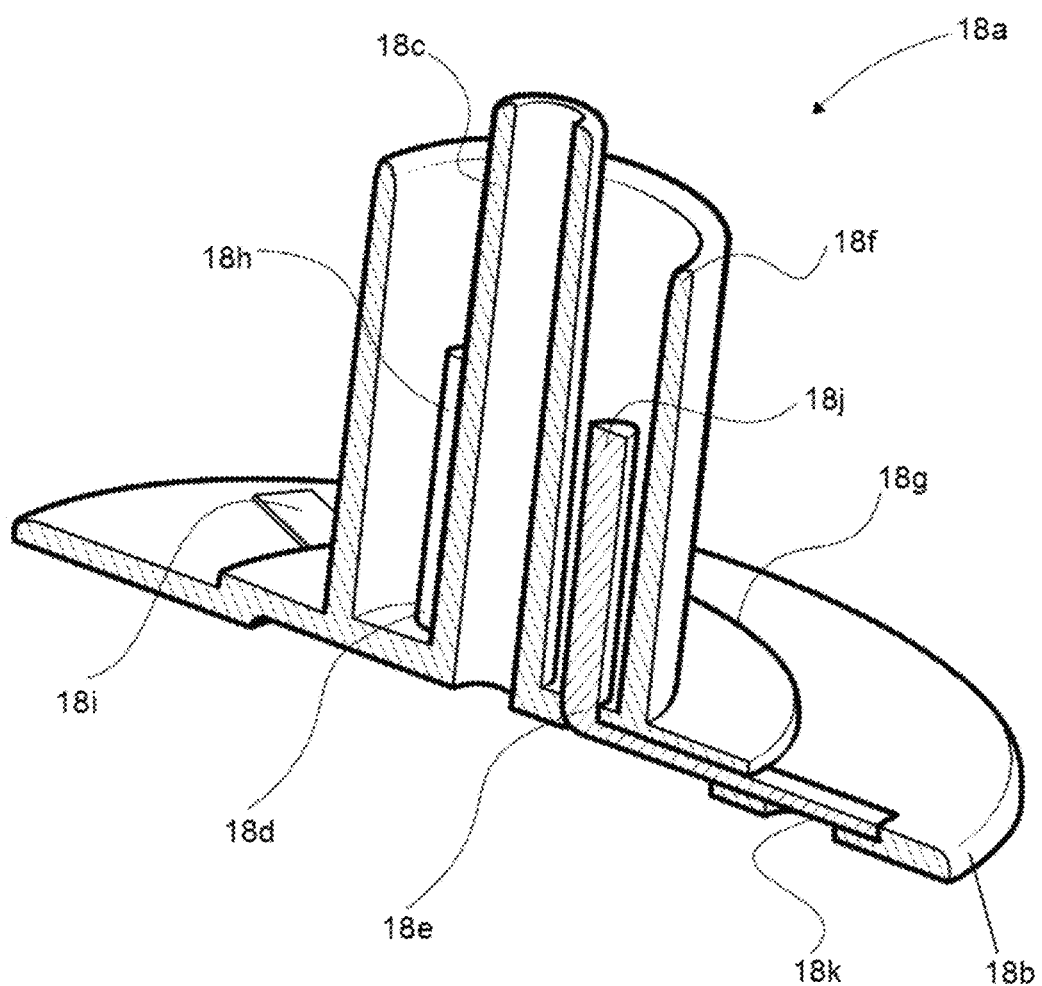
FIG. 18 is a perspective cross-sectional view of a hybrid air-signal connector according to an example.

FIG. 18 shows a hybrid air-signal connector 18a for a pressure cuff for electro-stimulation 23r (see FIG. 23), which is adapted for implementing a connection with an air-signal tube 23p (see FIG. 23) for the conveyance (or introduction) of both pressurized air and electrical signals.

The hybrid air-signal connector 18a comprises a main body and two substantially L-shaped electrodes 18d, 18e. The main body has a base 18b from which a first tubular portion 18c extends on a (outer) side at its centre, the first tubular portion 18c being suitable for the coupling of the tube 23p.

That is, the main body has a base 18b with a first tubular portion 18c arranged on a first side (or outer side) 18g of the base 18b in such a way that, in use, the first tubular portion 18c is fitted into an air conduit of the tube 23p.

Figure 24:
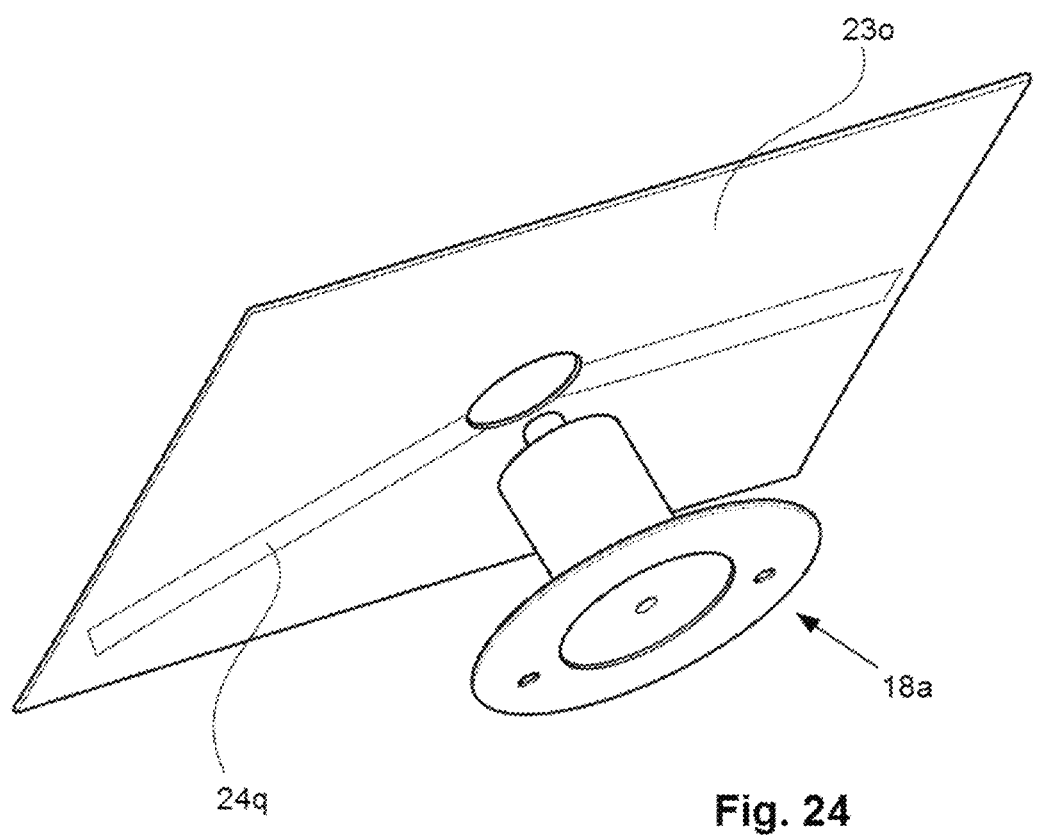
FIG. 24 is a bottom perspective view of the hybrid air-signal connector which is being fitted into a connection bore of the cuff at an inner side of the cuff's fabric cover.

The L-shaped connection electrodes 18d, 18e have external terminals 18h, 18j for connection with external wires (i.e. external to the pressure cuff), and internal terminals 18i, 18k for connection with conductive tracks 24q (see FIG. 24) internal to the cuff 23r. FIG. 24 schematically partially shows an inner side of the outer envelope (or inflatable bag) 23o of the cuff 23r, which may also be referred to as base-fabric 23o hereinafter.

The external terminals 18h, 18j extend from the base 18b substantially parallel (and optionally substantially contiguously) to the first tubular portion 18c. The external terminals 18h, 18j are therefore arranged in such a way that, in use, each external terminal 18*h*, 18*j* contacts an electrically conductive wire of the air-signal tube 23*p*.

The internal terminals 18*i*, 18*k* may be embedded in the base 18*b* with their ends 19*m*, 19*n* exposed on the outer side 18*g* of the base 18*b*. In other words, the internal terminals 18*i*, 18*k* may be embedded in the base 18*b* with an end portion 19*m*, 19*n* arranged on the outer face of the base 18*b* in such a way that, in use, the end portions 19*m*, 19*n* can contact an inner conductive track 24*q* of the cuff 23*r* when the hybrid air-signal connector 18*a* is introduced into a connection bore of the cuff 23*r* (see FIG. 24).

The hybrid air-signal connector 18*a* comprises a cylindrical enclosure 18*f* for protecting the external terminals 18*h*, 18*j* and guiding the coupling of the tube 23*p* which serves to transmit air and electrical signals. This cylindrical enclosure 18*f* may be described as a second tubular portion 18*f* outwardly coaxially arranged with respect to the first tubular portion 18*c*.

The cylindrical enclosure 18*f* may also constitute a barrier avoiding the intrusion of liquids and/or dust in the connection between the tube 23*p* and the connector 18*a*.

The cylindrical enclosure (or second tubular portion) 18*f* has a lower height (or length) than the first tubular portion 18*c*. Once the tube 23*p* has been inserted into the cylindrical enclosure 18*f*, the welding of both components ensures both protection against intrusions and mechanical resistance of the connection between the tube 23*p* and the connector 18*a*.

As shown in the figures, the hybrid air-signal connector 18*a* may preferably be made up of only three single bodies: the main body and the two electrodes 18*d*, 18*e*. This configuration or structure can be obtained through injection on and around (i.e. overmolding) the metallic electrodes 18*d*, 18*e* placed inside a thermoplastic injection mould.

Preferably, polyurethane is used as base material for the injection of the body of the connector 18*a*, and copper as base material for the stamping and die-cutting of the metal electrodes 18*d*, 18*e*. As can be seen in e.g. FIG. 18, the external terminals 18*h*, 18*j* are substantially cylindrical (i.e. have a substantially circular cross-section), and the internal terminals 18*i*, 18*k* are substantially flat (i.e. have a flat shape).

Figure 19:
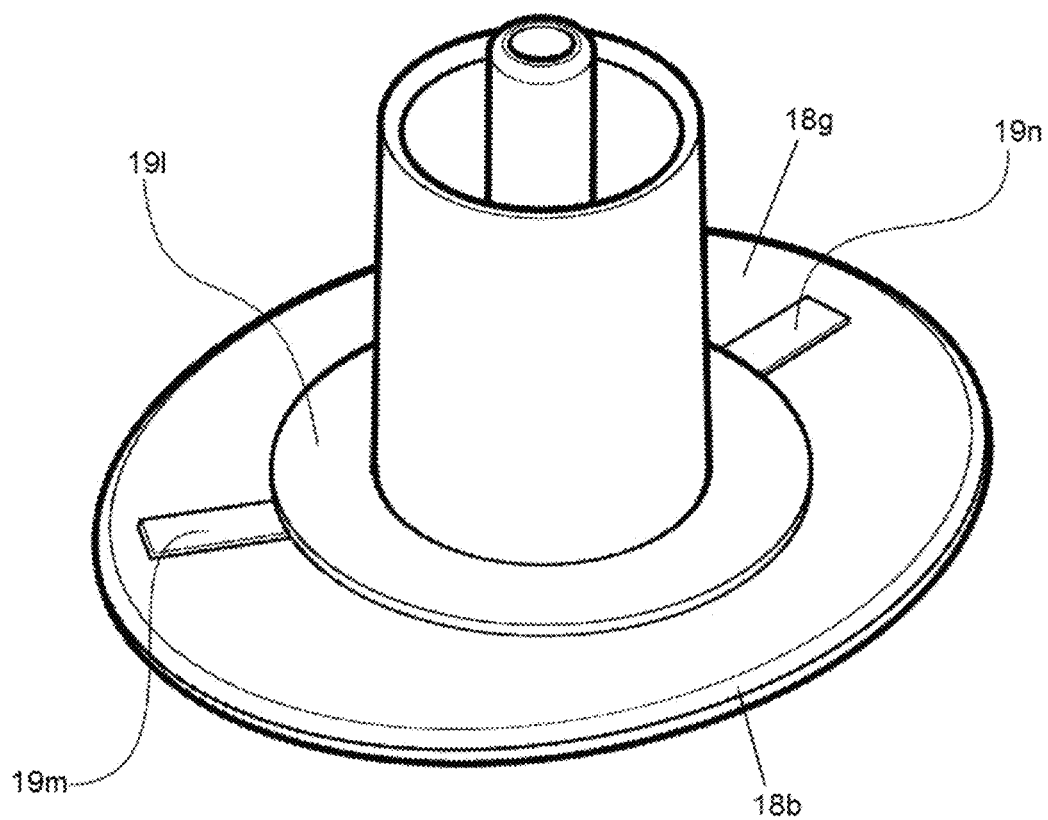
FIG. 19 is a top perspective view of the air-signal hybrid connector.

In FIG. 19, the base 18*b* can be seen comprising a central ring 191 for (providing) pneumatic air tightness (to the connector 18*a*). The central ring 191 protrudes with respect to the rest of the base 18*b* at a first side (or outer side) 18*g* of the base 18*b*. When suitably coupled to the cuff 23*r*, this ring 191 will come into contact with an inner side of the base-fabric 230 (or fabric constituting the envelope) of the cuff 23*r*.

This last feature provides a wide and uninterrupted (i.e. 360 degrees of scope) contact surface through which pneumatic air tightness of the connection between the connector 18*a* and the cuff 23*r* is ensured. Such pneumatic air tightness will be definitely ensured by the subsequent welding of the base-fabric 23*o* against the central ring 191.

Figure 20:
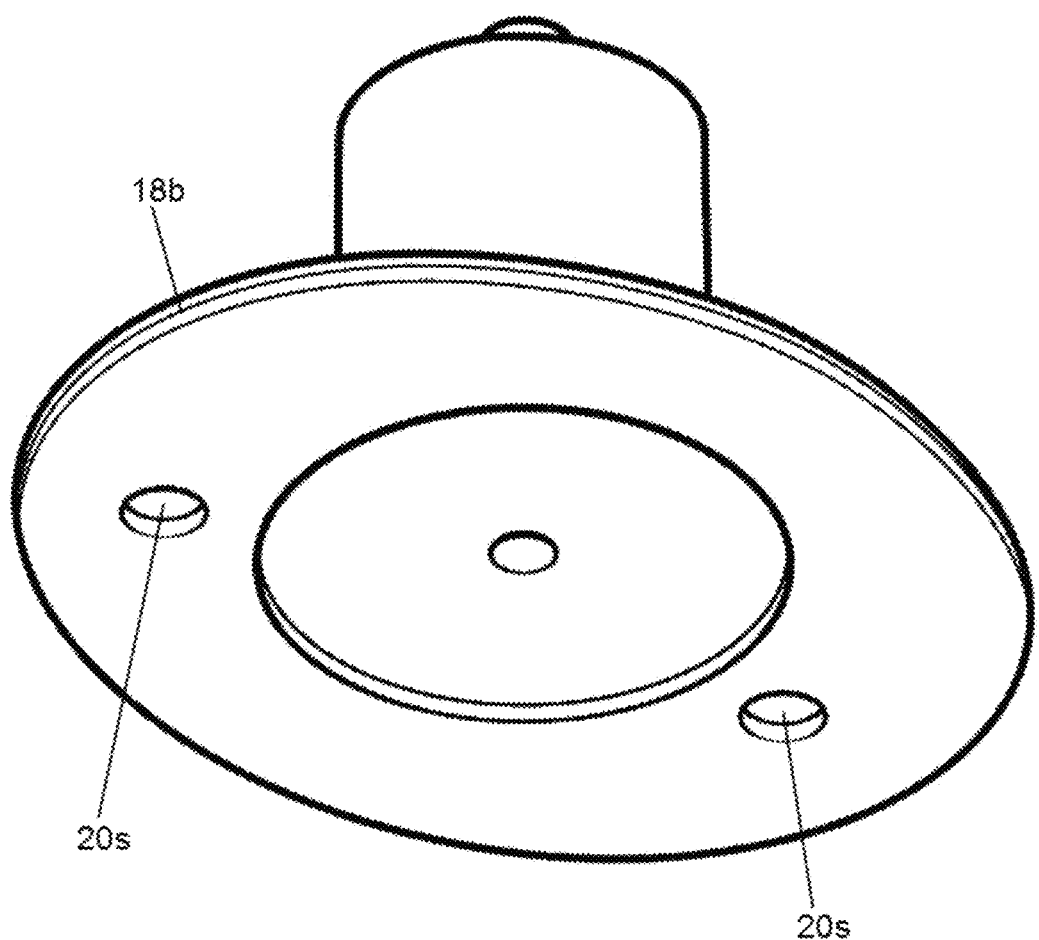
FIG. 20 is a bottom perspective view of the hybrid air-signal connector.

FIG. 20 is a bottom perspective view of the hybrid air-signal connector 18*a* showing that the base 18*b* may comprise holes 20*s* for accessing to the ends (or end portions) 19*m*, 19*n* of the internal terminals 18*i*, 18*k* from the bottom (or inner) side of the base 18*b*.

Figure 21:
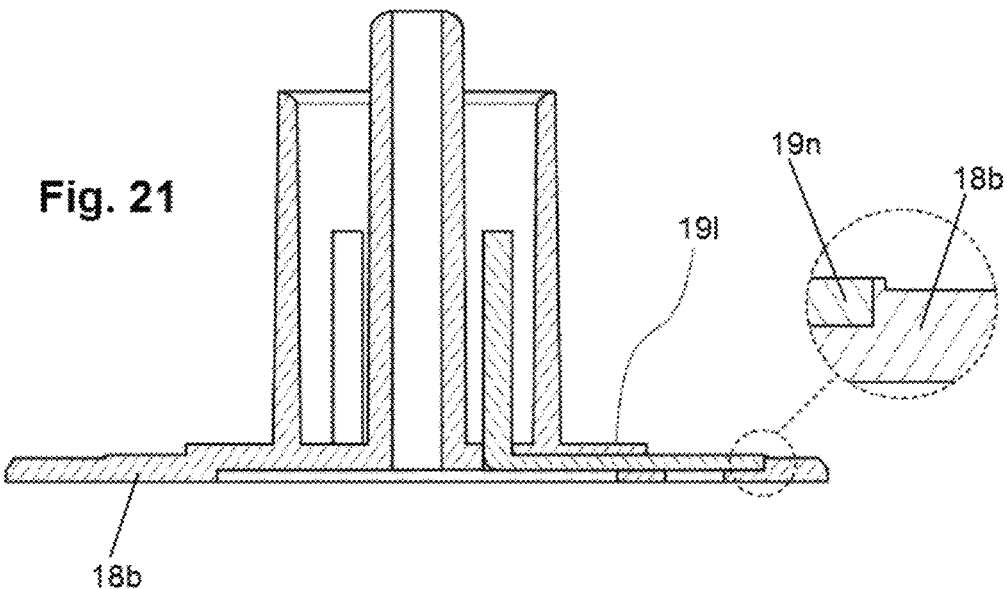
FIG. 21 is a cross-sectional view of the hybrid air-signal connector.

FIG. 21 is a front cross-sectional view of the hybrid air-signal connector 18*a*, wherein previously described configuration features can be seen from another point of view. The central ring 191 for pneumatic air tightness can be seen protruding with respect to the rest of the base 18*b* at a first side (or outer side) of the base 18*b*. An internal terminal end portion 19*n* can also be seen arranged on the first side (or outer side) of the base 18*b*, in such a way that said end portion 19*n* is exposed.

Figure 22:
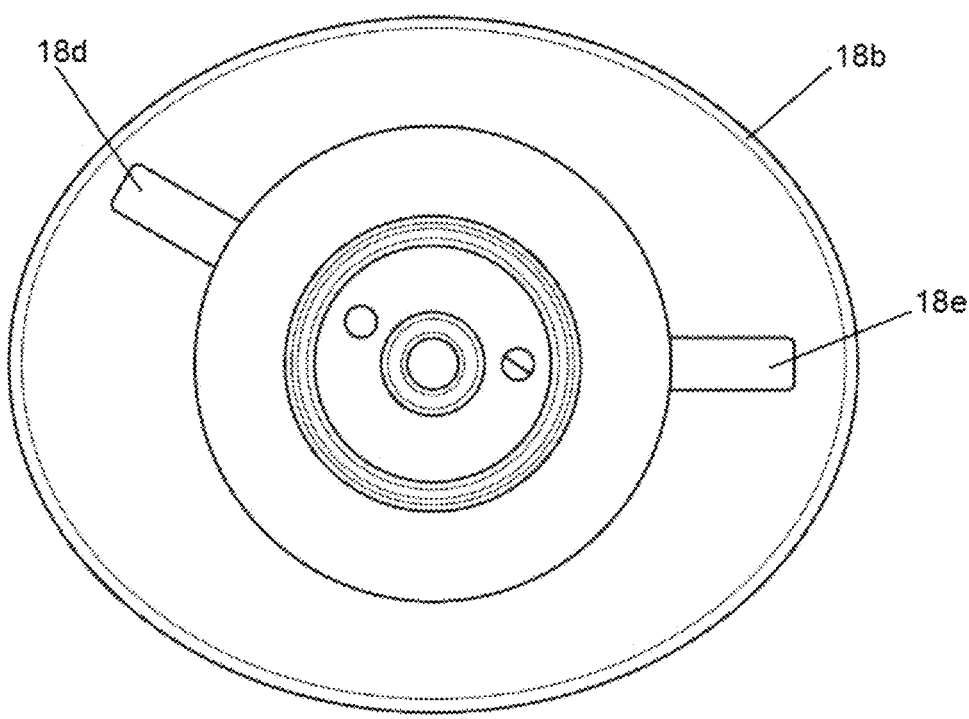
FIG. 22 is a plan view of the hybrid air-signal connector.

In FIG. 22, the electrodes 18*d*, 18*e* are shown arranged asymmetrically in order to ensure a proper polarity in the connection. As can be seen also in FIG. 22, the base 18*b* may have a substantially elliptical shape.

Figure 23:
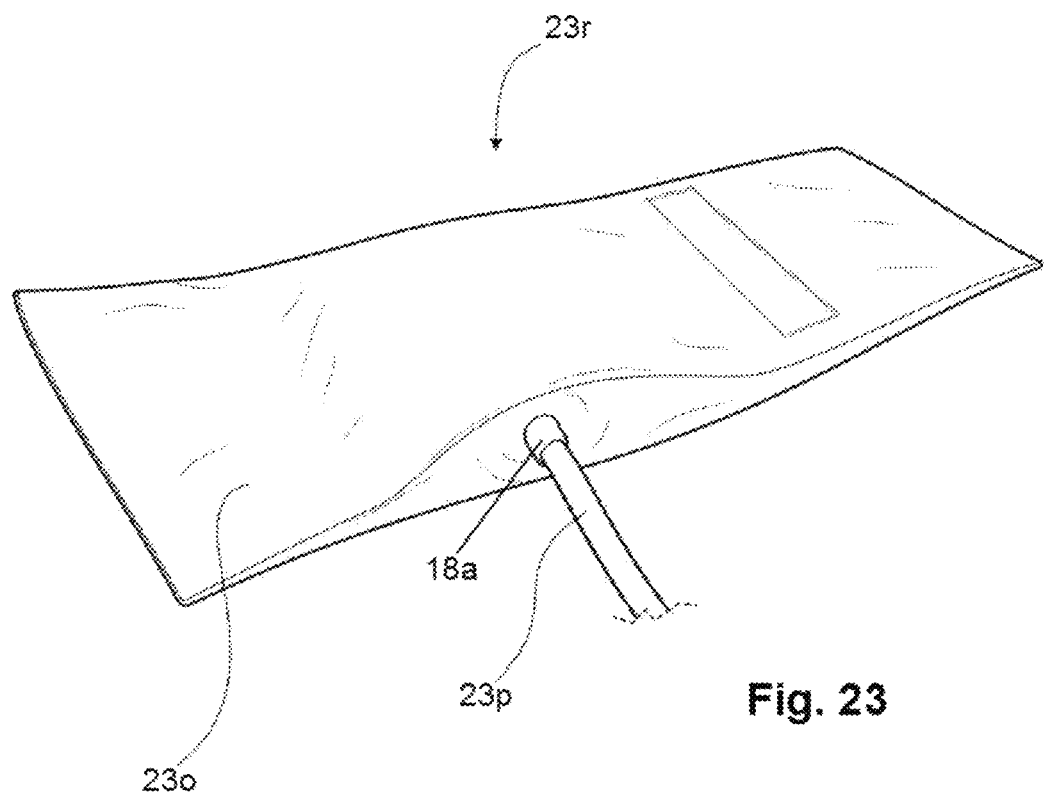
FIG. 23 is a perspective view of a cuff and a hybrid air-signal tube connected to the cuff through the hybrid air-signal connector.

FIG. 23 is a perspective view of a pressure cuff 23*r* and a tube 23*p* connected to the cuff 23*r* through the hybrid air-signal connector 18*a*.

FIG. 24 illustrates that, upon insertion of the hybrid air-signal connector 18*a* into the opening of the cuff 23*r* aimed at that purpose, the end portions 19*m*, 19*n* (not shown in FIG. 24) of the metal electrodes 18*i*, 18*k* (inevitably) come into contact with the corresponding conductive tracks 24*q*. These tracks 24*q* are printed on or adhered to an inner surface of the base-fabric 230 of the cuff 23*r*.

In any of the previous examples, the main body of the connector 18*a* may be made e.g. of polyurethane.

Figure 25:
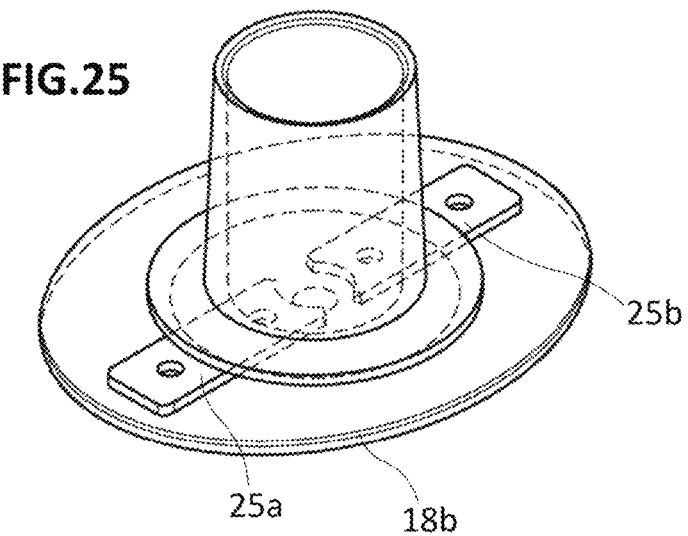
FIG. 25 is a top perspective view of a hybrid air-signal connector according to a further example.
Figure 26:
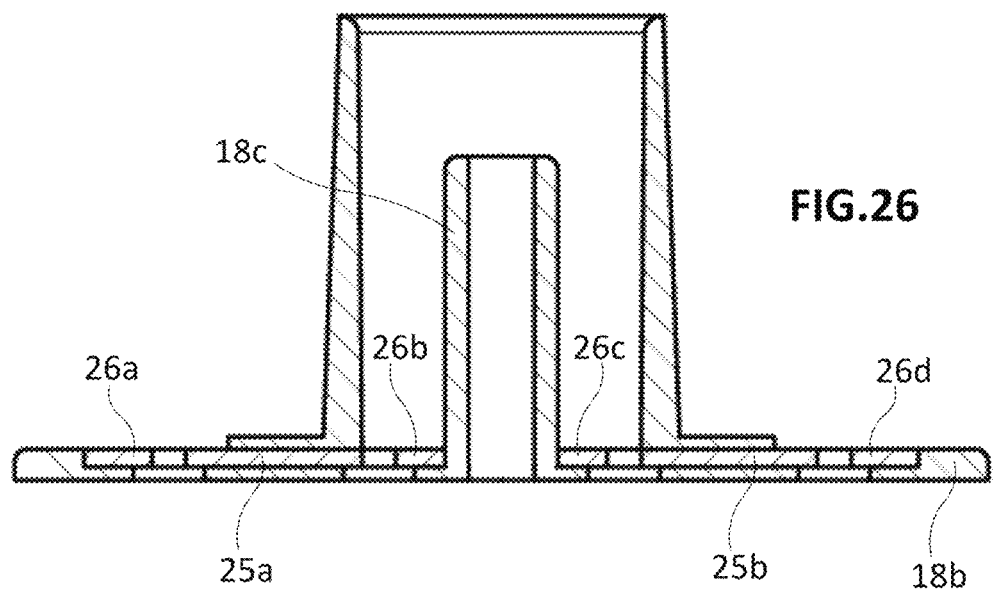
FIG. 26 is a cross-sectional view of the hybrid air-signal connector of FIG. 25.

FIG. 25 is a perspective view of a hybrid air-signal connector, according to a further example, for connecting a pressure cuff for electro-stimulation and an air-signal tube. FIG. 26 is a cross-sectional view of said hybrid air-signal connector. This hybrid air-signal connector is similar to the ones shown in previous Figures. One difference is that, in this particular case, the connector comprises first and second connection electrodes 25*a*, 25*b* with flat shape instead of the L shape previously described in the context of other examples.

The first flat electrode 25*a* is shown embedded in a base 18*b* of the hybrid air-signal connector and having an external terminal 26*b* and an internal terminal 26*a*. The second flat electrode 25*b* is also shown embedded in the base 18*b* of the hybrid air-signal connector and having an external terminal 26*c* and an internal terminal 26*d*.

Each of the external terminals 26*b*, 26*c* is shown arranged on the base 18*b* in such a way that, in use, the external terminal 26*b*, 26*c* contacts an end of an electrically conductive cable of the air-signal tube when a corresponding tubular portion 18*c* (of the connector) is fitted into an air conduit of the air-signal tube. Said tubular portion 18*c* is not shown in FIG. 25 in order to not obscure the depiction of the electrodes 25*a*, 25*b*.

Each of the internal terminals 26*a*, 26*d* is shown arranged on the base 18*b* in such a way that, in use, the internal terminal contacts an inner conductive track 24*q* of the pressure cuff 23*r* when the hybrid air-signal connector is introduced into a connection bore of the pressure cuff.

An advantageous aspect of such a hybrid air-signal connector with flat electrodes 25*a*, 25*b* may be that said connector yields a substantially lower risk of failure during the splicing (or coupling) of the external terminals 26*b*, 26*c* to corresponding electrically conductive cables of the air-signal tube. This is a consequence of the substantially larger contact surface offered by said external terminals 26*b*, 26*c*.

Said splicing may simply be a collateral effect of the coupling of the air-signal tube 23*p* with the air-signal connector 18*a*, which is carried out by fitting the first tubular portion 18*c* of the air-signal connector into the air conduit of the hybrid air-signal tube. In this splicing operation, the increased contact surface offered by the flat-shaped external terminals 26*b*, 26*c* may effectively relieve the operator from e.g. the requirement of ensuring a substantially perfect coaxial alignment between each of the external terminals of the connector and corresponding electrically conductive cable of the air-signal tube.

Most of the principles and features previously commented with respect to hybrid air-signal connectors with L-shaped electrodes may be compatible with this last hybrid air-signal connector with flat electrodes. Any of said compatible principles and features may thus be equally or similarly applied to obtain diverse configurations of hybrid air-signal connectors with flat electrodes.

FIGS. 27a-27d have been described before.

Figure 27B:
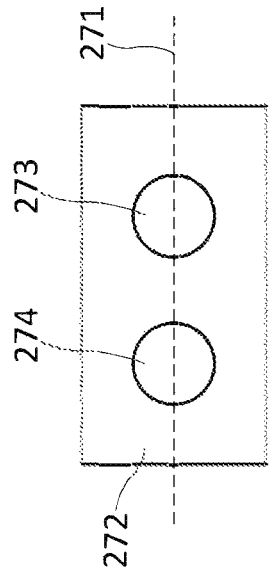
Figure 27A:
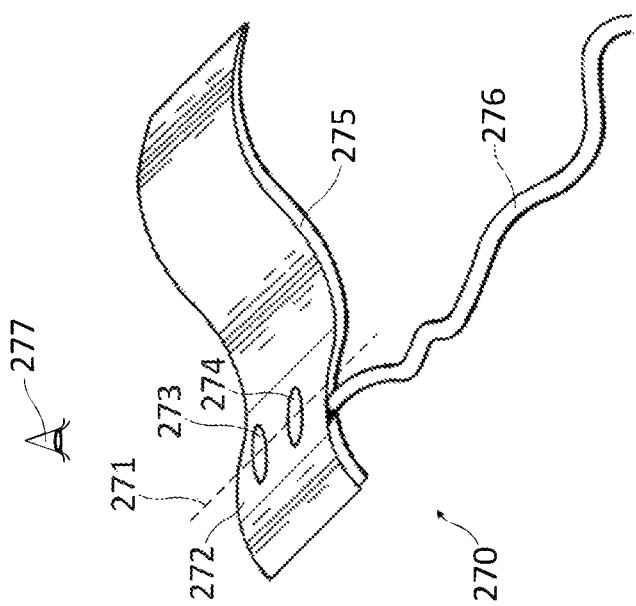
FIG. 27a schematically illustrates a perspective view of an example of prior art pressure cuff with electro-stimulation electrodes.
Figure 27D:
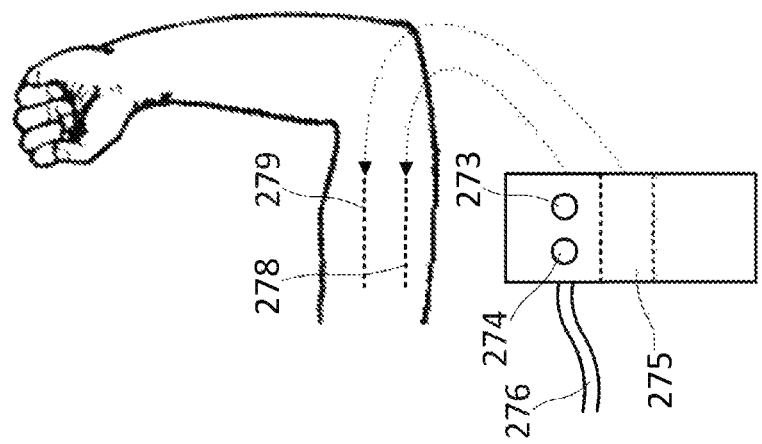
FIG. 27d schematically illustrates the pressure cuff of FIG. 27c positioned in accordance with its correct arrangement around a patient's left arm.
Figure 27C:
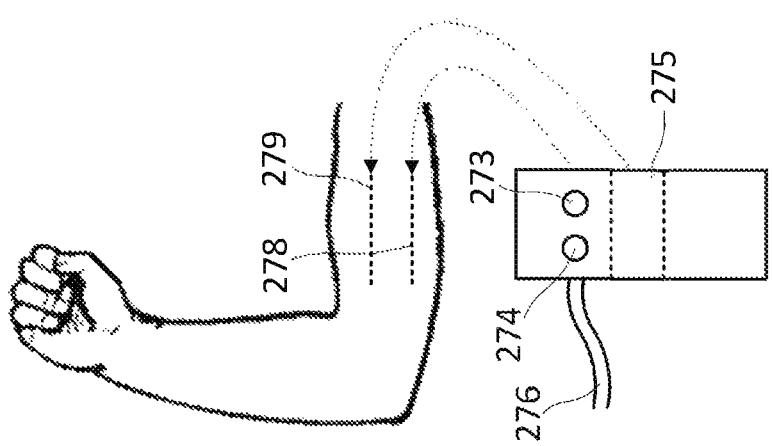
FIG. 27c schematically illustrates a prior art pressure cuff positioned in accordance with its correct arrangement around a patient's right arm.
Figure 28A:
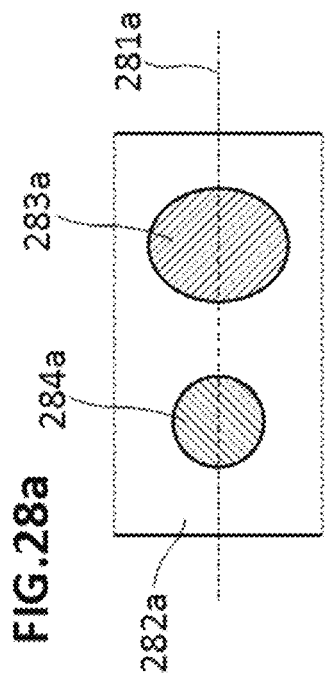
FIG. 28a-28c schematically illustrate respective views similar to the one shown in FIG. 27b but with different configurations of electrodes according to respective examples.

FIG. 28a schematically illustrates a view similar to the one shown in FIG. 27b but with a new example of configuration of electrodes. In particular, an active electrode 284a (or cathode or negative lead, through which current is supplied) and a passive electrode 283a (or anode or positive lead, through which current is collected) are shown arranged on a pressure cuff region 282a in such a way that, in use, both electrodes 283a, 284a are placed on the path 281a of the peripheral motor nerve to be electro-stimulated. However, the passive electrode 283a has a contact surface larger in size than the contact surface of the active electrode 284a.

This configuration may permit minimizing or avoiding the risk of appearance of the "Anodal Block of Conduction" phenomenon, irrespective of whether the cuff is applied to the left or right arm (or leg) of the patient.

When the active electrode 284a is in a distal position and the passive electrode 283a is in a proximal position, the "Anodal Block of Conduction" phenomenon cannot occur according to Pflüger's Law.

When the active electrode 284a is in a proximal position and the passive electrode 283a is in a distal position, the larger size of the passive electrode 283a may induce a relatively low hyperpolarization level in the underlying peripheral motor nerve's outer membrane. This may minimize or eliminate the risk of appearance of the "Anodal Block of Conduction" phenomenon, as argued in other parts of the description. The same principle applies to configurations shown in other Figures.

This configuration may also improve the electrical protection of the patient's heart, since the larger size of the passive electrode 283a constitutes an effective and preferential exit for the electro-stimulation current transmitted by the active electrode 284a, as argued in other parts of the description. This principle will be equally used with reference to other Figures.

Figure 28B:
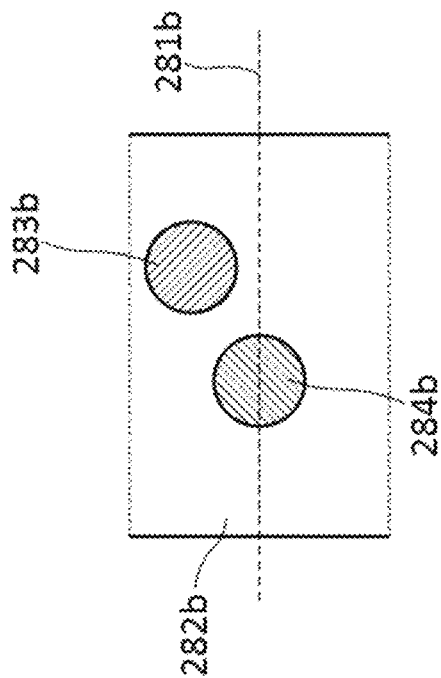

FIG. 28b schematically illustrates a view similar to the one shown in FIG. 28a but with another example of configuration of electrodes. An active electrode 284b and a passive electrode 283b are shown arranged on a pressure cuff region 282b in such a way that, in use, only the active electrode 284b is placed on the path 281b of the peripheral motor nerve to be electro-stimulated.

This arrangement of electrodes may permit avoiding the risk of appearance of the "Anodal Block of Conduction" phenomenon, irrespective of whether the cuff is applied to the left or right arm (or leg) of the patient.

When the cuff is applied to the right arm, the passive electrode 283b is placed outside the path 281b of the nerve to be stimulated. When the cuff is applied to the left arm, the passive electrode 283b is equally placed outside the nerve path 281b.

Figure 28C:
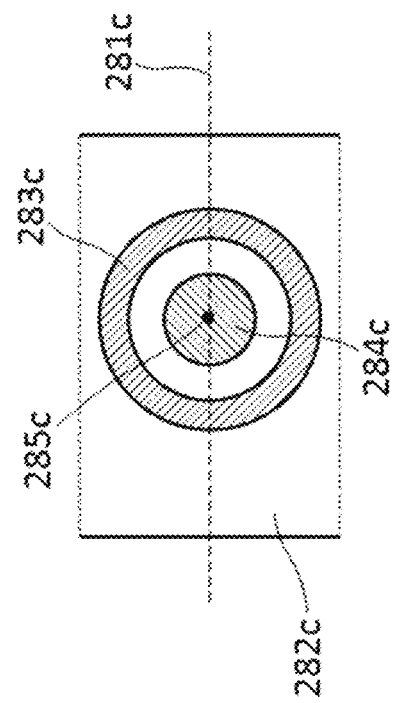

FIG. 28c schematically illustrates a view similar to the ones shown in FIGS. 28a and 28b but with another example of configuration of electrodes. An active electrode 284c and a passive electrode 283c are shown arranged on a pressure cuff region 282c in such a way that, in use, the active electrode 284c is placed on the path 281c of the peripheral motor nerve to be electro-stimulated and the passive electrode 283c completely surrounds the active electrode 284c in a coaxial manner with respect to a central axis 285c. The passive electrode 283c is larger in size than the active electrode 284c.

With this configuration, a portion of the passive electrode 283c will always be laid out in a further distal position on the path 281c of the peripheral motor nerve, irrespective of whether the cuff is applied on the right or left limb of the patient. However, the relative larger size of the passive electrode 283c may minimize the risk of appearance of the "Anodal Block of Conduction" phenomenon, according to the principle described with respect to FIG. 28a, in which case a reliable muscle response will always occur.

This configuration may also improve the electrical protection of the patient's heart according to the principle described with respect to FIG. 28a.

Figure 29A:
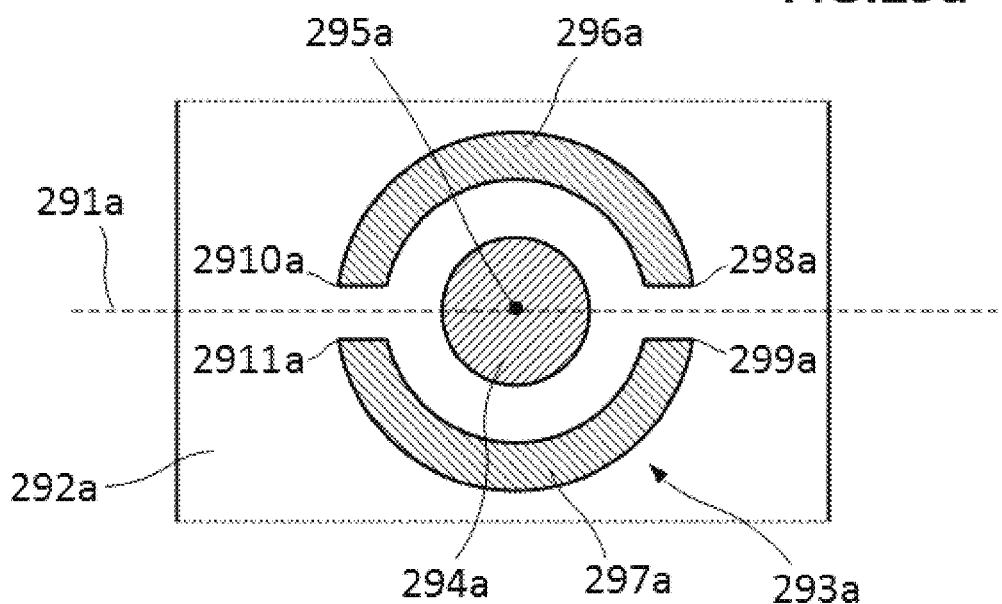
FIG. 29a-29b schematically illustrate respective views similar to the ones shown in FIGS. 28a-28c but with different configurations of electrodes according to respective other examples.

FIG. 29a schematically illustrates a view similar to the ones shown in FIGS. 28a-28c but with another example of a configuration of electrodes. An active electrode 294a is shown to be arranged, in use, on the peripheral motor nerve path 291a. A passive electrode 293a is shown partially surrounding the active electrode 294a and formed as two annular segments 296a, 297a.

A first of the annular segments 296a has a first end 2910a and a second end 298a, and a second of the annular segments 297a has a first end 2911a and a second end 299a. The first ends 2910a, 2911a are shown facing each other with a first gap in between and the second ends 298a, 299a are shown facing each other with a second gap in between, such that, in use, the passive electrode 293a is not directly arranged on/over the nerve path 291a.

This arrangement of electrodes may permit avoiding the risk of appearance of the "Anodal Block of Conduction" phenomenon, since the passive electrode 293a is placed, in use, outside the nerve path 291a, irrespective of whether the cuff is applied to the right or left arm (or leg) of the patient. Hence, a reliable muscle response will always occur in this case.

This configuration may also improve the electrical protection of the patient's heart according to the principle described with respect to FIG. 28a.

Figure 29B:
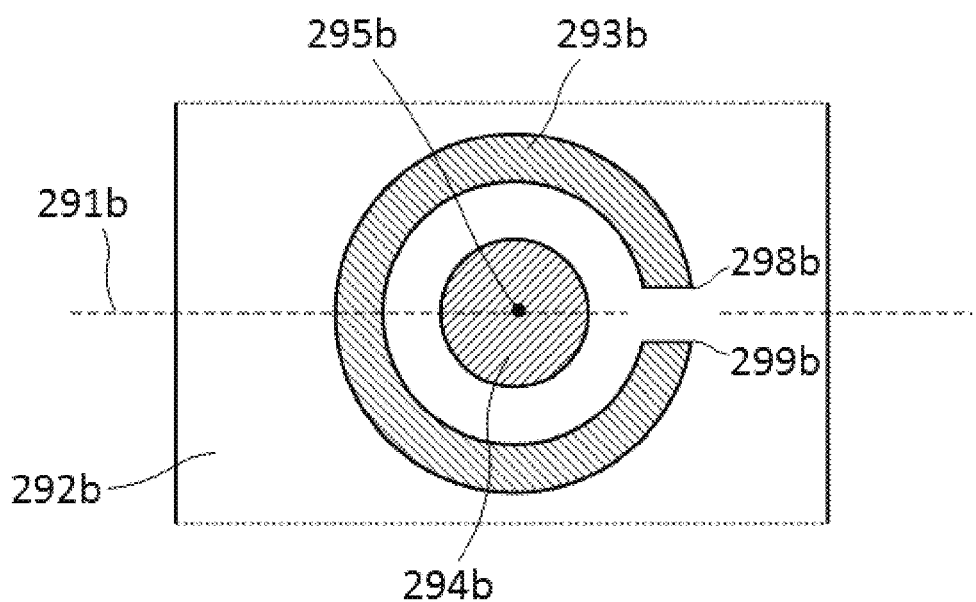

FIG. 29b schematically illustrates a view similar to the ones shown in FIGS. 28a-29a but with another example of configuration of electrodes. An active electrode 294b is shown to be arranged, in use, on the nerve path 291b. A passive electrode 293b is shown partially surrounding the active electrode 294b and substantially C-shaped. The passive electrode is shown having a first end 298b and a second end 299b facing each other with a gap in between.

Such an arrangement of electrodes may permit minimizing or avoiding the risk of appearance of the "Anodal Block of Conduction" phenomenon, in which case a reliable muscle response will always occur.

The cuff may be applied on a patient's limb in such a way that the furthest distal stretch of the nerve path 291b substantially lies below the gap of the passive electrode 293b. In this case, the passive electrode 293b would not induce any hyperpolarisation on the outer membrane of the nerve. Hence, the risk of appearance of the "Anodal Block of Conduction" phenomenon is eliminated.

Alternatively, the cuff can be applied on a patient's limb in such a way that the furthest distal stretch of the nerve path 291b falls below a portion of the passive electrode 293b. In this case, the relative larger size of the passive electrode 293b may still minimize the risk of appearance of the "Anodal Block of Conduction" phenomenon, according to the principle described with respect to FIG. 2a.

This configuration may also improve the electrical protection of the patient's heart according to the principle described with respect to FIG. 28a.

FIG. 30a schematically illustrates a sectional view of a portion 306 of a laminated base material suitable for constructing electro-stimulation circuits according to an example. This particular laminated base material 306 is shown formed as a multilayer film having a first layer 302 of thermoplastic polymer doped with electrically conductive particles 307 and a second layer 303 of electrically conductive material. The first layer 302 and the second layer 303 may be attached to each other with a heated lamination process as shown in FIG. 30c.

FIG. 30b schematically illustrates a sectional view of a portion 306' of another laminated base material suitable for constructing electro-stimulation circuits according to another example. In this case, the laminated base material 306' is shown formed as a multilayer film having a first layer 302 of thermoplastic polymer doped with electrically conductive particles 307, a second layer 303 of electrically conductive material, and a third layer 304 of thermoplastic polymer that may also be doped with electrically conductive particles 307.

These three layers 302-304 may be attached together in such a way that the second layer 303 is sandwiched between the first layer 302 and the third layer 304. This attachment may be implemented through a heated lamination process as the one illustrated in FIG. 30c.

FIG. 30c schematically illustrates a process of fabricating a laminated base material similar to the ones shown in FIGS. 30a and 30b. This process may be a heated lamination process based on introducing two corresponding sheets 302, 303 (for obtaining the structure of FIG. 30a) or three corresponding sheets 302-304 (for obtaining the structure of FIG. 30b) into a lamination apparatus.

This lamination apparatus may comprise at least two rollers 300, 301 configured to rotate while pressing the input sheets 302, 303 or 302-304 in such a way that a desired multilayer film 305 is generated. Suitable heating means may provide a proper heating at the pressure region between the rollers 300, 301 in such a way that a relatively strong attachment between the layers or sheets 302, 303 or 302-304 may be implemented.

An aspect of using this heated lamination process is that a relatively compact multilayer film 305 can be obtained without the need of using adhesives or similar substances. Since this multilayer film 305 is intended for constructing electro-stimulation circuits to be applied on the skin of a human being, the absence of such adhesives (or similar substances) may avoid causing undesired alterations, such as e.g. irritation, of the skin.

Another aspect of using this heated lamination process is that it may make the fabrication of the multilayer film 305 easier and cheaper in comparison with other types of manufacturing processes. For example, the layer-by-layer deposition of thin films, which is typically used e.g. in the Printed Electronics Industry and/or the Phase-Vapour Deposition technology, may require several intermediate steps.

The effective deposition of each layer included in the multilayer film may comprise e.g. the printing/deposition step itself, the subsequent curing step (often, this step is compulsorily performed off-line of the main manufacturing printing line), a subsequent registry step of the multilayer stack already deposited with the silk-screen printing apparatus when back into the printing line, etc.

Nevertheless, the proposed heated lamination process may be just a single-step and single-machine process which, as a result, can make the manufacturing process of the base material 305 more easily scalable to mass production.

A further aspect of using this heated lamination process is that a relatively thin and efficient multilayer film 305 for constructing electro-stimulation circuit(s) may be obtained.

Figure 31B:
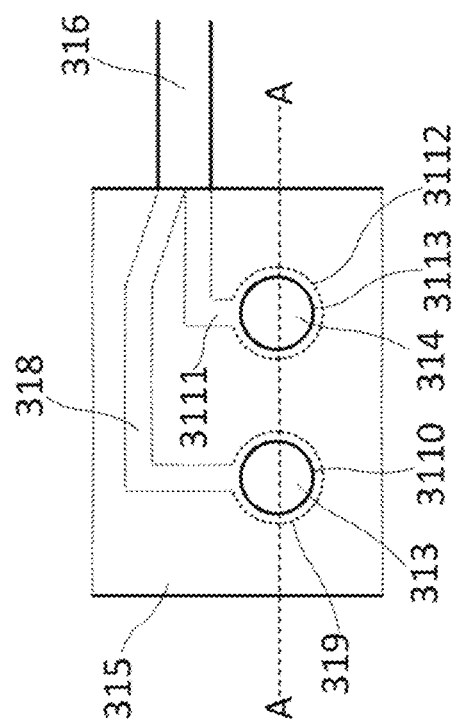
FIG. 31b schematically illustrates an enlarged view of a region of a pressure cuff similar to the one depicted in FIG. 31a, wherein configuration details about the electro-stimulation circuits are shown.
Figure 32:
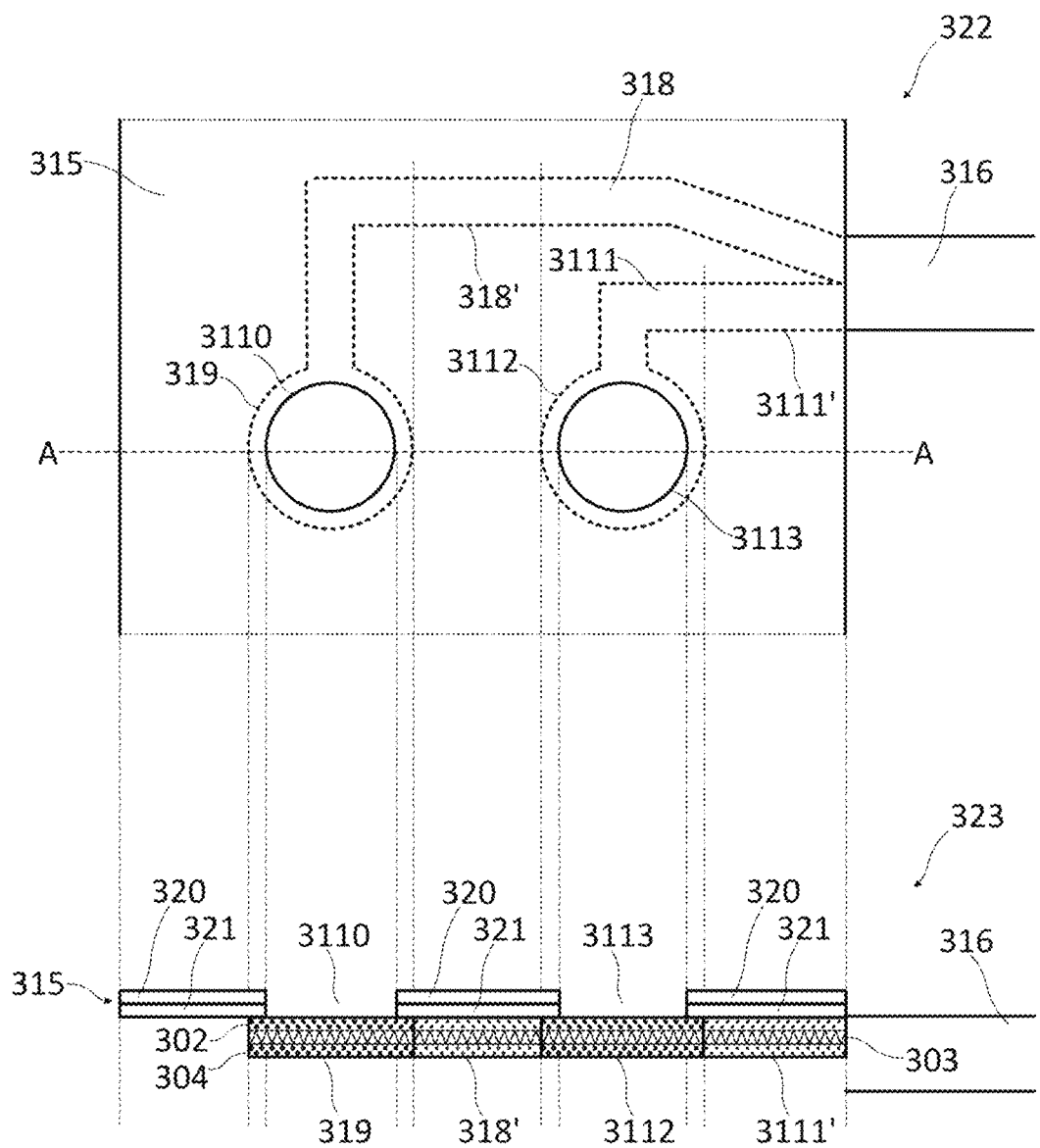
FIG. 32 schematically illustrates a cross sectional view of a pressure cuff region similar to the one shown in FIG. 31b, said view having been taken according to a plane indicated in FIG. 31b.

Once generated, a laminated base material such as the ones shown in FIGS. 30a and 30b may be properly cut for obtaining different examples of electro-stimulation circuits, such as e.g. the ones shown in FIGS. 31b and 32. These electro-stimulation circuits may comprise an electrode portion and a track portion integrally formed as a single multilayer film having a laminated structure such as the ones described with reference to FIGS. 30a and 30b.

The electrode portion may be configured to be arranged on a skin region of a patient and to either transmit or collect an electrical current to/from a region of a patient which is at least partially on a nerve of the patient for electro-stimulating a peripheral motor nerve. The track portion may be configured to conduct the electrical current to/from the electrode portion.

In a laminated base material such as the ones shown in FIGS. 30a and 30b, the thermoplastic polymer may comprise Thermoplastic polyurethane (TPU), and/or Polyvinyl chloride (PVC), and/or any other thermoplastic polymer suitable for the intended aim(s). Furthermore, in some examples, the electrically conductive particles 307 may be graphite particles or any other type of electrically conductive particles suitable for the intended aim(s). The thermoplastic polymer film may be obtained by extruding pellets.

If the thermoplastic polymer and the electrically conductive particles are combined under a suitable mixing ratio, a desired electrical conductivity of the layers 302, 304 may be achieved while keeping good welding capabilities. An aspect of the proposed electro-stimulation circuits is thus that they may be easily welded to a region of the cuff, due to the presence of the thermoplastic polymer, in such a way that skin friendly current transmissions may occur due to the presence of the electrically conductive particles.

According to examples, the second layer may comprise an electrically conductive fabric, which may be at least partially made of carbon fibre and/or may be at least partially made of metallic mesh. The layer made of thermoplastic polymer doped with electrically conductive particles may still have a relatively low nominal value of electrical conductivity which may be not enough for the track portion to conduct electricity to/from the electrode portion efficiently.

The proposed second layer made of electrically conductive fabric may provide a good electrical conductivity for the track portion to conduct electricity to/from the electrode portion in an efficient manner. Hence, a circuit having an electrode portion and a track portion in the form of such a multilayer single film is provided with suitable properties for both the electrode portion and the track portion at the same time. This may reduce complexity and costs of fabrication of said circuits and its application to the industrial manufacturing of electro-stimulation pressure cuffs like the one disclosed in U.S. Pat. No. 5,957,860A.

Figure 31A:
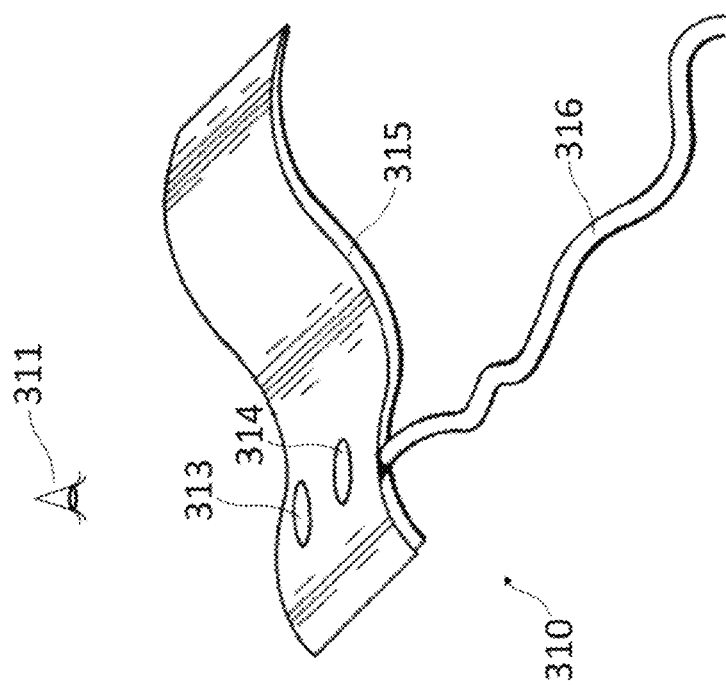
FIG. 31a schematically illustrates a pressure cuff comprising electro-stimulation circuits according to examples.

FIG. 31a schematically illustrates a pressure cuff 310 comprising electro-stimulation circuits according to examples. In particular, this pressure cuff 310 may be configured to be arranged around a limb of a patient and is shown comprising two electro-stimulation circuits. A first of the electro-stimulation circuits may comprise an electrode portion 313 and a track portion (not shown), and a second of the electro-stimulation circuits may comprise an electrode portion 314 and a track portion (not shown).

Each of the two electro-stimulation circuits may be internally attached to the pressure cuff 310 in such a way that, in use, a contact surface of the electrode portion 313, 314 of the electro-stimulation circuit is arranged on a region of the limb, which is at least partially on a peripheral motor nerve of the limb such that an electrical current can be either transmitted or collected by the electrode portion 313, 314 to/from said region of the limb for electro-stimulating the nerve.

The pressure cuff 310 is shown further comprising a fabric cover 315 and a hybrid tube 316 configured to conduct air and electricity between the cuff 310 and e.g. a monitor configured to operate the pressure cuff 310. The fabric cover 315 may comprise a hole for each of the electrode portions 313, 314 of the electro-stimulation circuits in such a way that, in use, a contact surface of the electrode portions 313, 314 are arranged on target regions of the patient for stimulating a peripheral motor nerve.

FIG. 31b schematically illustrates an enlarged view of a region of a pressure cuff similar to the one depicted in FIG. 31a from the point of view 311 indicated in FIG. 31a. A first of the circuits may comprise an electrode portion 319 and a track portion 318, and a second of the circuits may comprise an electrode portion 3112 and a track portion 3111.

The track portion 318 may connect the electrode portion 319 with a corresponding conductive wire of the hybrid tube 316. The track portion 3111 may connect the electrode portion 3112 with a corresponding conductive wire of the hybrid tube 316. The hybrid tube 316 may connect the cuff 310 with a monitor (not shown) for operating the cuff 310. The monitor may have an electricity source (for electro-stimulation) which can thus be connected with the electrode portions 319, 3112 through corresponding conductive wires of the hybrid tube 316 and the track portions 318, 3111 respectively.

The track portions 318, 3111 and the electrode portions 319, 3112 are depicted with dashed lines to indicate that they are attached to an internal side of the fabric cover 315 and, therefore, they are not visible in the view provided by FIG. 31b. The fabric cover is shown having an opening 310 through which current transmissions between the electrode portion 319 and the patient's skin can occur. The fabric cover is shown having another opening 3113 through which current transmissions between the electrode portion 3112 and the patient's skin can occur.

FIG. 32 schematically illustrates a cross sectional view 323 of a pressure cuff region similar to the one shown in FIG. 31b. This view 323 has been taken according to a plane AA indicated in FIG. 31b. FIG. 32 comprises a view 322 similar to the view of FIG. 31b and dashed lines of reference for better understanding of the cross sectional view 323.

The fabric cover 315 is shown formed as a multilayer fabric having an outer layer 320 made of e.g. nylon and an inner layer 321 made of e.g. thermoplastic polymer. The outer layer of nylon 320 may generally attribute enough strength to the cuff 310 for supporting its normal manipulation by medical operators.

The inner layer of thermoplastic polymer 321 may permit a relatively strong attachment of the electro-stimulation circuits 318, 319, 3111, 3112 to the cuff, and can contribute to making the inflatable bag of the pressure cuff leak-proof. Hence, a relatively compact and resistant pressure cuff may be obtained with the proposed multilayer fabric cover 315.

The multilayer fabric cover 315 may be obtained with a heated lamination process similar to the one described for fabricating the multilayer base material of the electro-stimulation circuits. As commented with respect to the multilayer base material for the electro-stimulation circuits, the use of a heated lamination process for fabricating the multilayer fabric cover 315 may be that adhesives or similar substances may not be required, such that a skin friendly multilayer fabric cover 315 may be obtained.

Another aspect of using this heated lamination process for manufacturing the multilayer fabric cover 315 may be that the fabrication process may result easier and cheaper in comparison with other types of processes, such as e.g. a multi-material thin-film hot co-extrusion process. A further aspect of using this heated lamination process may be that a relatively thin, leak-tight, efficient, and cost-effective multilayer fabric cover 315 may be obtained.

In the particular case of FIG. 32, the electro-stimulation circuits 318, 319, 3111, 3112 are shown formed as a single multilayer film with three layers 302-304 similar to the layered structure of FIG. 30b. FIG. 32 shows that the electro-stimulation circuits may be attached to the fabric cover 315 through the welding of the thermoplastic polymer layer 302 of the electro-stimulation circuits and the thermoplastic polymer layer 321 of the fabric cover 315.

The welding of the thermoplastic polymer layer 302 of the electro-stimulation circuits and the thermoplastic polymer layer 321 of the fabric cover 315 may be performed through a hot plate welding process. Alternatively, this welding may be performed through an ultrasound welding process. In further alternative implementations, this welding may be performed through a radio frequency welding process.

A radio frequency welding process is based on generating a high-frequency electric flux across the thermoplastic polymer layers to be welded while they are kept together under pressure between an Electrode and a counter-Electrode metallic plate. This electric flux may cause the vibration of the inner molecules of both thermoplastic polymer layers, and said vibration may cause a local temperature increase at the contact interface existing between the two layers to be welded.

Therefore, an advantageous aspect of using a radio frequency welding process may be that it may effectively avoid the appearance of creases, fissures and/or deformations on the outer surface of the materials to be welded. This may be due to that the radio frequency welding process only applies heat at the specific contact interface between the two layers to be welded, while the rest of the layers are kept at room temperature.

The multilayer fabric cover 315 is shown comprising corresponding holes 3110, 3113 through which skin friendly current transmissions can occur between the electrode portions 319, 3112 and the skin of the patient. As commented before, the electrically conductive layer 303, which may be made of carbon fibre, and/or metallic mesh, and/or any other material suitable for the intended aim(s), may be connected with corresponding conductive wires comprised in the hybrid tube 316.

FIG. 32 further shows corresponding regions 318', 3111' of the track portions 318, 3111 respectively and their attachment with the fabric cover 315 of the pressure cuff 310 through corresponding thermoplastic polymer layers 302, 321.

Any of the principles used for constructing electro-stimulation circuits described in relation to FIGS. 30a-32 can be used for fabricating any of the pressure cuffs described with reference to FIGS. 27a-29b.

Although only a number of examples have been disclosed herein, other alternatives, modifications, uses and/or equivalents thereof are possible. Furthermore, all possible combinations of the described examples are also covered. Thus, the scope of the present disclosure should not be limited by the particular examples.

Clause 1. A method is provided for automated determination of a neuromuscular blockade status for a patient to whom a muscle relaxant has been delivered, wherein a plurality of neuromuscular blockade statuses are predefined, and for each of the neuromuscular blockade statuses are predefined one or more stimulation cycles with a cycle periodicity and one or more criterions for changing from the neuromuscular blockade status to another neuromuscular blockade status, said criterions including a first criterion or first set of criterions for changing the neuromuscular blockade status to a first other neuromuscular blockade status;

the method comprising:

automatically performing one or more stimulation cycles predefined for the neuromuscular blockade status;

automatically determining one or more muscle responses to at least some of the performed stimulation cycles;

automatically comparing the muscle responses with the predefined criterions for changing the neuromuscular blockade status; and if the muscle responses fulfil the predefined first criterion or first set of criterions, then automatically performing one or more stimulation cycles predefined for the first other neuromuscular blockade status.

Clause 2. A method according to clause 1, wherein for one or more of the neuromuscular blockade statuses, the one or more criterions for changing from the neuromuscular blockade status to another neuromuscular blockade status further comprise:

a second criterion or second set of criterions for changing the neuromuscular blockade status to a second other neuromuscular blockade status; wherein if the muscle responses fulfil the predefined second criterion or second set of criterions, then automatically performing one or more stimulation cycles predefined for the second other neuromuscular blockade status.

Clause 3. A method according to any of clauses 1 or 2, wherein the plurality of neuromuscular blockade statuses comprises an induction status, a moderate status, a deep status, an intense status, and optionally a reversion status and an end-of-reversion status.

Clause 4. A method according to clause 3, wherein the one or more predefined stimulation cycles comprise a predefined stimulation cycle according to a Single Twitch (ST) pattern based on generating a single ST stimulation pulse, such that a muscle response to a performed ST stimulation cycle has a single ST response pulse induced by the ST stimulation pulse, and a ST-ratio parameter corresponding to the percentage of the ST response pulse with respect to a ST response pulse of reference determined before delivering the muscle relaxant to the patient.

Clause 5. A method according to clause 4, wherein the induction status has the ST stimulation cycle predefined with a cycle periodicity in a range of 0.5-2 seconds, and preferably equal to approximately 1 second.

Clause 6. A method according to clause 5, wherein the first set of criterions of the induction status comprises an ST-ratio of the ST stimulation cycle for changing the neuromuscular blockade status from the induction status to the moderate status.

Clause 7. A method according to clause 3, wherein the one or more predefined stimulation cycles comprise a predefined stimulation cycle according to a Train of four (TOF) pattern based on generating first, second, third and fourth TOF stimulation pulses, such that a muscle response to a performed TOF stimulation cycle has first, second, third and fourth TOF response pulses induced by the first, second, third and fourth TOF stimulation pulses respectively, a TOF-count parameter corresponding to the number of TOF response pulses with amplitude greater than zero in the TOF muscle response, and a TOF-ratio parameter corresponding to the percentage of the fourth TOF response pulse with respect to the first TOF response pulse.

Clause 8. A method according to clause 7, wherein the induction status has the TOF stimulation cycle predefined with a cycle periodicity in a range of 8-20 seconds, preferably equal to approximately 12 seconds.

Clause 9. A method according to clause 8, wherein the first set of criterions of the induction status comprises a TOF-count less than 4, in which case the neuromuscular blockade status is changed from the induction status to the moderate status.

Clause 10. A method according to any of clauses 8 or 9, wherein the first set of criterions of the induction status comprises a TOF-ratio less than between 25% and 35%, and preferably less than 30%, during between 3 and 7 minutes, and preferably during 5 minutes, in which case the neuromuscular blockade status is changed from the induction status to the moderate status.

Clause 11. A method according to any of clauses 8 to 10, wherein the first set of criterions of the induction status comprises the neuromuscular blockade status having been the induction status during between 12 and 18 minutes, and preferably during approximately 15 minutes, in which case the neuromuscular blockade status is changed from the induction status to an unblocked status.

Clause 12. A method according to any of clauses 7 to 11, wherein the moderate status has the TOF stimulation cycle predefined with a cycle periodicity in a range of 30 seconds-2 minutes, and preferably equal to approximately 1 minute.

Clause 13. A method according to clause 12, wherein the first set of criterions of the moderate status comprises whether two consecutive TOF-counts are equal to 0, in which case the neuromuscular blockade status is changed from the moderate status to the deep status.

Clause 14. A method according to any of clauses 12 or 13, wherein the first set of criterions of the moderate status comprises a TOF-ratio greater than or equal to between 2% and 6%, and preferably greater than or equal to approximately 4%, in which case the neuromuscular blockade status is changed from the moderate status to the reversion status.

Clause 15. A method according to any of clauses 12 to 14, wherein the first set of criterions of the moderate status comprises a TOF-ratio greater than or equal to between 75% and 85%, and preferably greater than or equal to approximately 80%, in which case the neuromuscular blockade status is changed from the moderate status to the end-of-reversion status.

Clause 16. A method according to any of clauses 12 to 15, wherein the first set of criterions of the moderate status comprises a TOF-ratio greater than or equal to between 40% and 60%, and preferably greater than or equal to approximately 50%, in which case the neuromuscular blockade status is changed from the moderate status to the reversion status.

Clause 17. A method according to any of clauses 12 to 16, wherein the first set of criterions of the moderate status comprises a TOF-ratio greater than or equal to X %+MIN-TOF-ratio, in which case the neuromuscular blockade status is changed from the moderate status to the reversion status;

wherein X % is in a range of 20%-30%, and preferably equal to approximately 25%, and MIN-TOF-ratio is the smallest TOF-ratio determined during the moderate status.

Clause 18. A method according to any of clauses 7 to 17, wherein the reversion status has the TOF stimulation cycle predefined with a cycle periodicity in a range of 30 seconds-1 minute, and preferably equal to approximately 1 minute.

Clause 19. A method according to clause 18, wherein the first set of criterions of the reversion status comprises a TOF-ratio greater than or equal to between 75% and 85%, and preferably greater than or equal to approximately 80%, in which case the neuromuscular blockade status is changed from the reversion status to the end-of-reversion status.

Clause 20. A method according to any of clauses 18 or 19, wherein the first set of criterions of the reversion status comprises two consecutive TOF-counts are less than 4, in which case the neuromuscular blockade status is changed from the reversion status to the moderate status.

Clause 21. A method according to any of clauses 18 to 20, wherein the first set of criterions of the reversion status comprises four TOF-counts less than between 25% and 35%, and preferably less than approximately 30%, in which case the neuromuscular blockade status is changed from the reversion status to the moderate status.

Clause 22. A method according to any of clauses 7 to 21, wherein the end-of-reversion status has the TOF stimulation cycle predefined with a cycle periodicity in a range of 20-40 seconds, and preferably equal to approximately 30 seconds.

Clause 23. A method according to clause 22, wherein the first set of criterions of the end-of-reversion status comprises a TOF-ratio less than between 55% and 65%, and preferably less than approximately 60%, in which case the neuromuscular blockade status is changed from the end-of-reversion status to the reversion status.

Clause 24. A method according to any of clauses 22 or 23, wherein the first set of criterions of the end-of-reversion status comprises two consecutive TOF-counts less than 4, in which case the neuromuscular blockade status is changed from the end-of-reversion status to the moderate status.

Clause 25. A method according to any of clauses 22 to 24, wherein the first set of criterions of the end-of-reversion status comprises four TOF-ratios less than between 25% and 35%, and preferably less than approximately 30%, in which case the neuromuscular blockade status is changed from the end-of-reversion status to the moderate status.

Clause 26. A method according to any of clauses 22 to 25, wherein the first set of criterions of the end-of-reversion status comprises a TOF-ratio counter greater than or equal to 5, in which case the neuromuscular blockade status is changed from the end-of-reversion status to an unblocked status;

wherein said TOF-ratio counter is calculated based on the following rules:

initializing the counter=0;
if 91%≤TOF-ratio 94%, adding 1 to the counter;
if 95%≤TOF-ratio 98%, adding 2 to the counter;
if TOF-ratio≥99%, adding 3 to the counter.

Clause 27. A method according to any of clauses 7 to 26, wherein the deep status has the TOF stimulation cycle predefined with a cycle periodicity in a range of 1-5 minutes, and preferably equal to approximately 2 minutes.

Clause 28. A method according to any of clauses 7 to 26, wherein the deep status has the TOF stimulation cycle predefined with a cycle periodicity in a range of 20-40 seconds, and preferably equal to approximately 30 seconds.

Clause 29. A method according to any of clauses 27 or 28, wherein the first set of criterions of the deep status comprises a TOF-count greater than zero, in which case the neuromuscular blockade status is changed from the deep status to the moderate status.

Clause 30. A method according to any of clauses 27 to 29, wherein the first set of criterions of the deep status comprises a TOF-ratio greater than or equal to between 5% and 9%, and preferably equal to approximately 7%, in which case the neuromuscular blockade status is changed from the deep status to the reversion status.

Clause 31. A method according to any of clauses 27 to 30, wherein the first set of criterions of the deep status comprises a TOF-ratio greater than or equal to between 75% and 85%, and preferably equal to approximately 80%, in which case the neuromuscular blockade status is changed from the deep status to the end-of-reversion status.

Clause 32. A method according to any of clauses 7 to 31, wherein the intense status has the TOF stimulation cycle predefined with a cycle periodicity in a range of 2-5 minutes, and preferably equal to approximately 2 minutes.

Clause 33. A method according to any of clauses 7 to 31, wherein the intense status has the TOF stimulation cycle predefined with a cycle periodicity in a range of 20-40 seconds, and preferably equal to approximately 30 seconds.

Clause 34. A method according to any of clauses 32 or 33, wherein the first set of criterions of the intense status comprises a TOF-count greater than zero, in which case the neuromuscular blockade status is changed from the intense status to the moderate status.

Clause 35. A method according to any of clauses 32 to 34, wherein the first set of criterions of the intense status comprises a TOF-ratio greater than or equal to between 5% and 15%, and preferably greater than or equal to approximately 10%, in which case the neuromuscular blockade status is changed from the intense status to the reversion status.

Clause 36. A method according to any of clauses 32 to 35, wherein the first set of criterions of the intense status comprises a TOF-ratio greater than or equal to between 75% and 85%, and preferably equal to approximately 80%, in which case the neuromuscular blockade status is changed from the intense status to the end-of-reversion status.

Clause 37. A method according to any of clauses 7 to 36 and to clause 2, wherein the one or more predefined stimulation cycles further comprise a predefined stimulation cycle according to a Post-tetanic count (PTC) pattern based on a tetanus stimulation during between 2 and 8 seconds, and preferably during approximately 5 seconds, followed by a period of single twitch (ST) pulses of between 10 and 20 seconds, and preferably of approximately 15 seconds, such that a muscle response to a performed PTC stimulation cycle has PTC response pulses induced by the ST pulses of the PTC stimulation cycle, and a FTC-count parameter corresponding to the number of PTC response pulses with amplitude greater than zero in the PTC muscle response.

Clause 38. A method according to clause 37, wherein each of the deep status and intense status has the PTC stimulation cycle predefined with a cycle periodicity in a range of 6-15 minutes, and preferably equal to approximately 6 minutes.

Clause 39. A method according to any of clauses 37 or 38, wherein the second set of criterions of the deep status comprises a FTC-count less than or equal to between 3 and 5, and preferably less than or equal to approximately 4, in which case the neuromuscular blockade status is changed from the deep status to the intense status.

Clause 40. A method according to any of clauses 37 to 39, wherein the second set of criterions of the intense status comprises a PTC-count greater than or equal to between 6 and 10, and preferably greater than or equal to approximately 8, in which case the neuromuscular blockade status is changed from the intense status to the deep status.

Clause 41. A method according to any of clauses 4 to 40, wherein:

the one or more muscle responses are determined through a pressure cuff applied to the patient, such that any muscle response has a form of a pressure wave representative of how pressure varies over time in the cuff as a result of a muscle reaction to corresponding performed stimulation cycle.

Clause 42. A method according to clause 41, further comprising:

determining the end of a heartbeat of the patient; and wherein the first TOF stimulation pulse is generated substantially at the end of the heartbeat of the patient.

Clause 43. A method according to clause 42, further comprising:

determining a first characteristic indicative of the shape of the upward slope of the first TOF response pulse; and for at least some further TOF response pulse included in the second, third and fourth TOF response pulses:

determining the first characteristic of the further TOF response pulse;

determining a deviation between the first characteristic of the further TOF response pulse and the first characteristic of the first TOF response pulse;

verifying if the deviation exceeds a deviation threshold, and, in case of a negative result of the verification, adjusting the further TOF response pulse by assuming that the time until peak of the further TOF response pulse is measured correctly and that the shape of its upward slope can be described by the first characteristic of the first TOF response pulse.

Clause 44. A method according to clause 43, further comprising:

in case of a positive result of the verification, adjusting the further TOF response pulse either based on a first assumption that the time until peak of the further TOF response pulse is measured correctly and that the shape of its upward slope can be described by the first characteristic of the first TOF response pulse, or based on a second assumption that the time until peak of the further TOF response pulse is measured correctly and that the shape of its upward slope can be described by substantially subtracting a heartbeat pulse of reference from the further TOF response pulse.

Clause 45. A method is provided for determining a muscle response to an electro-stimulation of the muscle in a patient, the method comprising:

determining the end of a heartbeat of the patient;

performing the electro-stimulation of the muscle by causing generation of a first electro-stimulation pulse and, subsequently, one or more further electro-stimulation pulses, the first electro-stimulation pulse being generated substantially at the end of the heartbeat;

determining the muscle response in the form of a pressure wave representing how pressure varies over time in a pressure cuff as a muscle reaction to the electro-stimulation, the pressure wave comprising first and further pressure pulses induced by the first and further electro-stimulation pulses respectively;

determining a first characteristic indicative of the shape of the upward slope of the first pressure pulse; and for at least some of the further pressure pulses:

determining the first characteristic of the further pressure pulse;

determining a deviation between the first characteristic of the further pressure pulse and the first characteristic of the first pressure pulse;

verifying if the deviation exceeds a deviation threshold, and,

In case of a negative result of the verification, adjusting the further pressure pulse by assuming that the time until peak of the further pressure pulse is measured correctly and that the shape of its upward slope can be described by the first characteristic of the first pressure pulse.

Clause 46. A method according to clause 45, wherein the at least some of the further pressure pulses comprises all the further pressure pulses of the pressure wave.

Clause 47. A method according to any of clauses 45 or 46, wherein the first characteristic of a pressure pulse is determined depending on an amplitude of the pressure pulse and a maximum derivative of the upward slope of the pressure pulse.

Clause 48. A method according to clause 47, wherein the first characteristic of the pressure pulse is determined based on the following formula:

$$C(\text{pulse}) = \frac{A(\text{pulse})}{d_{max}(\text{pulse})}$$

wherein: $C(\text{pulse})$ is the first characteristic of the pressure pulse, $A(\text{pulse})$ is the amplitude of the pressure pulse, and $d_{max}(\text{pulse})$ is the maximum derivative of the upward slope of the pressure pulse.

Clause 49. A method according to clause 48, wherein adjusting the further pressure pulse comprises:

adjusting an amplitude of the further pressure pulse based on the following formula:

$$A_{adjusted}(\text{further\_pulse}) = C(\text{first\_pulse}) \times d_{max}(\text{further\_pulse})$$

wherein: $A_{adjusted}(\text{further\_pulse})$ is the adjusted amplitude of the further pressure pulse, $C(\text{first\_pulse})$ is the first characteristic of the first pressure pulse, and $d_{max}(\text{further\_pulse})$ is the maximum derivative of the upward slope of the further pressure pulse.

Clause 50. A method according to any of clauses 44 to 48, wherein the deviation threshold is in a range of 10%-20%, preferably equal to 15%.

Clause 51. A method according to any of clauses 45 to 50, further comprising:

in case of a positive result of the verification, adjusting the further pressure pulse either based on a first assumption that the time until peak of the further pressure pulse is measured correctly and that the shape of its upward slope can be described by the first characteristic of the first pressure pulse, or based on a second assumption that the time until peak of the further pressure pulse is measured correctly and that the shape of its upward slope can be described by substantially subtracting a heartbeat pulse of reference from the measured further pressure pulse.

Clause 52. A method according to clause 51, wherein adjusting the further pressure pulse based on the first assumption comprises:

determining a first adjusted amplitude of the further pressure pulse based on the first assumption.

Clause 53. A method according to clause 52, wherein the first adjusted amplitude of the further pressure pulse is determined based on the following formula:

$$A_{adjusted}(\text{further\_pulse}) = C(\text{first\_pulse}) \times d_{max}(\text{further\_pulse})$$

wherein: $A_{adjusted}(\text{further\_pulse})$ is the first adjusted amplitude of the further pressure pulse, $C(\text{first\_pulse})$ is the first characteristic of the first pressure pulse, and $d_{max}(\text{further\_pulse})$ is the maximum derivative of the upward slope of the further pressure pulse.

Clause 54. A method according to any of clauses 51 to 53, wherein adjusting the further pressure pulse based on the second assumption comprises:

determining a second adjusted amplitude of the further pressure pulse based on the second assumption.

Clause 55. A method according to clause 54, wherein the second adjusted amplitude of the further pressure pulse is determined depending on a second characteristic of the shape of the upward slope of the heartbeat pulse of reference.

Clause 56. A method according to clause 55, wherein the second characteristic is determined depending on an amplitude of the heartbeat pulse of reference and a time until peak of the heartbeat pulse of reference.

Clause 57. A method according to clause 56, wherein the second characteristic is determined based on the following formula:

$$C(\text{hb\_pulse}) = \frac{A(\text{hb\_pulse})}{t_S(\text{hb\_pulse})}$$

wherein: $C(\text{hb\_pulse})$ is the second characteristic of the heartbeat pulse of reference, $A(\text{hb\_pulse})$ is the amplitude of the heartbeat pulse of reference, and $t_S(\text{hb\_pulse})$ is the time until peak of the heartbeat pulse of reference.

Clause 58. A method according to any of clauses 54 to 57, wherein the second adjusted amplitude of the further pressure pulse is determined further depending on the amplitude of the further pressure pulse and the time until peak of the further pressure pulse.

Clause 59. A method according to clause 58, wherein the second adjusted amplitude of the further pressure pulse is determined based on the following formula:

$$A_{adjusted}(\text{further\_pulse}) = A(\text{further\_pulse}) - t_S(\text{further\_pulse}) \times C(\text{hb\_pulse})$$

wherein: $A_{adjusted}(\text{further\_pulse})$ is the second adjusted amplitude of the further pressure pulse, $A(\text{further\_pulse})$ is the amplitude of the further pressure pulse, $t_S(\text{further\_pulse})$ is the time until peak of the further pressure pulse, and $C(\text{hb\_pulse})$ is the second characteristic of the heartbeat pulse of reference.

Clause 60. A method according to any of clauses 52 or 53 and to any of clauses 54 to 59, wherein adjusting the further pressure pulse either based on the first assumption or based on the second assumption comprises:

adjusting the amplitude of the further pressure pulse by selecting the smaller of the first and second adjusted amplitudes.

Clause 61. A method according to any of clauses 45 to 60, wherein:

the electro-stimulation is performed according to a Train of four (TOF) pattern which is based on generating a first electro-stimulation pulse and three further electro-stimulation pulses; and wherein:

determining the muscle response further comprises determining a TOF-ratio parameter corresponding to a relation between the amplitude of one of the three further pressure pulses and the amplitude of the first pressure pulse.

Clause 62. A method according to clause 61, wherein determining the TOF-ratio parameter comprises:

verifying that $A(\text{first\_pulse}) \geq A(\text{second\_pulse}) \geq A(\text{third\_pulse}) \geq A(\text{fourth\_pulse})$, in which case, the TOF-ratio parameter is the percentage of the fourth_pulse with respect to the first_pulse; wherein:

first_pulse is the first pulse in the pressure wave, and $A(\text{first\_pulse})$ is the amplitude of said first pulse;

fourth_pulse is the fourth pulse in the pressure wave, and $A(\text{fourth\_pulse})$ is the amplitude of said fourth pulse;

$A(\text{second\_pulse})$ is the amplitude of the second pulse in the pressure wave; and $A(\text{third\_pulse})$ is the amplitude of the third pulse in the pressure wave.

Clause 63. A method according to any of clauses 61 or 62, wherein determining the TOF-ratio parameter comprises:

verifying that $A(\text{first\_pulse}) \geq A(\text{second\_pulse}) \geq A(\text{third\_pulse}) < A(\text{fourth\_pulse})$, in which case, the TOF-ratio parameter is determined based on the following formula:

$$TOF_{RATIO} = \left(\frac{A(\text{third\_pulse})}{A(\text{first\_pulse})}\right)^X$$

wherein:

$TOF_{RATIO}$ is the TOF-ratio parameter;

$A(\text{first\_pulse})$ is the amplitude of the first pulse in the pressure wave;

$A(\text{second\_pulse})$ is the amplitude of the second pulse in the pressure wave;

A(third_pulse) is the amplitude of the third pulse in the pressure wave;

A(fourth_pulse) is the amplitude of the fourth pulse in the pressure wave; and

X is a value used to compensate that the TOF-ratio parameter is calculated depending on the amplitude of the first and third pulses rather than on the amplitude of the first and fourth pulse.

Clause 64. A method according to any of clauses 61 to 63, wherein determining the TOF-ratio parameter comprises:

verifying that A(first_pulse)≥A(second_pulse)<A(third_pulse)<A(fourth_pulse), in which case, the TOF-ratio parameter is determined based on the following formula:

$$TOF_{RATIO} = \left(\frac{A(\text{second\_pulse})}{A(\text{first\_pulse})}\right)^Y$$

wherein:

$TOF_{RATIO}$ is the TOF-ratio parameter;

A(first_pulse) is the amplitude of the first pulse in the pressure wave;

A(second_pulse) is the amplitude of the second pulse in the pressure wave;

A(third_pulse) is the amplitude of the third pulse in the pressure wave;

A(fourth_pulse) is the amplitude of the fourth pulse in the pressure wave; and

Y is a value used to compensate that the TOF-ratio parameter is calculated depending on the amplitude of the first and second pulses rather than the amplitude of the first and fourth pulses.

Clause 65. An electro-stimulation electrode configured to be applied dryly on the skin of a patient, comprising:

a support layer made of an electrically insulating material and having at least one region with one or more holes, wherein a first surface of the support layer is arranged in such a way that, in use, it contacts the patient's skin;

an electrically conductive medium adhered to a second surface of the support layer, opposite to the first surface, and arranged completely or partially surrounding the region with holes in such a way that the electrically conductive medium does not cover the region with holes; and a first conductive layer contacting the electrically conductive medium in such a way that the first conductive layer covers the region with holes.

Clause 66. An electro-stimulation electrode according to clause 65, wherein the first conductive layer is made of a conductive composite or an intrinsically conductive polymer.

Clause 67. An electro-stimulation electrode according to any of clauses 65 or 66, wherein the electrically conductive medium is arranged between the support layer and the first conductive layer.

Clause 68. An electro-stimulation electrode according to clause 67, further comprising a second conductive layer arranged on the first surface of the support layer in such a way that the second conductive layer contacts the first conductive layer through at least one of the holes.

Clause 69. An electro-stimulation electrode according to clause 68, wherein the second conductive layer is made of a conductive composite or an intrinsically conductive polymer.

Clause 70. An electro-stimulation electrode according to any of clauses 68 or 69, wherein the second conductive layer has a flat shape, or a convex shape, or a shape provided with relief at the level of the region with the at least one hole.

Clause 71. An electro-stimulation electrode according to any of clauses 65 or 66, wherein the first conductive layer is arranged between the electrically conductive medium and the support layer.

Clause 72. An electro-stimulation electrode according to clause 71, further comprising a second conductive layer arranged between the first conductive layer and the support layer, said second layer covering at least one of the holes of the support layer.

Clause 73. An electro-stimulation electrode according to clause 72, wherein the second conductive layer is made of a conductive composite or an intrinsically conductive polymer.

Clause 74. An electro-stimulation electrode according to any of clauses 72 or 73, wherein the second conductive layer has a flat shape, or a convex shape, or a shape provided with relief at the level of the region with holes.

Clause 75. An electro-stimulation electrode according to any of clauses 72 to 74, further comprising a third conductive layer arranged between the first conductive layer and the second conductive layer, wherein the third conductive layer has an outline substantially complementary to the outline of the holes, and the third conductive layer is arranged coincident with the holes.

Clause 76. An electro-stimulation electrode according to clause 75, wherein the third conductive layer is made of a conductive composite or an intrinsically conductive polymer.

Clause 77. An electro-stimulation electrode according to any of clauses 75 or 76, wherein the first, second and third conductive layers have an aggregate thickness in a range of 160-200 microns.

Clause 78. An electro-stimulation electrode according to any of clauses 71 to 77, further comprising an inner covering layer having an outline exceeding the first and second conductive layers.

Clause 79. An electro-stimulation electrode according to any of clauses 65 to 78, wherein the support layer is a nylon fabric or a paper fabric or a nonwoven fabric.

Clause 80. An electro-stimulation electrode according to any of clauses 65 to 79, wherein the electrically conductive medium is an electrically conductive track or cable.

Clause 81. An electro-stimulation electrode according to clause 80, wherein the electrically conductive track is an electrically conductive metallic fabric or a printed electrically conductive ink.

Clause 82. An electro-stimulation electrode according to any of clauses 65 to 81, wherein the electrically conductive medium completely surrounds the region with holes.

Clause 83. A pressure cuff comprising at least an electro-stimulation electrode according to any of clauses 65 to 82.

Clause 84. A hybrid air-signal connector is provided for connecting an air-signal tube to an electro-stimulation cuff, the hybrid air-signal connector comprising a main body having a base with a first tubular portion arranged on a first face of the base in such a way that, in use, the first tubular portion is fitted into an air conduit of the air-signal tube such that air can flow between the air conduit and the inside of the cuff through the first tubular portion; and two connection electrodes which are either L-shaped or substantially flat, each having an external terminal arranged in such a way that, in use, the external terminal contacts an electrically conductive cable of the air-signal tube, and an internal terminal embedded in the base with an end portion arranged on the first face of the base in such a way that, in use, this end portion contacts an inner conductive track of the cuff when the hybrid air-signal connector is introduced into a connection bore of the cuff; wherein in the case of the L-shaped connection electrodes, the external terminals extend from the base parallel to the first tubular portion, or in the case of the substantially flat connection electrodes, the external terminals are embedded in the base.

Clause 85. A hybrid air-signal connector according to clause 84, comprising a second tubular portion outwardly coaxially arranged with respect to the first tubular portion in such a way that, in use, the second tubular portion protects the external terminals, acts as a guide for connecting the air-signal tube to the air-signal connector, and avoids the intrusion of liquids and/or dust in said connection.

Clause 86. A hybrid air-signal connector according to clause 85, wherein the second tubular portion has a length smaller than the length of the first tubular portion.

Clause 87. A hybrid air-signal connector according to any of clauses 84 to 86, which is constituted by only three single bodies: the main body and the two electrodes.

Clause 88. A hybrid air-signal connector according to any of clauses 84 to 87, wherein, in the case of the L-shaped electrodes, the external terminals have a cylindrical shape and the internal terminals are substantially flat.

Clause 89. A hybrid air-signal connector according to any of clauses 84 to 88, wherein the base comprises a central ring configured to provide pneumatic air tightness, and wherein the central ring protrudes with respect to the first face of the base.

Clause 90. A hybrid air-signal connector according to any of clauses 84 to 89, comprising at the face of the base opposite to the first face holes for accessing to the end portions of the internal terminals.

Clause 91. A hybrid air-signal connector according to any of clauses 84 to 90, wherein the electrodes are asymmetrically arranged.

Clause 92. A hybrid air-signal connector according to any of clauses 84 to 91, wherein the main body is made of polyurethane.

Clause 93. A hybrid air-signal connector according to any of clauses 84 to 92, wherein the base has a substantially elliptical shape.

Clause 94. A hybrid air-signal connector according to any of clauses 84 to 93, wherein:

the first tubular portion has a length of approximately 16 mm and a diameter of approximately 3 mm;

the external terminals have, in the case of the L-shaped electrodes, a length of approximately 7 mm and a diameter of approximately 1 mm;

the external terminals have, in the case of the flat electrodes, a width of approximately 1.5 mm;

the internal terminals have a width of approximately 1.5 mm;

the second tubular portion has a length of approximately 12 mm;

the base is elliptical with an axis of approximately 23 mm and another axis of approximately 28 mm;

the ring for pneumatic air tightness has a diameter of approximately 16 mm;

the end portions of the internal terminals have a length of approximately 4 mm.

Clause 95. A pressure cuff comprising a hybrid air-signal connector according to any of clauses 84 to 94.

Clause 96. A pressure cuff is provided that is configured to be arranged around a limb of a patient, the pressure cuff comprising an active electro-stimulation electrode and a passive electro-stimulation electrode; wherein the active electro-stimulation electrode is configured to transmit an electrical current and arranged in the pressure cuff in such a way that, in use, a contact surface of the active electro-stimulation electrode is arranged on a first region of the limb, which is at least partially on a peripheral motor nerve of the limb such that the nerve receives at least part of the transmitted electrical current; wherein the passive electro-stimulation electrode is configured to collect an electrical current and arranged in the pressure cuff in such a way that, in use, a contact surface of the passive electro-stimulation electrode is arranged on a second region of the limb, such that the transmitted electrical current is collected by the passive electro-stimulation electrode; and wherein the second region of the limb is not on the peripheral motor nerve of the limb, and/or the contact surface of the passive electro-stimulation electrode is substantially larger in size than the contact surface of the active electro-stimulation electrode.

Clause 97. A pressure cuff according to clause 96, wherein the second region of the limb is at least partially on the peripheral motor nerve of the limb; and wherein the contact surface of the passive electro-stimulation electrode is substantially larger in size than the contact surface of the active electro-stimulation electrode.

Clause 98. A pressure cuff according to clause 97, wherein the contact surface of the passive electro-stimulation electrode substantially completely surrounds the contact surface of the active electro-stimulation electrode.

Clause 99. A pressure cuff according to clause 98, wherein the contact surface of the passive electro-stimulation electrode substantially completely surrounds the contact surface of the active electro-stimulation electrode in a substantially coaxial manner.

Clause 100. A pressure cuff according to clause 97, wherein the contact surface of the passive electro-stimulation electrode partially surrounds the contact surface of the active electro-stimulation electrode.

Clause 101. A pressure cuff according to clause 100, wherein the contact surface of the passive electro-stimulation electrode partially surrounds the contact surface of the active electro-stimulation electrode in a substantially coaxial manner.

Clause 102. A pressure cuff according to any of clauses 100 or 101, wherein the contact surface of the passive electro-stimulation electrode is substantially C-shaped.

Clause 103. A pressure cuff according to clause 96, wherein the second region of the limb is not on the peripheral motor nerve; and wherein the contact surface of the passive electro-stimulation electrode is substantially larger in size than the contact surface of the active electro-stimulation electrode.

Clause 104. A pressure cuff according to clause 103, wherein the contact surface of the passive electro-stimulation electrode partially surrounds the contact surface of the active electro-stimulation electrode.

Clause 105. A pressure cuff according to clause 104, wherein the contact surface of the passive electro-stimulation electrode partially surrounds the contact surface of the active electro-stimulation electrode in a substantially coaxial manner.

Clause 106. A pressure cuff according to any of clauses 104 or 105, wherein the contact surface of the passive electro-stimulation electrode is formed as two annular segments each having a first end and a second end, the first ends facing each other with a first gap in between and the second ends facing each other with a second gap in between.

Clause 107. A pressure cuff according to any of clauses 96 to 106, wherein the active electro-stimulation electrode is a first electrode portion of a first electro-stimulation circuit, and the passive electro-stimulation electrode is a second electrode portion of a second electro-stimulation circuit; wherein the first electro-stimulation circuit further comprises a first track portion for conducting the electrical current to the first electrode portion, and the second electro-stimulation circuit further comprises a second track portion for conducting the electrical current from the second electrode portion; wherein the first electrode and track portions are integrally formed as a single multilayer film comprising a layer of thermoplastic polymer doped with electrically conductive particles and a layer of electrically conductive material, said layers being attached to each other; and wherein the second electrode and track portions are integrally formed as a single multilayer film comprising a layer of thermoplastic polymer doped with electrically conductive particles and a layer of electrically conductive material, said layers being attached to each other.

Clause 108. A pressure cuff according to clause 107, wherein each of the first and second electro-stimulation circuits is attached to the pressure cuff by radio frequency welding of a layer of the electro-stimulation circuit made of thermoplastic polymer to a region of the pressure cuff made of thermoplastic polymer.

Clause 109. An electro-stimulation circuit is provided that comprises an electrode portion configured to either transmit or collect an electrical current to/from a region of a patient for electro-stimulating a nerve, and a track portion for conducting the electrical current to/from the electrode portion; wherein the electrode and track portions are integrally formed as a single multilayer film having a plurality of layers; and wherein the plurality of layers comprises a first layer of thermoplastic polymer doped with electrically conductive particles and a second layer of electrically conductive material, the first layer and the second layer being attached to each other.

Clause 110. An electro-stimulation circuit according to clause 109, wherein the plurality of layers further comprises a third layer of thermoplastic polymer attached to the second layer in such a way that the second layer is sandwiched between the first layer and the third layer.

Clause 111. An electro-stimulation circuit according to clause 110, wherein the third layer is made of thermoplastic polymer doped with electrically conductive particles.

Clause 112. An electro-stimulation circuit according to any of clauses 109 to 111, wherein the layers of the plurality of layers are attached together with a heated lamination process.

Clause 113. An electro-stimulation circuit according to any of clauses 109 to 112, wherein the thermoplastic polymer comprises Thermoplastic polyurethane (TPU).

Clause 114. An electro-stimulation circuit according to any of clauses 109 to 113, wherein the thermoplastic polymer comprises Polyvinyl chloride (PVC).

Clause 115. An electro-stimulation circuit according to any of clauses 109 to 114, wherein the electrically conductive particles are graphite particles.

Clause 116. An electro-stimulation circuit according to any of clauses 109 to 115, wherein the second layer comprises an electrically conductive fabric.

Clause 117. An electro-stimulation circuit according to clause 116, wherein the electrically conductive fabric is at least partially made of carbon fibre.

Clause 118. An electro-stimulation circuit according to any of clauses 116 or 117, wherein the electrically conductive fabric is at least partially made of metallic mesh.

Clause 119. A pressure cuff configured to be arranged around a limb of a patient, the pressure cuff comprising at least one electro-stimulation circuit according to any of clauses 109 to 118; wherein the electro-stimulation circuit is attached to the pressure cuff in such a way that, in use, a contact surface of the electrode portion of the electro-stimulation circuit is arranged on a region of the limb, such that an electrical current can be either transmitted or collected by the electrode portion to/from said region of the limb for electro-stimulating a peripheral motor nerve of the limb.

Clause 120. A pressure cuff according to clause 119, wherein the attachment of the electro-stimulation circuit to the pressure cuff comprises an attachment of a layer of the electro-stimulation circuit made of thermoplastic polymer to a region of the pressure cuff made of thermoplastic polymer.

Clause 121. A pressure cuff according to clause 120, wherein the pressure cuff comprises a fabric cover having a layer made of thermoplastic polymer; and wherein the region of the pressure cuff to which the electro-stimulation circuit is attached is comprised in the layer of the fabric cover made of thermoplastic polymer.

Clause 122. A pressure cuff according to clause 121, wherein the fabric cover further comprises a layer made of nylon, paper or nonwoven fabric attached to the layer made of thermoplastic polymer.

Clause 123. A pressure cuff according to clause 122, wherein the layers of the fabric cover are attached together with a heated lamination process.

Clause 124. A pressure cuff according to any of clauses 120 to 123, wherein the layer of the electro-stimulation circuit made of thermoplastic polymer is attached to the region of the pressure cuff made of thermoplastic polymer with a welding process.

Clause 125. A pressure cuff according to clause 124, wherein the welding process is a hot plate welding process.

Clause 126. A pressure cuff according to clause 124, wherein the welding process is an ultrasound welding process.

Clause 127. A pressure cuff according to clause 124, wherein the welding process is a radio frequency welding process.

Clause 128. A pressure cuff according to any of clauses 119 to 127, wherein the at least one electro-stimulation circuit comprises an active electro-stimulation circuit and a passive electro-stimulation circuit; wherein the electrode portion of the active electro-stimulation circuit is an active electro-stimulation electrode, and the electrode portion of the passive electro-stimulation circuit is a passive electro-stimulation electrode; wherein the active electro-stimulation electrode is configured to transmit an electrical current and arranged in the pressure cuff in such a way that, in use, a contact surface of the active electro-stimulation electrode is arranged on a first region of the limb, which is at least partially on a peripheral motor nerve of the limb such that the nerve receives at least part of the transmitted electrical current; wherein the passive electro-stimulation electrode is configured to collect an electrical current and arranged in the pressure cuff in such a way that, in use, a contact surface of the passive electro-stimulation electrode is arranged on a second region of the limb, such that the transmitted electrical current is collected by the passive electro-stimulation electrode; and wherein the second region of the limb is not on the peripheral motor nerve of the limb, and/or the contact surface of the passive electro-stimulation electrode is substantially larger in size than the contact surface of the active electro-stimulation electrode.

Clause 129. A pressure cuff according to clause 128, wherein the track portion of the active electro-stimulation circuit is connected with the active electro-stimulation electrode at one end and with an electricity source at the other end; and wherein the track portion of the passive electro-stimulation circuit is connected with the passive electro-stimulation electrode at one end and with the electricity source at the other end.

Clause 130. An apparatus is provided for determining a muscle response to an electro-stimulation of the muscle in a patient, the apparatus comprising:

a pressure cuff configured to be applied around a limb of the patient, a controller, and a conducting tube connecting the cuff and the controller;

wherein the cuff comprises one or more electrodes for electro stimulating a peripheral motor nerve, the electrodes being arranged on the cuff such that, in use, the electrodes contact the patient's skin when the cuff is applied;

wherein the conducting tube is configured to conduct air in such a way that, in use, the conducting tube propagates air pressure in the cuff to the controller, and configured to conduct electricity in such a way that, in use, the conducting tube conveys electrical pulses from the controller to the electrodes of the cuff; and wherein the controller is configured to send one or more electro-stimulation pulses to the electrodes, to obtain pressure measurements from the cuff as a muscle reaction to the electro-stimulation pulses, and to determine the muscle response to the electro-stimulation of the muscle based on the pressure measurements; and wherein each of the electrodes is either an electro-stimulation electrode according to any of clauses 65-82.

Clause 131. An apparatus according to clause 130, wherein the conducting tube is connected to the pressure cuff through a hybrid air-signal connector according to any of clauses 84-94.

Clause 132. An apparatus according to any of clauses 130 or 131, wherein the pressure cuff is a pressure cuff according to any of clauses 96 to 106.

Clause 133. An apparatus is provided for determining a muscle response to an electro-stimulation of the muscle in a patient, the apparatus comprising:

a pressure cuff configured to be applied around a limb of the patient, a controller, and a conducting tube connecting the cuff and the controller;

wherein the cuff comprises one or more electrodes for electro stimulating a muscle nerve, the electrodes being arranged on the cuff such that, in use, the electrodes contact the patient's skin when the cuff is applied;

wherein the conducting tube is configured to conduct air in such a way that, in use, the conducting tube propagates air pressure in the cuff to the controller, and configured to conduct electricity in such a way that, in use, the conducting tube conveys electrical pulses from the controller to the electrodes of the cuff; and wherein the controller is configured to send one or more electro-stimulation pulses to the electrodes, to obtain pressure measurements from the cuff as a muscle reaction to the electro-stimulation pulses, and to determine the muscle response to the electro-stimulation of the muscle based on the pressure measurements; and wherein the pressure cuff is a pressure cuff according to any of clauses 119 to 127.

Clause 134. An apparatus according to clause 133, wherein the conducting tube is connected to the pressure cuff through a hybrid air-signal connector according to any of clauses 84-94.

Clause 135. An apparatus according to any of clauses 133 or 134, wherein the pressure cuff is further according to any of clauses 96 to 108.

Clause 136. An apparatus is provided for determining a muscle response to an electro-stimulation of the muscle in a patient, the apparatus comprising:

a pressure cuff configured to be applied around a limb of the patient, a controller, and a conducting tube connecting the cuff and the controller;

wherein the cuff comprises one or more electrodes for electro stimulating a muscle nerve, the electrodes being arranged on the cuff such that, in use, the electrodes contact the patient's skin when the cuff is applied;

wherein the conducting tube is configured to conduct air in such a way that, in use, the conducting tube propagates air pressure in the cuff to the controller, and configured to conduct electricity in such a way that, in use, the conducting tube conveys electrical pulses from the controller to the electrodes of the cuff; and wherein the controller is configured to send one or more electro-stimulation pulses to the electrodes, to obtain pressure measurements from the cuff as a muscle reaction to the electro-stimulation pulses, and to determine the muscle response to the electro-stimulation of the muscle based on the pressure measurements; and wherein the conducting tube is connected to the pressure cuff through a hybrid air-signal connector according to any of clauses 84-94.

Clause 137. An apparatus according to 136, wherein the pressure cuff is a pressure cuff according to any of clauses 96 to 106.

Clause 138. An apparatus is provided for determining a muscle response to an electro-stimulation of the muscle in a patient, the apparatus comprising:

a pressure cuff configured to be applied around a limb of the patient, a controller, and a conducting tube connecting the cuff and the controller;

wherein the cuff comprises one or more electrodes for electro stimulating a muscle nerve, the electrodes being arranged on the cuff such that, in use, the electrodes contact the patient's skin when the cuff is applied;

wherein the conducting tube is configured to conduct air in such a way that, in use, the conducting tube propagates air pressure in the cuff to the controller, and configured to conduct electricity in such a way that, in use, the conducting tube conveys electrical pulses from the controller to the electrodes of the cuff; and wherein the controller is configured to send one or more electro-stimulation pulses to the electrodes, to obtain pressure measurements from the cuff as a muscle reaction to the electro-stimulation pulses, and to determine the muscle response to the electro-stimulation of the muscle based on the pressure measurements; and wherein the pressure cuff is a pressure cuff according to any of clauses 96 to 106.

What is claimed is:

1. A method of determining a muscle response to an electro-stimulation of the muscle in a patient, the method comprising:
   determining the end of a heartbeat of the patient;
   performing the electro-stimulation of the muscle by causing a generation of a first electro-stimulation pulse and, subsequently, one or more further electro-stimulation pulses, the first electro-stimulation pulse being generated substantially at the end of the heartbeat;
   determining the muscle response in the form of a pressure wave representing how pressure varies over time in a pressure cuff as a muscle reaction to the electro-stimulation, the pressure wave comprising first and further pressure pulses induced by the first and further electro-stimulation pulses respectively;
   determining a first characteristic of the first pressure pulse, the first characteristic of the first pressure pulse being indicative of the shape of the upward slope of the first pressure pulse; and
   for at least some of the further pressure pulses:
   determining a first characteristic of the further pressure pulse, the first characteristic of the further pressure pulse being indicative of the shape of the upward slope of the further pressure pulse;
   determining a deviation between the first characteristic of the further pressure pulse and the first characteristic of the first pressure pulse;
   determining if the deviation exceeds a deviation threshold, and,
   in the event the deviation does not exceed the deviation threshold, adjusting the further pressure pulse by assuming that the time until peak of the further pressure pulse is measured correctly and that the shape of its upward slope can be described by the first characteristic of the first pressure pulse.

2. A method according to claim 1, wherein the first characteristic of the first pressure pulse is determined depending on an amplitude of the first pressure pulse and a maximum derivative of the upward slope of the first pressure pulse, and the first characteristic of the further pressure pulse is determined depending on an amplitude of the further pressure pulse and a maximum derivative of the upward slope of the further pressure pulse.

3. A method according to claim 2, wherein the first characteristic of each of the first pressure pulse and further pressure pulse is determined based on the following formula:

$$C(\text{pulse}) = \frac{A(\text{pulse})}{d_{max}(\text{pulse})}$$

wherein: $C(\text{pulse})$ is the first characteristic of the respective first pressure pulse and further pressure pulse, $A(\text{pulse})$ is the amplitude of the respective first pressure pulse and further pressure pulse, and $d_{max}(\text{pulse})$ is the maximum derivative of the upward slope of the respective first pressure pulse and further pressure pulse.

4. A method according to claim 3, wherein adjusting the further pressure pulse comprises:
   adjusting an amplitude of the further pressure pulse based on the following formula:

$$A_{adjusted}(\text{further\_pulse}) = C(\text{first\_pulse}) \times d_{max}(\text{further\_pulse})$$

wherein: $A_{adjusted}(\text{further\_pulse})$ is the adjusted amplitude of the further pressure pulse, $C(\text{first\_pulse})$ is the first characteristic of the first pressure pulse, and $d_{max}(\text{further\_pulse})$ is the maximum derivative of the upward slope of the further pressure pulse.

5. A method according to claim 1, wherein the deviation threshold is in a range of 10% to 20%.

6. A method according to claim 1, further comprising:
   In the event the deviation exceeds the deviation threshold, adjusting the further pressure pulse either based on a first assumption that the time until peak of the further pressure pulse is measured correctly and that the shape of its upward slope can be described by the first characteristic of the first pressure pulse, or based on a second assumption that the time until peak of the further pressure pulse is measured correctly and that the shape of its upward slope can be described by substantially subtracting a heartbeat pulse of reference from the measured further pressure pulse.

7. A method according to claim 6, wherein adjusting the further pressure pulse based on the first assumption comprises:
   determining a first adjusted amplitude of the further pressure pulse based on the first assumption.

8. A method according to claim 7, wherein the first adjusted amplitude of the further pressure pulse is determined based on the following formula:

$$A_{adjusted}(\text{further\_pulse}) = C(\text{first\_pulse}) \times d_{max}(\text{further\_pulse})$$

wherein: $A_{adjusted}(\text{further\_pulse})$ is the first adjusted amplitude of the further pressure pulse, $C(\text{first\_pulse})$ is the first characteristic of the first pressure pulse, and $d_{max}(\text{further\_pulse})$ is the maximum derivative of the upward slope of the further pressure pulse.

9. A method according to claim 7, wherein adjusting the further pressure pulse based on the second assumption comprises:
   determining a second adjusted amplitude of the further pressure pulse based on the second assumption.

10. A method according to claim 9, wherein the second adjusted amplitude of the further pressure pulse is determined depending on a second characteristic of the shape of the upward slope of the heartbeat pulse of reference.

11. A method according to claim 10, wherein the second characteristic is determined depending on an amplitude of the heartbeat pulse of reference and a time until peak of the heartbeat pulse of reference.

12. A method according to claim 11, wherein the second characteristic is determined based on the following formula:

$$C(\text{hb\_pulse}) = \frac{A(\text{hb\_pulse})}{t_s(\text{hb\_pulse})}$$

wherein: $C(\text{hb\_pulse})$ is the second characteristic of the heartbeat pulse of reference, $A(\text{hb\_pulse})$ is the amplitude of the heartbeat pulse of reference, and $t_s(\text{hb\_pulse})$ is the time until peak of the heartbeat pulse of reference.

13. A method according to claim 9, wherein the second adjusted amplitude of the further pressure pulse is determined further depending on the amplitude of the further pressure pulse and the time until peak of the further pressure pulse.

14. A method according to claim 13, wherein the second adjusted amplitude of the further pressure pulse is determined based on the following formula:

$$A_{adjusted}(\text{further\_pulse}) = A(\text{further\_pulse}) - t_S(\text{further\_pulse}) \times C(hb\_\text{pulse})$$

wherein: $A_{adjusted}(\text{further\_pulse})$ is the second adjusted amplitude of the further pressure pulse, A(further_pulse) is the amplitude of the further pressure pulse, ts(further_pulse) is the time until peak of the further pressure pulse, and C(hb_pulse) is the second characteristic of the heartbeat pulse of reference.

15. A method according to claim 9, wherein adjusting the further pressure pulse either based on the first assumption or based on the second assumption comprises:
adjusting the amplitude of the further pressure pulse by selecting the smaller of the first and second adjusted amplitudes.

16. A method according to claim 1, wherein:
the electro-stimulation is performed according to a Train of Four (TOF) pattern which is based on generating a first electro-stimulation pulse and three further electro-stimulation pulses; and wherein:
determining the muscle response further comprises determining a TOF-ratio parameter corresponding to a relation between the amplitude of one of the three further pressure pulses and the amplitude of the first pressure pulse.

17. A method according to claim 16, wherein determining the TOF-ratio parameter comprises:
verifying that A(first_pulse)≥A(second_pulse)≥A(third_pulse)≥A(fourth_pulse), in which case, the TOF-ratio parameter is the percentage of the fourth_pulse with respect to the first_pulse; wherein:
first_pulse is the first pulse in the pressure wave, and A(first_pulse) is the amplitude of said first pulse;
fourth_pulse is the fourth pulse in the pressure wave, and A(fourth_pulse) is the amplitude of said fourth pulse;
A(second_pulse) is the amplitude of the second pulse in the pressure wave; and
A(third_pulse) is the amplitude of the third pulse in the pressure wave.

18. A method according to claim 16, wherein determining the TOF-ratio parameter comprises:
verifying that A(first_pulse)≥A(second_pulse)≥A(third_pulse)<A(fourth_pulse), in which case, the TOF-ratio parameter is determined based on the following formula:

$$TOF_{RATIO} = \left(\frac{A(\text{third\_pulse})}{A(\text{first\_pulse})}\right)^X$$

wherein:
$TOF_{RATIO}$ is the TOF-ratio parameter;
A(first_pulse) is the amplitude of the first pulse in the pressure wave;
A(second_pulse) is the amplitude of the second pulse in the pressure wave;
A(third_pulse) is the amplitude of the third pulse in the pressure wave;
A(fourth_pulse) is the amplitude of the fourth pulse in the pressure wave; and X is a value used to compensate that the TOF-ratio parameter is calculated depending on the amplitude of the first and third pulses rather than on the amplitude of the first and fourth pulse.

19. A method according to claim 16, wherein determining the TOF-ratio parameter comprises:
verifying that A(first_pulse)≥A(second_pulse)<A(third_pulse)<A(fourth_pulse), in which case, the TOF-ratio parameter is determined based on the following formula:

$$TOF_{RATIO} = \left(\frac{A(\text{second\_pulse})}{A(\text{first\_pulse})}\right)^Y$$

wherein:
$TOF_{RATIO}$ is the TOF-ratio parameter;
A(first_pulse) is the amplitude of the first pulse in the pressure wave;
A(second_pulse) is the amplitude of the second pulse in the pressure wave;
A(third_pulse) is the amplitude of the third pulse in the pressure wave;
A(fourth_pulse) is the amplitude of the fourth pulse in the pressure wave; and
Y is a value used to compensate that the TOF-ratio parameter is calculated depending on the amplitude of the first and second pulses rather than the amplitude of the first and fourth pulses.

20. A system for determining a muscle response to an electro-stimulation of the muscle in a patient, the system being configured to:
determine the end of a heartbeat of the patient;
perform the electro-stimulation of the muscle by causing generation of a first electro-stimulation pulse and, subsequently, one or more further electro-stimulation pulses, the first electro-stimulation pulse being generated substantially at the end of the heartbeat;
determine the muscle response in the form of a pressure wave representing how pressure varies over time in a pressure cuff as a muscle reaction to the electro-stimulation, the pressure wave comprising first and further pressure pulses induced by the first and further electro-stimulation pulses respectively;
determine a first characteristic of the first pressure pulse, the first characteristic of the first pressure pulse being indicative of the shape of the upward slope of the first pressure pulse; and
for at least some of the further pressure pulses:
determine a first characteristic of the further pressure pulse, the first characteristic of the further pressure pulse being indicative of the shape of the upward slope of the further pressure pulse;
determine a deviation between the first characteristic of the further pressure pulse and the first characteristic of the first pressure pulse;
determine if the deviation exceeds a deviation threshold, and,
in the event the deviation does not exceed the deviation threshold, adjust the further pressure pulse by assuming that the time until peak of the further pressure pulse is measured correctly and that the shape of its upward slope can be described by the first characteristic of the first pressure pulse.

* * * * *

UNITED STATES PATENT AND TRADEMARK OFFICE
CERTIFICATE OF CORRECTION

PATENT NO. : 10,537,267 B2
APPLICATION NO. : 15/191028
DATED : January 21, 2020
INVENTOR(S) : José Javier Rodiera Olivé et al.

Page 1 of 1

It is certified that error appears in the above-identified patent and that said Letters Patent is hereby corrected as shown below:

In the Specification

Column 23, Line 30, delete "FTC" and insert --PTC--

Column 47, Line 13, delete "FTC" and insert --PTC--

Column 47, Line 23, delete "FTC" and insert --PTC--

Signed and Sealed this
Twenty-third Day of June, 2020

Andrei Iancu
*Director of the United States Patent and Trademark Office*